（12）United States Patent  
Eder

(10) Patent No.: US 7,730,063 B2  
(45) Date of Patent: Jun. 1, 2010

(54) PERSONALIZED MEDICINE SERVICE

(75) Inventor: Jeffrey Scott Eder, Mill Creek, WA (US)

(73) Assignee: Asset Trust, Inc., Bothell, WA (US)

( * ) Notice: Subject to any disclaimer, the term of this patent is extended or adjusted under 35 U.S.C. 154(b) by 635 days.

(21) Appl. No.: 11/094,171

(22) Filed: Mar. 31, 2005

(65) Prior Publication Data

US 2005/0246314 A1  Nov. 3, 2005

Related U.S. Application Data

(63) Continuation-in-part of application No. 10/717,026, filed on Nov. 19, 2003.

(60) Provisional application No. 60/566,614, filed on Apr. 29, 2004, provisional application No. 60/432,283, filed on Dec. 10, 2002, provisional application No. 60/464,837, filed on Jul. 23, 2003.

(51) Int. Cl.  
*G06F 7/00* (2006.01)  
*G06F 15/173* (2006.01)  
*G06F 10/00* (2006.01)

(52) U.S. Cl. ............... 707/736; 707/758; 707/999.104; 709/224; 705/2

(58) Field of Classification Search ................. 707/101, 707/104.1, 736, 999.104; 705/1, 2  
See application file for complete search history.

(56) References Cited

U.S. PATENT DOCUMENTS

| | | | |
|---|---|---|---|
| 3,646,606 A | 2/1972 | Buxton et al. | |
| 3,749,892 A | 7/1973 | Stenning | |
| 3,933,305 A | 1/1976 | Murphy | |
| 4,489,387 A | 12/1984 | Lamb et al. | |
| 4,839,804 A | 6/1989 | Roberts et al. | |
| 4,989,141 A | 1/1991 | Lyons | |
| 5,128,861 A | 7/1992 | Kagami | |
| 5,191,522 A | 3/1993 | Bosco et al. | |
| 5,193,055 A | 3/1993 | Brown | |
| 5,199,439 A * | 4/1993 | Zimmerman et al. | ........ 600/483 |
| 5,224,034 A | 6/1993 | Katz | |
| 5,237,495 A | 8/1993 | Morii | |
| 5,237,496 A | 8/1993 | Kagami et al. | |
| 5,255,187 A | 10/1993 | Sorenson | |
| 5,317,504 A | 5/1994 | Nakayama | |
| 5,361,201 A | 11/1994 | Jost et al. | |
| 5,406,477 A | 4/1995 | Harhen | |
| 5,414,621 A | 5/1995 | Hough | |
| 5,435,565 A | 7/1995 | Benaderet | |

(Continued)

FOREIGN PATENT DOCUMENTS

EP  0 587 290 A2  3/1994

(Continued)

OTHER PUBLICATIONS

Kulkarni, Arun; Artificial neural networks for image understanding; Jan. 1, 1994; Van Norstrand Reinhold.

(Continued)

*Primary Examiner*—Miranda Le

(57) ABSTRACT

Methods, program storage devices and systems for developing a Personalized Medicine Service for an individual or group of individuals that can support the operation, customization and coordination of computer systems, software, products, services, data, entities and/or devices.

11 Claims, 29 Drawing Sheets

U.S. PATENT DOCUMENTS

| | | |
|---|---|---|
| 5,471,611 A | 11/1995 | McGregor |
| 5,542,420 A | 8/1996 | Goldman et al. |
| 5,574,828 A | 11/1996 | Hayward et al. |
| 5,644,727 A | 7/1997 | Atkins |
| 5,649,181 A | 7/1997 | French et al. |
| 5,668,591 A | 9/1997 | Shintani |
| 5,680,305 A | 10/1997 | Agpar |
| 5,704,045 A | 12/1997 | King et al. |
| 5,704,055 A | 12/1997 | George et al. |
| 5,704,366 A * | 1/1998 | Tacklind et al. ............. 600/529 |
| 5,706,495 A | 1/1998 | Chadha et al. |
| 5,724,580 A | 3/1998 | Levin et al. |
| 5,737,581 A | 4/1998 | Keane |
| 5,742,775 A | 4/1998 | King |
| 5,752,262 A | 5/1998 | Cassetti et al. |
| 5,765,154 A | 6/1998 | Horikiri et al. |
| 5,774,873 A | 6/1998 | Berent et al. |
| 5,794,219 A | 8/1998 | Brown |
| 5,802,501 A | 9/1998 | Graff |
| 5,809,282 A | 9/1998 | Cooper |
| 5,812,988 A | 9/1998 | Sandretto |
| 5,819,237 A | 10/1998 | Garman |
| 5,839,438 A | 11/1998 | Graettinger et al. |
| 5,875,431 A | 2/1999 | Heckman et al. |
| 5,951,300 A | 9/1999 | Brown |
| 5,974,412 A * | 10/1999 | Hazlehurst et al. .............. 707/3 |
| 5,985,559 A | 11/1999 | Brown |
| 5,999,881 A | 12/1999 | Law et al. |
| 6,014,629 A | 1/2000 | DeBruin-Ashton |
| 6,024,699 A * | 2/2000 | Surwit et al. ................ 600/300 |
| 6,032,119 A | 2/2000 | Brown et al. |
| 6,047,259 A * | 4/2000 | Campbell et al. .............. 705/3 |
| 6,064,971 A | 5/2000 | Hartnett |
| 6,064,972 A | 5/2000 | Jankowitz et al. |
| 6,065,003 A | 5/2000 | Sedluk |
| 6,078,901 A | 6/2000 | Ching |
| 6,092,056 A | 7/2000 | Tull, Jr. et al. |
| 6,093,146 A | 7/2000 | Filangeri |
| 6,112,188 A | 8/2000 | Hartnett |
| 6,125,355 A | 9/2000 | Bekaert et al. |
| 6,134,536 A | 10/2000 | Shepherd |
| 6,148,293 A | 11/2000 | King |
| 6,173,276 B1 | 1/2001 | Kant |
| 6,189,011 B1 | 2/2001 | Lim et al. |
| 6,209,124 B1 | 3/2001 | Vermeire et al. |
| 6,221,009 B1 | 4/2001 | Doi et al. |
| 6,234,964 B1 | 5/2001 | Iliff |
| 6,249,784 B1 | 6/2001 | Macke et al. |
| 6,263,314 B1 | 7/2001 | Donner |
| 6,278,981 B1 | 8/2001 | Dembo et al. |
| 6,278,999 B1 | 8/2001 | Knapp |
| 6,282,531 B1 | 8/2001 | Haughton et al. |
| 6,301,584 B1 | 10/2001 | Ranger |
| 6,315,719 B1 | 11/2001 | Rode et al. |
| 6,327,590 B1 | 12/2001 | Chidlovskii et al. |
| 6,332,163 B1 | 12/2001 | Bowman-Amuah |
| 6,364,834 B1 | 4/2002 | Reuss et al. |
| 6,366,934 B1 | 4/2002 | Cheng et al. |
| 6,375,469 B1 | 4/2002 | Brown |
| 6,385,589 B1 | 5/2002 | Trusheim et al. |
| 6,386,882 B1 * | 5/2002 | Linberg ...................... 434/262 |
| 6,418,448 B1 | 7/2002 | Sarkar |
| 6,490,579 B1 | 12/2002 | Gao et al. |
| 6,499,843 B1 | 12/2002 | Cox et al. |
| 6,510,430 B1 | 1/2003 | Oberwager et al. |
| 6,518,069 B1 | 2/2003 | Otvos et al. |
| 6,559,714 B2 | 5/2003 | Park et al. |
| 6,564,213 B1 | 5/2003 | Ortega et al. |
| 6,576,471 B2 | 6/2003 | Otvos |
| 6,584,507 B1 | 6/2003 | Bradley et al. |
| 6,612,986 B2 | 9/2003 | Doi et al. |
| 6,633,865 B1 | 10/2003 | Liao |
| 6,645,124 B1 | 11/2003 | Clem |
| 6,654,389 B1 | 11/2003 | Brunheroto et al. |
| 6,669,631 B2 * | 12/2003 | Norris et al. ................ 600/300 |
| 6,684,204 B1 | 1/2004 | Lal |
| 6,695,795 B2 | 2/2004 | Knoll |
| 6,732,095 B1 | 5/2004 | Warshavsky et al. |
| 6,738,753 B1 | 5/2004 | Hogan |
| 6,741,264 B1 | 5/2004 | Lesser |
| 6,756,983 B1 | 6/2004 | Borosh et al. |
| 6,757,898 B1 | 6/2004 | Ilsen et al. |
| 6,769,127 B1 | 7/2004 | Bonomi et al. |
| 6,835,176 B2 | 12/2004 | McNair |
| 6,847,729 B1 | 1/2005 | Clinch et al. |
| 6,849,045 B2 * | 2/2005 | Iliff ........................... 600/300 |
| 6,879,972 B2 | 4/2005 | Brandon et al. |
| 6,893,396 B2 | 5/2005 | Schulze et al. |
| 6,895,475 B2 | 5/2005 | Volpe et al. |
| 6,926,708 B1 | 8/2005 | Franks-Farah et al. |
| 6,947,988 B1 | 9/2005 | Saleh |
| 6,963,827 B1 | 11/2005 | Elyea et al. |
| 7,000,220 B1 | 2/2006 | Booth |
| 7,006,480 B2 | 2/2006 | Border et al. |
| 7,047,227 B2 | 5/2006 | Batachia et al. |
| 7,096,299 B2 | 8/2006 | Meynard |
| 7,099,799 B2 | 8/2006 | Huard |
| 7,123,953 B2 | 10/2006 | Starobin et al. |
| 7,127,082 B2 | 10/2006 | Neely |
| 7,139,764 B2 | 11/2006 | Lee |
| 7,162,379 B2 | 1/2007 | Jang et al. |
| 7,170,510 B2 | 1/2007 | Kawahara et al. |
| 7,171,384 B1 | 1/2007 | Fitzpatrick et al. |
| 7,194,070 B2 | 3/2007 | Starbuck et al. |
| 7,197,502 B2 | 3/2007 | Feinsmith |
| 7,200,384 B1 | 4/2007 | Tervo et al. |
| 7,216,121 B2 | 5/2007 | Bachman et al. |
| 7,219,105 B2 | 5/2007 | Kummamuru et al. |
| 7,231,399 B1 | 6/2007 | Bem et al. |
| 7,237,023 B2 | 6/2007 | Menard et al. |
| 7,240,295 B2 | 7/2007 | Bybee et al. |
| 7,245,144 B1 | 7/2007 | Wong et al. |
| 7,249,342 B2 | 7/2007 | Pack et al. |
| 7,256,708 B2 | 8/2007 | Rosenfeld et al. |
| 7,258,667 B2 | 8/2007 | McNair |
| 7,260,498 B2 | 8/2007 | Battenfelder et al. |
| 7,269,569 B2 | 9/2007 | Spira et al. |
| 7,277,864 B2 | 10/2007 | Ohnemus et al. |
| 7,283,553 B2 | 10/2007 | Kishigami et al. |
| 7,293,010 B2 | 11/2007 | Angele et al. |
| 7,395,216 B2 | 7/2008 | Rosenfeld et al. |
| 2001/0013006 A1 | 8/2001 | Brown |
| 2002/0002520 A1 | 1/2002 | Gatto |
| 2002/0016758 A1 | 2/2002 | Grigsby |
| 2002/0023034 A1 | 2/2002 | Brown et al. |
| 2002/0033753 A1 | 3/2002 | Imbo |
| 2002/0048755 A1 | 4/2002 | Cohen |
| 2002/0052820 A1 | 5/2002 | Gatto |
| 2002/0087532 A1 | 7/2002 | Barritz et al. |
| 2002/0087535 A1 | 7/2002 | Kotcheff et al. |
| 2002/0147880 A1 | 10/2002 | Wang Baldonado |
| 2002/0152222 A1 | 10/2002 | Holbrook |
| 2002/0169759 A1 | 11/2002 | Kraft et al. |
| 2003/0018961 A1 | 1/2003 | Ogasawara |
| 2003/0036683 A1 * | 2/2003 | Kehr et al. ................ 600/300 |
| 2003/0036783 A1 | 2/2003 | Bauhahn et al. |
| 2003/0037043 A1 | 2/2003 | Chang et al. |
| 2003/0040900 A1 | 2/2003 | D'Agostini |
| 2003/0083973 A1 | 5/2003 | Horsfall |
| 2003/0217097 A1 | 11/2003 | Eitel |
| 2003/0220819 A1 * | 11/2003 | Burstein et al. ................ 705/3 |
| 2004/0078220 A1 | 4/2004 | Jackson |
| 2004/0083101 A1 | 4/2004 | Brown et al. |
| 2004/0100494 A1 | 5/2004 | Ragoler et al. |

| | | | |
|---|---|---|---|
| 2004/0107181 | A1 | 6/2004 | Rodden |
| 2004/0139106 | A1 | 7/2004 | Bachman et al. |
| 2004/0193019 | A1 | 9/2004 | Wei |
| 2004/0193894 | A1 | 9/2004 | Chaudhari et al. |
| 2004/0194099 | A1 | 9/2004 | Lamping et al. |
| 2004/0236608 | A1* | 11/2004 | Ruggio et al. .......... 705/2 |
| 2004/0254932 | A1 | 12/2004 | Gupta et al. |
| 2004/0260695 | A1 | 12/2004 | Brill |
| 2005/0027507 | A1 | 2/2005 | Patrudu |
| 2005/0027562 | A1 | 2/2005 | Brown |
| 2005/0038669 | A1 | 2/2005 | Sachdeva et al. |
| 2005/0043965 | A1 | 2/2005 | Heller et al. |
| 2005/0060311 | A1 | 3/2005 | Tong et al. |
| 2005/0110268 | A1 | 5/2005 | Schone |
| 2008/0082966 | A1* | 4/2008 | Dorn et al. .......... 717/120 |

FOREIGN PATENT DOCUMENTS

GB    2 253 081 A    2/1992

OTHER PUBLICATIONS

Ward Systems Group; NeuroWindows User Manual; 1993; Wards Systems Group.

Bouquet, Paolo, Searafini, Luciano, et al; Modeling and Using Context—Context 99, Sep. 1999, Springer.

Akman, Varol, Bouquet, Paolo, et al; Modeling and Using Context—Context 2001, Jul. 2001, Springer.

Blackburn, Patrick, Ghidini, Chiara, et al; Modeling and Using Context—Context 2003, Jun. 2003, Springe.

Franke, Jurgen, Hardle, Wolfgang, et al; Measuring Risk in Complex Stochastic Systems; 2000, Springe.

Garson, David; Interpreting neural network connection weights, Apr. 1, 1991, AI Expert.

Brewka, Gerhard, Principles of Knowledge Representation, 1996, CSLI Publications.

Reiter, Raymond, Knowledge in Action, 2001, MIT Press.

Chappell, David & Jewell, Tyler, Java Web Services; 2002, O'Reilly.

Glass, Graham, Web Services, Prentice Hall, 2002.

Conway, Susan & Sligar, Char, Unlocking Knowledge Assets, 2002, Microsoft Press.

Marcus, Robert & Watters, Beverley; Collective Knowledge, 2002, Microsoft Press.

Barabasi, Albert-Laszlo, Linked—the new science of networks, Apr. 2002; Perseus.

Blythe, Jim, "An Integrated Environment for Knowledge Acquisition", 2001, Intelligent User Interface.

Clark, Peter, et al, "Knowledge entry as graphical assembly of components", 2001, K-Cap 01.

Pfeffer, Avi, "A Bayesian Language for Cumulative Learning", 2000, AAII.

Kuehne, Sven, et al, "SEQL: Category learning as progressive abstraction using structure mapping", 2.

Fowler, Martin; Analysis Patterns: Reusable Object Models, 1997, Addison Wesley.

Bergstrom, Peter; Kimber Eliot, "Formal data models for SGML and HyTime", SGML, Mar. 1999, electrum.

Caruso, Denise, "A challenge to gene theory, a tougher look at biotech", New York Times, Jul. 1, 2007, New York, U.S.A.

The Encode Project Consortium, "Identification and analysis of functional elements in 1% of the human genome", Nature, Jun. 14, 2007, V 445, p. 799-816, USA.

Medstat, Inc., "Medstat Disease Staging Software Version 5.22 Reference Guide", 2004, pp. 1-115, Medstat, Inc., Ann Arbor, Michigan, USA.

Business Wire, "Apache Medical Systems announces new versions of two leading clinical decision support products", May 17, 1999, pp. 1-3, Business Wire, USA.

Rhode Island DHS, "Rhode Island Medical Assistance Program Provider Update Newsletter", Jun. 1994, vol. 11, pp. 1-5, Rhode Island DHS, USA.

University of Maryland University College, "Intelligent Agents and how they are changing our learning", UMUC website, Aug. 20, 2003.

Halford, Graeme et al,"Separating Cognitive Capacity from Knowledge", Trends in Cognitive Science, Jun. 2007, pp. 236-242, Cell Press, U.S.A.

Science News Letter, The, "Unlearning is problem", The Science News Letter, Feb. 4, 1956, p. 67, vol. 69, Society for Science & the Public, USA.

Botknowledge, "Botknowledge—Frequently Asked Questions", 2000, pp. 1-3, www.botknowledge.com, U.S.A.

Notre Dame, Cedric and Claverie, Jean Michel, "Bioinformatics for dummies", pp. 1-452, 2003, Wiley Publishing, U.S.A.

Knaus, WA et al, "The APACHE III prognostic system", Chest, Dec. 1991, pp. 1619-1636, American College of Chest Physicians, U.S.A.

Wikipedia, "ICU Scoring Systems", en.wikipedia.org, Aug. 14, 2009.

Google "Lyapunov—Health Care search results", www.google.com, Oct. 5, 2009.

Open Clinical, Apache III, www.openclinical.org, Mar. 3, 2005.

Illuminate, Inc, "Illuminate Solutions acquires Synera Systems Intellectual Property and Assets," Jun. 24, 2007, Barcelona, Spain.

Cerner, "APACHE IV Equations", pp. 1-37, Jun. 21, 2005.

Wikipedia, "Lyapunov exponent", en.wikipedia.org, Sep. 25, 2009.

Business Week, "Vital Springs Technologies", investing.businessweek.com, Jul. 13, 2009, p. 1.

* cited by examiner

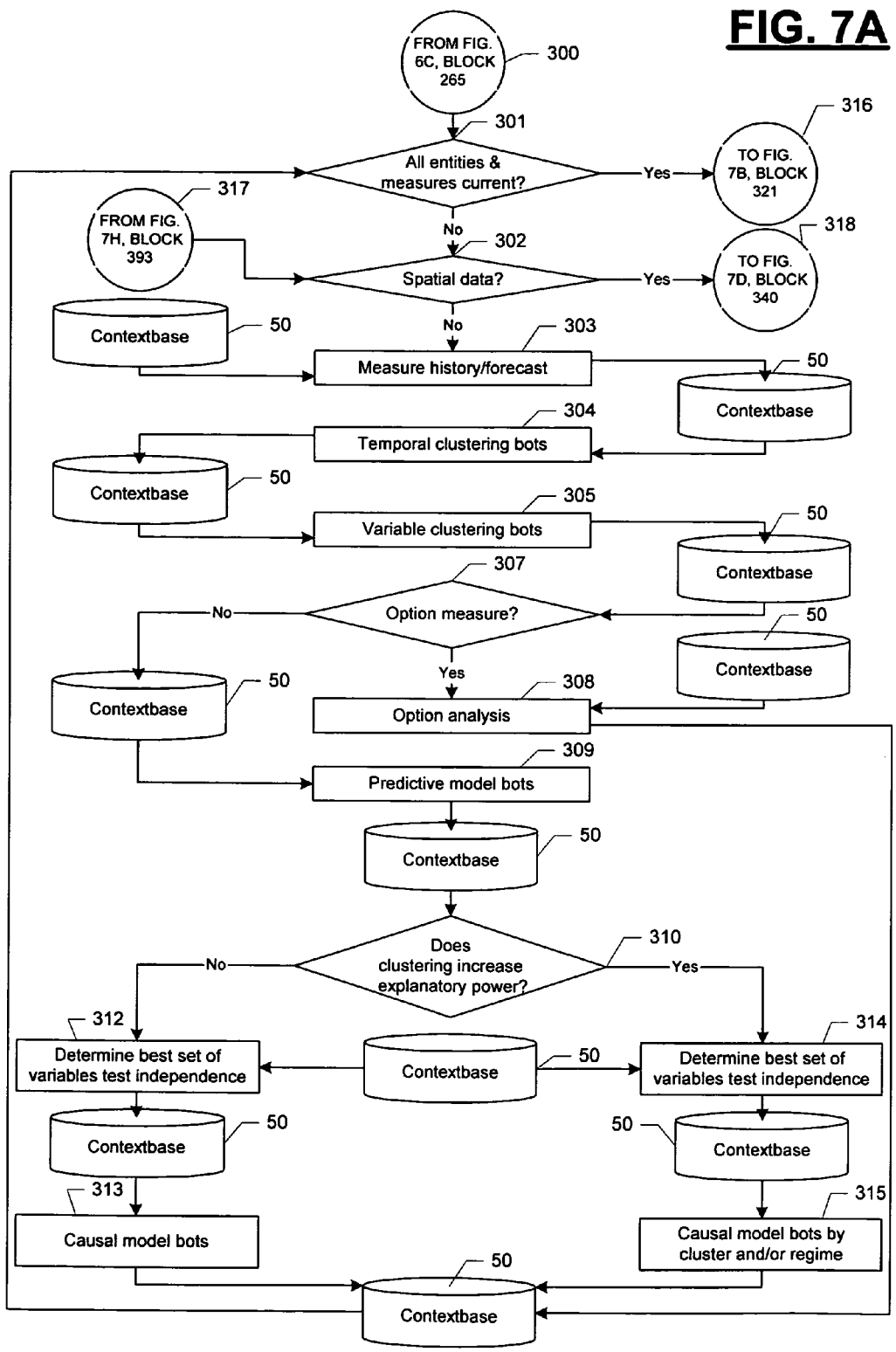

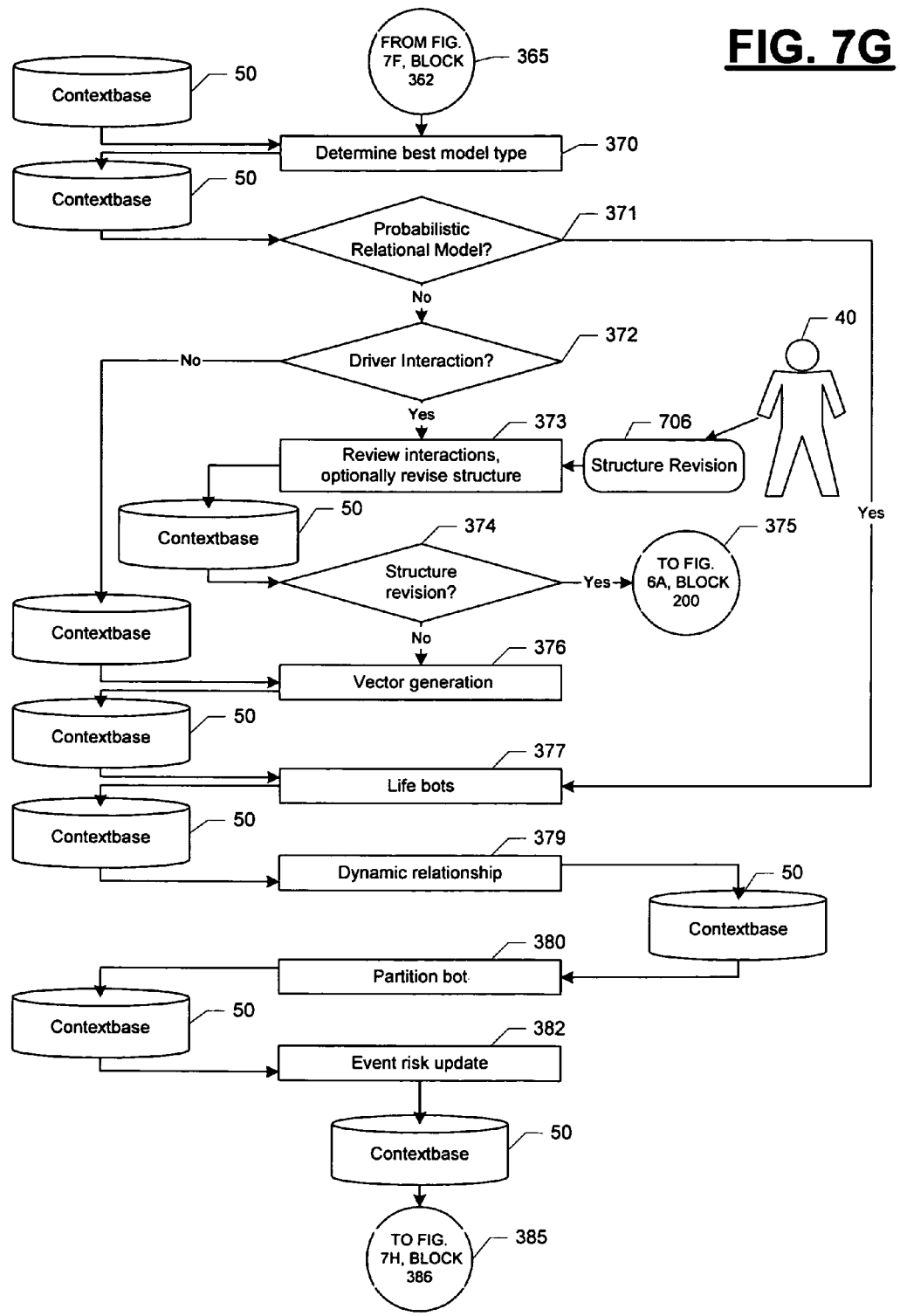

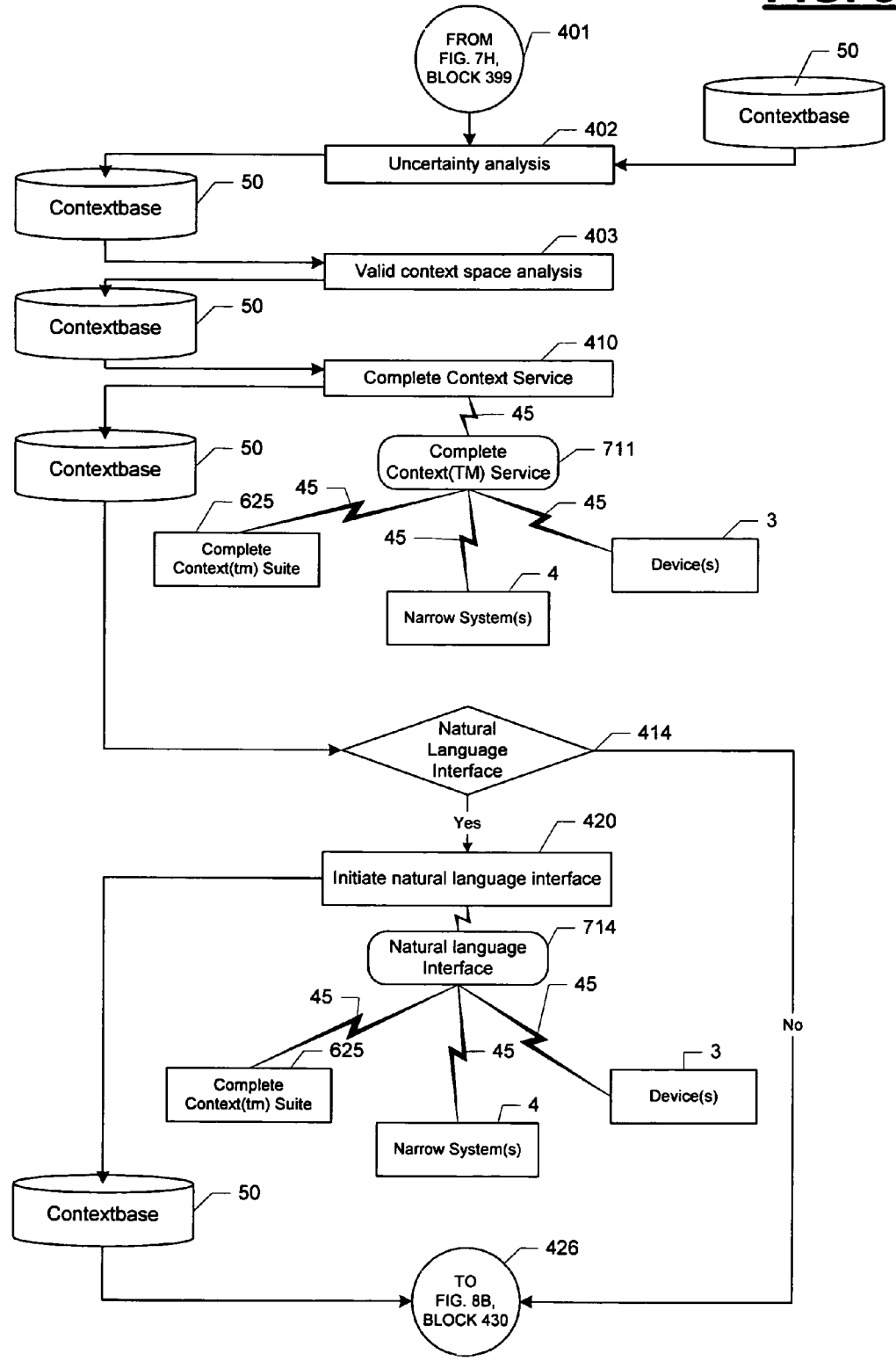

Universal Context Specification*

FIG. 17

| Component of context | Considered? (yes or no) | If yes - details to be identified (in addition to impact and relationship to other components of context) |
|---|---|---|
| Locations (901) | | Reference frame, format |
| Projects (902) | | Type of project, timeline |
| Events (903) | | Normal, extreme or combination |
| Virtual locations (904) | | Reference frame, format |
| Factors (905) | | |
| Resources (906) | | |
| Elements (907) | | |
| Actions (908) | | |
| Transactions (909) | | |
| Function (910) | yes | Function & variability measure specification |
| Process(es) (911) | | |
| Mission(s) (912) | | Mission & variability measure specification |
| Constraints (913) | | Component(s) of context and constraint(s) |
| Preferences (914) | | Component(s) of context and constraint(s) |
| Lexicon (955) | | |
| User(s): | | |
| Display options: | | |
| Entity: (Area(s), Hierarchy(s) or Group(s), Type(s)) | | |

* for an subject, entity, function and/or mission measure combination

PERSONALIZED MEDICINE SERVICE

RELATED PROVISIONAL APPLICATION AND CONTINUATION IN PART

This application is a non provisional of U.S. Provisional Patent application No. 60/566,614 filed on Apr. 29, 2004 the disclosure of which is incorporated herein by reference. This application is also a continuation in part of pending U.S. patent application Ser. No. 10/717,026 filed on Nov. 19, 2003. Application Ser. No. 10/717,026 claimed priority from provisional application No. 60/432,283 filed on Dec. 10, 2002 and provisional application No. 60/464,837 filed on Apr. 23, 2003 the disclosures of which are also incorporated herein by reference.

BACKGROUND OF THE INVENTION

This invention relates to methods, program storage devices and systems for developing a Personalized Medicine Service (100) for an individual or group of individuals that can support the operation, customization and coordination of computer systems, software, products, services, data, entities and/or devices.

SUMMARY OF THE INVENTION

It is a general object of the present invention to provide a novel, useful system that develops and maintains one or more individual and/or group contexts in a systematic fashion and uses the one or more contexts to develop a Personalized Medicine Service (100) that supports the operation and coordination of software including a Complete Context™ Suite of services (625), a Complete Context™ Development System (610) and a plurality of Complete Context™ Bots (650), one or more external services (9), one or more narrow systems (4), entities and/or one or more devices (3).

The innovative system of the present invention supports the development and integration of any combination of data, information and knowledge from systems that analyze, monitor, support and/or are associated with entities in three distinct areas: a social environment area (1000), a natural environment area (2000) and a physical environment area (3000). Each of these three areas can be further subdivided into domains. Each domain can in turn be divided into a hierarchy or group. Each member of a hierarchy or group is a type of entity.

The social environment area (1000) includes a political domain hierarchy (1100), a habitat domain hierarchy (1200), an intangibles domain group (1300), an interpersonal domain group (1400), a market domain hierarchy (1500) and an organization domain hierarchy (1600). The political domain hierarchy (1100) includes a voter entity type (1101), a precinct entity type (1102), a caucus entity type (1103), a city entity type (1104), a county entity type (1105), a state/province entity type (1106), a regional entity type (1107), a national entity type (1108), a multi-national entity type (1109) and a global entity type (1110). The habitat domain hierarchy includes a household entity type (1202), a neighborhood entity type (1203), a community entity type (1204), a city entity type (1205) and a region entity type (1206). The intangibles domain group (1300) includes a brand entity type (1301), an expectations entity type (1302), an ideas entity type (1303), an ideology entity type (1304), a knowledge entity type (1305), a law entity type (1306), a intangible asset entity type (1307), a right entity type (1308), a relationship entity type (1309), a service entity type (1310) and a securities entity type (1311). The interpersonal group includes (1400) includes an individual entity type (1401), a nuclear family entity type (1402), an extended family entity type (1403), a clan entity type (1404), an ethnic group entity type (1405), a neighbors entity type (1406) and a friends entity type (1407). The market domain hierarchy (1500) includes a multi entity type organization entity type (1502), an industry entity type (1503), a market entity type (1504) and an economy entity type (1505). The organization domain hierarchy (1600) includes team entity type (1602), a group entity type (1603), a department entity type (1604), a division entity type (1605), a company entity type (1606) and an organization entity type (1607). These relationships are summarized in Table 1.

TABLE 1

| Social Environment Domains | Members (lowest level to highest for hierarchies) |
| --- | --- |
| Political (1100) | voter (1101), precinct (1102), caucus (1103), city (1104), county (1105), state/province (1106), regional (1107), national (1108), multi-national (1109), global (1110) |
| Habitat (1200) | household (1202), neighborhood (1203), community (1204), city (1205), region (1206) |
| Intangibles Group (1300) | brand (1301), expectations (1302), ideas (1303), ideology (1304), knowledge (1305), law (1306), intangible assets (1307), right (1308), relationship (1309), service (1310), securities (1311) |
| Interpersonal Group (1400) | individual (1401), nuclear family (1402), extended family (1403), clan (1404), ethnic group (1405), neighbors (1406), friends (1407) |
| Market (1500) | multi-entity organization (1502), industry (1503), market (1504), economy (1505) |
| Organization (1600) | team (1602), group (1603), department (1604), division (1605), company (1606), organization (1607) |

The natural environment area (2000) includes a biology domain hierarchy (2100), a cellular domain hierarchy (2200), an organism domain hierarchy (2300) and a protein domain hierarchy (2400) as shown in Table 2. The biology domain hierarchy (2100) contains a species entity type (2101), a genus entity type (2102), a family entity type (2103), an order entity type (2104), a class entity type (2105), a phylum entity type (2106) and a kingdom entity type (2107). The cellular domain hierarchy (2200) includes a macromolecular complexes entity type (2202), a protein entity type (2203), a rna entity type (2204), a dna entity type (2205), an x-ylation** entity type (2206), an organelles entity type (2207) and cells entity type (2208). The organism domain hierarchy (2300) contains a structures entity type (2301), an organs entity type (2302), a systems entity type (2303) and an organism entity type (2304). The protein domain hierarchy contains a monomer entity type (2400), a dimer entity type (2401), a large oligomer entity type (2402), an aggregate entity type (2403) and a particle entity type (2404). These relationships are summarized in Table 2.

TABLE 2

| Natural Environment Domains | Members (lowest level to highest for hierarchies) |
|---|---|
| Biology (2100) | species (2101), genus (2102), family (2103), order (2104), class (2105), phylum (2106), kingdom (2107) |
| Cellular* (2200) | macromolecular complexes (2202), protein (2203), rna (2204), dna (2205), x-ylation** (2206), organelles (2207), cells (2208) |
| Organism (2300) | structures (2301), organs (2302), systems (2303), organism (2304) |
| Protein (2400) | monomer (2400), dimer (2401), large oligomer (2402), aggregate (2403), particle (2404) |

*includes viruses
**x = methyl, phosphor, etc.

The physical environment area (3000) contains a chemistry group (3100), a geology domain hierarchy (3200), a physics domain hierarchy (3300), a space domain hierarchy (3400), a tangible goods domain hierarchy (3500), a water group (3600) and a weather group (3700) as shown in Table 3. The chemistry group (3100) contains a molecules entity type (3101), a compounds entity type (3102), a chemicals entity type (3103) and a catalysts entity type (3104). The geology domain hierarch contains a minerals entity type (3202), a sediment entity type (3203), a rock entity type (3204), a landform entity type (3205), a plate entity type (3206), a continent entity type (3207) and a planet entity type (3208). The physics domain hierarchy (3300) contains a quark entity type (3301), a particle zoo entity type (3302), a protons entity type (3303), a neutrons entity type (3304), an electrons entity type (3305), an atoms entity type (3306), and a molecules entity type (3307). The space domain hierarchy contains a dark matter entity type (3402), an asteroids entity type (3403), a comets entity type (3404), a planets entity type (3405), a stars entity type (3406), a solar system entity type (3407), a galaxy entity type (3408) and universe entity type (3409). The tangible goods hierarchy contains a money entity type (3501), a compounds entity type (3502), a minerals entity type (3503), a components entity type (3504), a subassemblies entity type (3505), an assemblies entity type (3506), a subsystems entity type (3507), a goods entity type (3508) and a systems entity type (3509). The water group (3600) contains a pond entity type (3602), a lake entity type (3603), a bay entity type (3604), a sea entity type (3605), an ocean entity type (3606), a creek entity type (3607), a stream entity type (3608), a river entity type (3609) and a current entity type (3610). The weather group (3700) contains an atmosphere entity type (3701), a clouds entity type (3702), a lightning entity type (3703), a precipitation entity type (3704), a storm entity type (3705) and a wind entity type (3706).

TABLE 3

| Physical Environment Domains | Members (lowest level to highest for hierarchies) |
|---|---|
| Chemistry Group (3100) | molecules (3101), compounds (3102), chemicals (3103), catalysts (3104) |
| Geology (3200) | minerals (3202), sediment (3203), rock (3204), landform (3205), plate (3206), continent (3207), planet (3208) |

TABLE 3-continued

| Physical Environment Domains | Members (lowest level to highest for hierarchies) |
|---|---|
| Physics (3300) | quark (3301), particle zoo (3302), protons (3303), neutrons (3304), electrons (3305), atoms (3306), molecules (3307) |
| Space (3400) | dark matter (3402), asteroids (3403), comets (3404), planets (3405), stars (3406), solar system (3407), galaxy (3408), universe (3409) |
| Tangible Goods (3500) | money (3501), compounds (3502), minerals (3503), components (3504), subassemblies (3505), assemblies (3506), subsystems (3507), goods (3508), systems (3509) |
| Water Group (3600) | pond (3602), lake (3603), bay (3604), sea (3605), ocean (3606), creek (3607), stream (3608), river (3609), current (3610) |
| Weather Group (3700) | atmosphere (3701), clouds (3702), lightning (3703), precipitation (3704), storm (3705), wind (3706) |

Individual entities are items of one or more entity type. The analysis of the health of an individual or group can be linked together with a plurality of different entities to support an analysis that extends across several domains. Entities and patients can also be linked together to follow a chain of events that impacts one or more patients and/or entities. These chains can be recursive. The domain hierarchies and groups shown in Tables 1, 2 and 3 can be organized into different areas and they can also be expanded, modified, extended or pruned in order to support different analyses.

Data, information and knowledge from these seventeen different domains can be integrated and analyzed in order to support the creation of one or more health contexts for the subject individual or group. The one or more contexts developed by this system focus on the function performance (note the terms behavior and function performance will be used interchangeably) of a single patient as shown in FIG. 2A, a group of two or more patients as shown in FIG. 2B and/or a patient-entity system in one or more domains as shown in FIG. 2C. FIG. 2A shows an entity (900) and a function impact network diagram for a location (901), a project (902), an event (903), a virtual location (904), a factor (905), a resource (906), an element (907), an action/transaction (908/909), a function measure (910), a process (911), a subject mission (912), constraint (913) and a preference (914). FIG. 2B shows a collaboration (925) between two entities and the function impact network diagram for locations (901), projects (902), events (903), virtual locations (904), factors (905), resources (906), elements (907), action/transactions (908/909), a joint measure (915), processes (911), a joint mission (916), constraints (913) and preferences (914). For simplicity we will hereinafter use the terms patient or subject with the understanding that they refer to a patient (900) as shown in FIG. 2A, a group of two or more patients (925) as shown in FIG. 2B or a patient-entity system (950) as shown in FIG. 2C. While only two entities are shown in FIG. 2B and FIG. 2C it is to be understood that the subject can contain more than two patients and/or entities.

After one or more contexts are developed for the subject, they can be combined, reviewed, analyzed and/or applied using one or more of the context-aware services in a Complete Context™ Suite (625) of services. These services are optionally modified to meet user requirements using a Complete Context™ Development System (610). The Complete Context™ Development System (610) supports the maintenance of the services in the Complete Context™ Suite (625), the creation of newly defined stand-alone services, the development of new services and/or the programming of context-aware bots.

The system of the present invention systematically develops the one or more complete contexts for distribution in a Personalized Medicine Service (100). These contexts are in turn used to support the comprehensive analysis of subject performance, develop one or more shared contexts to support collaboration, simulate subject performance and/or turn data into knowledge. Processing in the Personalized Medicine Service (100) is completed in three steps:

1. subject definition and measure specification;
2. context and contextbase (50) development, and
3. Complete Context™ service development and distribution.

The first processing step in the Personalized Medicine Service (100) defines the subject that will be analyzed, prepares the data from devices (3), entity narrow system databases (5), partner narrow system databases (6), external databases (7), the World Wide Web (8), external services (9) and/or the Complete Context™ Input System (601) for use in processing and then uses these data to specify subject functions as well as function and/or mission measures.

As part of the first stage of processing, the user (40) identifies the subject by using existing hierarchies and groups, adding a new hierarchy or group or modifying the existing hierarchies and/or groups in order to fully define the subject. As discussed previously, each subject comprises one of three types. These definitions can be supplemented by identifying actions, constraints, elements, events, factors, preferences, processes, projects, risks and resources that impact the subject. For example, a white blood cell entity is an item with the cell entity type (2208) and an element of the circulatory system and auto-immune system (2303). In a similar fashion, entity Jane Doe could be an item within the organism entity type (2300), an item within the voter entity type (1101), an element of a team entity (1602), an element of a nuclear family entity (1402), an element of an extended family entity (1403) and an element of a household entity (1202). This individual would be expected to have one or more functions and function and/or mission measures for each entity type she is associated with. Separate systems that tried to analyze the six different roles of the individual in each of the six hierarchies would probably save some of the same data six separate times and use the same data in six different ways. At the same time, all of the work to create these six separate systems might provide very little insight because the complete context for behavior of this subject at any one period in time is a blend of the context associated with each of the six different functions she is simultaneously performing in the different domains. Predefined templates for the different entity types can be used at this point to facilitate the specification of the subject (these same templates can be used to accelerate learning by the system of the present invention). This specification can include an identification of other subjects that are related to the entity. For example, the individual could identify her friends, family, home, place of work, church, car, typical foods, hobbies, favorite malls, etc. using one of these predefined templates. The user could also indicate the level of impact of each of these entities has on different function and/or mission measures. These weightings can in turn be verified by the system of the present invention.

After the subject definition is completed, structured data and information, transaction data and information, descriptive data and information, unstructured data and information, text data and information, geo-spatial data and information, image data and information, array data and information, web data and information, video data and video information, device data and information, and/or service data and information are made available for analysis by converting data formats before mapping these data to a contextbase (50) in accordance with a common schema or ontology. The automated conversion and mapping of data and information from the existing devices (3) narrow computer-based system databases (5 & 6), external databases (7), the World Wide Web (8) and external services (9) to a common schema or ontology significantly increases the scale and scope of the analyses that can be completed by users. This innovation also gives users (40) the option to extend the life of their existing narrow systems (4) that would otherwise become obsolete. The uncertainty associated with the data from the different systems is evaluated at the time of integration. Before going further, it should be noted that the Personalized Medicine Service (100) is also capable of operating without completing some or all narrow system database (5 & 6) conversions and integrations as it can directly accept data that complies with the common schema or ontology. The Personalized Medicine Service (100) is also capable of operating without any input from narrow systems (4). For example, the Complete Context™ Input Service (601) (and any other application capable of producing xml documents) is fully capable of providing all data directly to the Personalized Medicine Service (100).

The Personalized Medicine Service (100) supports the preparation and use of data, information and/or knowledge from the "narrow" systems (4) listed in Tables 4, 5, 6 and 7 and devices (3) listed in Table 8.

TABLE 4

| | |
|---|---|
| Biomedical Systems | affinity chip analyzer, array systems, biochip systems, bioinformatic systems, biological simulation systems, blood chemistry systems, blood pressure systems, body sensors, clinical management systems, diagnostic imaging systems, electronic patient record systems, electrophoresis systems, electronic medication management systems, enterprise appointment scheduling, enterprise practice management, fluorescence systems, formulary management systems, functional genomic systems, galvanic skin sensors, gene chip analysis systems, gene expression analysis systems, gene sequencers, glucose test equipment, information based medical systems, laboratory information management systems, liquid chromatography, mass spectrometer systems, microarray systems, medical testing systems, microfluidic systems, molecular diagnostic systems, nano-string systems, nano-wire systems, peptide mapping systems, pharmacoeconomic systems, pharmacogenomic data systems, pharmacy management systems, practice management systems, protein biochip analysis systems, protein mining systems, protein modeling systems, protein sedimentation systems, protein sequencer, protein visualization systems, proteomic data systems, stentennas, structural biology systems, systems biology applications, x*-ylation analysis systems |

*x = methyl, phosphor,

TABLE 5

| | |
|---|---|
| Personal Systems | appliance management systems, automobile management systems, blogs, contact management applications, credit monitoring systems, gps applications, home management systems, image archiving applications, image management applications, folksonomies, lifeblogs, media archiving applications, media applications, media management applications, personal finance applications, personal productivity applications (word processing, spreadsheet, presentation, etc.), personal database applications, personal and group scheduling applications, social networking applications, tags, video applications |

TABLE 6

| | |
|---|---|
| Scientific Systems | accelerometers, atmospheric survey systems, geological survey systems, ocean sensor systems, seismographic systems, sensors, sensor grids, sensor networks, smart dust |

TABLE 7

| | |
|---|---|
| Management Systems | accounting systems**, advanced financial systems, alliance management systems, asset and liability management systems, asset management systems, battlefield systems, behavioral risk management systems, benefits administration systems, brand management systems, budgeting/financial planning systems, building management systems, business intelligence systems, call management systems, cash management systems, channel management systems, claims management systems, command systems, commodity risk management systems, content management systems, contract management systems, credit-risk management systems, customer relationship management systems, data integration systems, data mining systems, demand chain systems, decision support systems, device management systems document management systems, email management systems, employee relationship management systems, energy risk management systems, expense report processing systems, fleet management systems, foreign exchange risk management systems, fraud management systems, freight management systems, geological survey systems, human capital management systems, human resource management systems, incentive management systems, information lifecycle management systems, information technology management systems, innovation management systems, instant messaging systems, insurance management systems, intellectual property management systems, intelligent storage systems, interest rate risk management systems, investor relationship management systems, knowledge management systems, litigation tracking systems, location management systems, maintenance management systems, manufacturing execution systems, material requirement planning systems, metrics creation system, online analytical processing systems, ontology systems, partner relationship management systems, payroll systems, performance dashboards, performance management systems, price optimization systems, private exchanges, process management systems, product life-cycle management systems, project management systems, project portfolio management systems, revenue management systems, risk management information systems, sales force automation systems, scorecard systems, sensors (includes RFID), sensor grids (includes RFID), service management systems, simulation systems, six-sigma quality management systems, shop floor control systems, strategic planning systems, supply chain systems, supplier relationship management systems, support chain systems, system management applications, taxonomy systems, technology chain systems, treasury management systems, underwriting |

TABLE 7-continued

| | |
|---|---|
| | systems, unstructured data management systems, visitor (web site) relationship management systems, weather risk management systems, workforce management systems, yield management systems and combinations thereof |

**these typically include an accounts payable system, accounts receivable system, inventory system, invoicing system, payroll system and purchasing system

TABLE 8

| | |
|---|---|
| Devices | personal digital assistants, phones, watches, clocks, lab equipment, personal computers, televisions, radios, personal fabricators, personal health monitors, refrigerators, washers, dryers, ovens, lighting controls, alarm systems, security systems, hvac systems, gps devices, smart clothing (aka clothing with sensors), personal biomedical monitoring devices, personal computers |

After data conversions have been identified the user (40) is asked to specify entity functions. The user can select from pre-defined functions for each subject or define new functions using narrow system data. Examples of predefined subject functions are shown in Table 9.

TABLE 9

| Entity type | Example Functions |
|---|---|
| Organism (2300) | reproduction, killing germs, maintaining blood sugar levels |

Pre-defined quantitative measures can be used if pre-defined functions were used in defining the entity. Alternatively, new measures can be created using narrow system data for one or more subjects and/or the Personalized Medicine Service (100) can identify the best fit measures for the specified functions. The quantitative measures can take any form. For example, Table 10 shows three measures for a medical organization entity—patient element health, patient element longevity and organization financial break even. The Personalized Medicine Service (100) incorporates the ability to use other pre-defined measures including each of the different types of risk—alone or in combination—as well as sustainability.

After the data integration, subject definition and measure specification are completed, processing advances to the second stage where context layers for each subject are developed and stored in a contextbase (50). Each context for a subject can be divided into eight or more types of context layers. Together, these eight layers identify: actions, constraints, elements, events, factors, preferences, processes, projects, risks, resources and terms that impact entity performance for each function; the magnitude of the impact actions, constraints, elements, events, factors, preferences, processes, projects, risks, resources ad terms have on entity performance of each function; physical and/or virtual coordinate systems that are relevant to entity performance for each function and the magnitude of the impact location relative to physical and/or virtual coordinate systems has on entity performance for each function. These eight layers also identify and quantify subject function and/or mission measure performance. The eight types of layers are:

1. A layer that defines and describes the element context over time, i.e. we store widgets (a resource) built (an action) using the new design (an element) with the automated lathe (another element) in our warehouse (an element). The lathe (element) was recently refurbished (completed action) and produces 100 widgets per 8 hour shift (element characteristic). We can increase production to 120 widgets per 8 hour shift if we add complete numerical control (a feature). This layer may be subdivided into any number of sub-layers along user specified dimensions such as tangible elements of value, intangible elements of value, processes, agents, assets and combinations thereof;

2. A layer that defines and describes the resource context over time, i.e. producing 100 widgets (a resource) requires 8 hours of labor (a resource), 150 amp hours of electricity (another resource) and 5 tons of hardened steel (another resource). This layer may be subdivided into any number of sub-layers along user specified dimensions such as lexicon (what resources are called), resources already delivered, resources with delivery commitments and forecast resource requirements;

3. A layer that defines and describes the environment context over time (the entities in the social (1000), natural (2000) and/or physical environment (3000) that impact entity function and/or mission measure performance, i.e. the volatility in the market for steel increased 50% last year, standard deviation on monthly shipments is 24% and analysts expect 30% growth in revenue this quarter. This layer may be subdivided into any number of sub-layers along user specified dimensions;

4. A layer that defines and describes the transaction context (also known as tactical/administrative context) over time, i.e. Acme owes us $30,000 for prior sales, we have made a commitment to ship 100 widgets to Acme by Tuesday and need to start production by Friday. This layer may be subdivided into any number of sub-layers along user specified dimensions such as historical transactions, committed transactions, forecast transactions, historical events, forecast events and combinations thereof;

5. A layer that defines and describes the relationship context over time, i.e. Acme is also a key supplier for the new product line, Widget X, that is expected to double our revenue over the next five years. This layer may be subdivided into any number of sub-layers along user specified dimensions;

6. A layer that defines and describes the measurement context over time, i.e. the price per widget is $100 and the cost of manufacturing widgets is $80 so we make $20 profit per unit (for most businesses this would be a short term profit measure for the value creation function). Also, Acme is one of our most valuable customers and they are a valuable supplier to the international division (value based measures). This layer may be subdivided into any number of sub-layers along user specified dimensions. For example, the instant, five year and lifetime impact of certain medical treatments may be of interest. In this instance, three separate measurement layers could be created to provide the desired context. The risks associated with each measure can be integrated within each measurement layer or they can be stored in separate layers. For example, value measures for organizations integrate the risk and the return associated with measure performance. Measures associated with other entities can be included in this layer. This capability enables the use of the difference between the subject measure and the measures of other entities as measures;

7. A layer that optionally defines the relationship of one or more of the first six layers of entity context to one or more reference systems over time. A spatial reference coordinate system will be used for most entities. Predefined spatial reference coordinates available for use in the system of the present invention include the major organs in a human body, each of the continents, the oceans, the earth and the solar system. Virtual reference coordinate systems can also be used to relate each entity to other entities. For example, a virtual coordinate system could be a network such as the Internet, an intranet, a local are network network, a wi-fi network, a wimax network and/or social network. The genome of different entities can also be used as a reference coordinate system. This layer may also be subdivided into any number of sub-layers along user specified dimensions and would identify system or application context if appropriate;

8. A layer that defines and describes the lexicon of the subject—this layer may be broken into sub-layers to define the lexicon associated with each of the previous context layers.

Different combinations of context layers from different subjects and/or entities are relevant to different analyses and decisions. For simplicity, we will generally refer to eight types of context layers or eight context layers while recognizing that the number of context layers can be greater or less than eight. It is worth noting at this point that the layers may be combined for ease of use, to facilitate processing and/or as entity requirements dictate. Before moving on to discuss context frames—which are defined by one or more entity function and/or mission measures and the portion of each of the eight context layers that impacts the one or more entity function and/or mission measures—we need to define each context layer in more detail. Before we can do this, we need to define key terms that we will use in more fully defining the Personalized Medicine Service (100) of the present invention:

1. Entity type—any member or combination of members of a hierarchy or group (see Tables 1, 2 and 3 for examples of hierarchies and groups);
2. Entity—a discrete unit of an entity type that has one or more functions, these functions can support the completion of a mission;
3. Context—defines and describes the situation of an entity vis a vis the drivers of subject function performance as shown in FIG. 2A, FIG. 2B or FIG. 2C. It includes but is not limited to the data, information and knowledge that defines and describes the eight context layers identified previously for a valid context space;
4. User context—defines and describes the users situation vis a vis drivers of user function performance—note: user may or may not be the subject;
5. Subject—patient (900), combination of patients (925) or a patient—entity system (950) as shown in FIG. 2A, FIG. 2B or FIG. 2C respectively with one or more defined functions;
6. Function—behavior or performance of the subject, can include creation, production, growth, improvement, destruction, diminution and/or maintenance of a component of context and/or one or more entities. Examples: maintaining body temperature at 98.6 degrees Fahrenheit, destroying cancer cells, improving muscle tone and producing insulin;
7. Mission—what an entity intends to do or achieve (i.e. a goal), functions can support the completion of an entity mission;

8. Characteristic—numerical or qualitative indication of entity status—examples: temperature, color, shape, distance weight, and cholesterol level (descriptive data are the typical source of data about characteristics) and the acceptable range for these characteristics (aka a subset of constraints);
9. Event—something that takes place in a defined point in space time, the events of interest are generally those that are recorded and have an impact on the components of context and/or measure performance of a subject and/or change the characteristics of an entity;
10. Project—action or series of actions that produces one or more lasting changes. Change can include: changes a characteristic, changes a constraint, produces one or more new components of context, changes one or more components of context, produces one or more new entities or some combination thereof. Said changes impact entity function performance/mission and are analyzed using same method, system and media described for event and extreme event analysis;
11. Action—acquisition, consumption, destruction, production or transfer of resources, elements and/or entities in a defined point in space time—examples: blood cells transfer oxygen to muscle cells and an assembly line builds a product. Actions are a subset of events and are generally completed by a process;
12. Data—anything that is recorded—includes transaction data, descriptive data, content, information and knowledge;
13. Information—data with context of unknown completeness;
14. Knowledge—data with the associated complete context—all eight types of layers are defined and complete to the extent possible given uncertainty;
15. Transaction—anything that is recorded that isn't descriptive data. Transactions generally reflect events and/or actions for one or more entities over time (transaction data are generally the source);
16. Measure—quantitative indication of one or more subject functions and/or missions—examples: cash flow, patient survival rate, bacteria destruction percentage, shear strength, torque, cholesterol level, and pH maintained in a range between 6.5 and 7.5;
17. Element—also known as a context element these are tangible and intangible entities that participate in and/or support one or more subject actions and/or functions without normally being consumed by the action—examples: land, heart, Sargasso sea, relationships, wing and knowledge;
18. Element combination—two or more elements that share performance drivers to the extent that they need to be analyzed as a single element;
19. Item—an item is an instance within an element. For example, an individual salesman would be an "item" within the sales department element (or entity). In a similar fashion a gene would be an item within a dna entity. While there are generally a plurality of items within an element, it is possible to have only one item within an element;
20. Item variables are the transaction data and descriptive data associated with an item or related group of items;
21. Indicators (also known as item performance indicators and/or factor performance indicators) are data derived from data related to an item or a factor;
22. Composite variables for a context element or element combination are mathematical combinations of item variables and/or indicators, logical combinations of item variables and/or indicators and combinations thereof;
23. Element variables or element data are the item variables, indicators and composite variables for a specific context element or sub-context element;
24. Subelement—a subset of all items in an element that share similar characteristics;
25. Asset—subset of elements that support actions and are usually not transferred to other entities and/or consumed—examples: brands, customer relationships, information and equipment;
26. Agent—subset of elements that can participate in an action. Six distinct kinds of agents are recognized—initiator, negotiator, closer, catalyst, regulator, messenger. A single agent may perform several agent functions—examples: customers, suppliers and salespeople;
27. Resource—entities that are routinely transferred to other entities and/or consumed—examples: raw materials, products, information, employee time and risks;
28. Subresource—a subset of all resources that share similar characteristics;
29. Process—combination of elements actions and/or events that are used to complete an action or event—examples: sales process, cholesterol regulation and earthquake. Processes are a special class of element;
30. Commitment—an obligation to complete a transaction in the future—example: contract for future sale of products and debt;
31. Competitor—subset of factors, an entity that seeks to complete the same actions as the subject, competes for elements, competes for resources or some combination thereof;
32. Priority—relative importance assigned to actions and measures;
33. Requirement—minimum or maximum levels for one or more elements, element characteristics, actions, events, processes or relationships, may be imposed by user (40), laws (1306) or physical laws (i.e. force=mass times acceleration);
34. Surprise—variability or events that improve or increase subject performance;
35. Risk—variability or events that reduce or degrade subject performance;
36. Extreme risk—caused by variability or extreme events that reduce subject performance by producing permanent changes in the impact of one or more components of context on the subject;
37. Critical risk—extreme risks that can terminate a subject;
38. Competitor risk—risks that are a result of actions by an entity that competes for resources, elements, actions or some combination thereof;
39. Factor—entities external to subject that have an impact on subject performance—examples: commodity markets, weather, earnings expectation—as shown in FIG. 2A factors are associated with subjects that are outside the box. All higher levels in the hierarchy of a subject are also defined as factors.
40. Composite factors are numerical indicators of: external entities that influence performance, conditions external to the subject that influence performance, conditions of the entity compared to external expectations of entity conditions or the performance of the entity compared to external expectations of entity performance;
41. Factor variables are the transaction data and descriptive data associated with context factors;

42. Factor performance indicators (also known as indicators) are data derived from factor related data;
43. Composite factors (also known as composite variables) for a context factor or factor combination are mathematical combinations of factor variables and/or factor performance indicators, logical combinations of factor variables and/or factor performance indicators and combinations thereof;
44. External Services (9) are services available from systems that are not part of the system of the present invention (100) via a network (wired or wireless) connection. They include search services (google, yahoo!, etc.), map services (mapquest, yahoo!, etc.), rating services (zagat's, fodor's, etc.), weather services and services particular to a location or site (projection services, presence detection services, voice transcription services, traffic status reports, tour guide information, etc.);
45. A layer is software and/or information that gives an application, system, service, device or layer the ability to interact with another layer, device, system, service, application or set of information at a general or abstract level rather than at a detailed level;
46. Context frames include all information relevant to function measure performance for a defined combination of context layers, subject and subject functions. In one embodiment, each context frame is a series of pointers that are stored within a separate table;
47. Complete context is a shorthand way of noting that all eight types of context layers have been defined for an subject function (note: it is also used as a proprietary trade-name designation for applications or services with a context quotient of 200);
48. Complete Entity Context—complete context for all entity functions;
49. Components of Context—any combination of location (901), projects (902), events (903), virtual location (904), factors (905), resources (906, elements (907), actions (908), transactions (909), function measures (910), processes (911), mission measures (912), constraints (913), preferences (914) and factors (1000, 2000 and 3000) that have a relationship to and/or impact on a subject;
50. Contextbase is a database that organizes data and information by context for one or more subject entities. In one embodiment the contextbase is a virtual database. The contextbase can also be a relational database, a flat database, a storage area network and/or some combination thereof;
51. Total risk is the sum of all variability risks and event risks for a subject.
52. Variability risk is a subset of total risk. It is the risk of reduced or impaired performance caused by variability in one or more components of context. Variability risk is quantified using statistical measures like standard deviation. The covariance and dependencies between different variability risks are also determined because simulations use quantified information regarding the interrelationship between the different risks to perform effectively;
53. Event risk is a subset of total risk. It is the risk of reduced or impaired performance caused by the occurrence of an event. Event risk is quantified by combining a forecast of event frequency with a forecast of event impact on subject components of context and the entity itself;
54. Contingent liabilities are a subset of event risk where the impact of an event occurrence is known;
55. Uncertainty measures the amount of subject function measure performance that cannot be explained by the components of context and their associated risk that have been identified by the system of the present invention. Sources of uncertainty include model error and data error.
56. Real options are defined as options the entity may have to make a change in its behavior/performance at some future date—these can include the introduction of new elements or resources, the ability to move processes to new locations, etc. Real options are generally supported by the elements of an entity;
57. The efficient frontier is the curve defined by the maximum function and/or mission measure performance an entity can expect for a given level of total risk; and
58. Services are self-contained, self-describing, modular pieces of software that can be published, located, queried and/or invoked across a World Wide Web, network and/or a grid. In one embodiment all services are SOAP compliant. Bots and agents can be functional equivalents to services. In one embodiment all applications are services, However, the system of the present invention can function using: bots (or agents), client server architecture, and integrated software application architecture and/or combinations thereof.

We will use the terms defined above and the keywords that were defined previously when detailing one embodiment of the present invention. In some cases key terms may be defined by the Upper Ontology or an industry organization such as the Plant Ontology Consortium, the Gene Ontology Consortium or the ACORD consortium (for insurance). In a similar fashion the Global Spatial Data Infrastructure organization and the Federal Geographic Data Committee are defining a reference model for geographic information that can be used to define the spatial reference standard for geographic information. The United Nations is similarly defining the United Nations Standard Product and Services Classification which can also be used for reference. The element definitions, descriptive data, lexicon and reference frameworks from these sources can supplement or displace the pre-defined metadata included within the contextbase (50) as appropriate. Because the system of the present invention identifies and quantifies the impact of different actions, constraints, elements, events, factors, preferences, processes, projects, risks and resources as part of its normal processing, the relationships defined by standardized ontologies are generally not utilized. However, they can be used as a starting point for system processing and/or to supplement the results of processing.

In any event, we can now use the key terms to better define the eight types of context layers and identify the typical source for the data and information as shown below.

1. The element context layer identifies and describes the entities that impact subject function and/or mission measure performance by time period. The element description includes the identification of any sub-elements and preferences. Preferences may be important characteristics for process elements that have more than one option for completion. Elements are initially identified by the chosen subject hierarchy (elements associated with lower levels of a hierarchy are automatically included) whereas transaction data identifies others as do analysis and user input. These elements may be identified by item or sub-element. The sources of data can include devices (3), narrow system databases (5), partner narrow system databases (6), external databases (7), the World Wide Web (8), external services (9), xml compliant applications, the Complete Context™ Input Service (601) and combinations thereof.
2. The resource context layer identifies and describes the resources that impact subject function and/or mission measure performance by time period. The resource description includes the identification of any sub-resources. The sources of data can include narrow system databases (5), partner narrow system databases (6), external databases (7), the World Wide Web (8), external services (9), xml compliant applications, the Complete Context™ Input Service (601) and combinations thereof.
3. The environment context layer identifies and describes the factors in the social, natural and/or physical environment that impact subject function and/or mission measure performance by time period. The relevant factors are determined via analysis. The factor description includes the identification of any sub-factors. The sources of data can include devices (3), narrow system databases (5), partner narrow system databases (6), external databases (7), the World Wide Web (8) and external services (9), xml compliant applications, the Complete Context™ Input Service (601) and combinations thereof.
4. The transaction context layers identifies and describes the events, actions, action priorities, commitments and requirements of the subject and each entity in the element context layer by time period. The description identifies the elements and/or resources that are associated with the event, action, action priority, commitment and/or requirement. The sources of data can include narrow system databases (5), partner narrow system databases (6), external databases (7), the World Wide Web (8), external services (9), xml compliant applications, the Complete Context™ Input Service (601) and combinations thereof.
5. The relationship context layer defines the relationships between the first three layers (elements, resources and/or factors) and the fourth layer (events and/or actions) by time period. These impacts can be identified by user input (i.e. process maps and procedures), analysis, narrow system databases (5), partner narrow system databases (6), external databases (7), the World Wide Web (8), external services (9), xml compliant applications, the Complete Context™ Input Service (601) and combinations thereof.
6. The measure context layer(s) identifies and quantifies the impact of actions, events, elements, factors, resources and processes (combination of elements) on each entity function measure by time period. The impact of risks and surprises can be kept separate or integrated with other element/factor measures. The impacts are generally determined via analysis. However, the analysis can be supplemented by input from simulation programs, the user (40), a subject matter expert (42) and/or a collaborator (43), narrow system databases (5), partner narrow system databases (6), external databases (7), the World Wide Web (8), external services (9), xml compliant applications, the Complete Context™ Input Service (601) and combinations thereof.
7. Reference context layer (optional)—the relationship of the first six layers to a specified real or virtual coordinate system. These relationships can be identified by user input (i.e. maps), input from a subject matter expert (42) and/or a collaborator (43), narrow system databases (5), partner narrow system databases (6), external databases (7), the World Wide Web (8), external services (9), xml compliant applications, the Complete Context™ Input Service (601), analysis and combinations thereof; and
8. Lexical context layer—defines the terminology used to define and describe the components of context in the other seven layers. These lexicon can be identified by user input, input from a subject matter expert (42) and/or a collaborator (43), narrow system databases (5), partner narrow system databases (6), external databases (7), the World Wide Web (8), external services (9), xml compliant applications, the Complete Context™ Input Service (601), analysis and combinations thereof.

The eight context layers define a complete context for entity performance for a specified function by time period. We can use the more precise definition of context to define what it means to be knowledgeable. Our revised definition would state that an individual that is knowledgeable about a subject has information from all eight context layers for the one or more functions he, she or it is considering. This is important because, once the complete context is known and modeled any disease can be managed and/or cured. The knowledgeable individual would be able to use the information from the eight context layers to:

1. identify the range of contexts where models of subject function performance are applicable; and
2. accurately predict subject actions in response to events and/or actions in contexts where the context is applicable.

The accuracy of the prediction created using the eight types of context layers reflects the level of knowledge. For simplicity we will use the R squared ($R^2$) statistic as the measure of knowledge level. $R^2$ is the fraction of the total squared error that is explained by the model—other statistics can be used to provide indications of the entity model accuracy including entropy measures and root mean squared error. The gap between the fraction of performance explained by the model and 100% is uncertainty, errors in the model and errors in the data. Table 10 illustrates the use of the information from six of the eight layers in analyzing a sample personalized medicine context.

TABLE 10

1. Mission: patient health & longevity, financial break even measures
2. Environment: malpractice insurance is increasingly costly
3. Measure: survival rate is 99% for procedure A and 98% for procedure B; treatment in first week improves 5 year survival 18%, 5 year recurrence rate is 7% higher for procedure A
4. Relationship: Dr. X has a commitment to assist on another procedure Monday
5. Resource: operating room A time available for both procedures
6. Transaction: patient should be treated next week, his insurance will cover operation
7. Element: operating room, operating room equipment, Dr. X In addition to defining context, context layers are useful in developing management tools. One use of the layers is establishing budgets and/or alert levels for data within a layer or combinations of layers. Using the sample situation illustrated in Table 10, an alert could be established for survival rates that drop below 99% in the measure layer. Control can be defined and applied at the transaction and measure levels by assigning priorities to actions and measures. Using this approach the system of the present invention has the ability to analyze and optimize performance using user specified priorities, historical measures or some combination of the two.

Some analytical applications are limited to optimizing the instant (short-term) impact given the elements, resources and the transaction status. Because these systems generally ignore uncertainty and the impact, reference, environment and long term measure portions of a complete context, the recommendations they make are often at odds with common sense decisions made by line managers that have a more complete context for evaluating the same data. This deficiency is one reason some have noted that "there is no intelligence in business intelligence applications". One reason some existing systems take this approach is that the information that defines three important parts of complete context (relationship, environment and long term measure impact) are not readily available and must generally be derived. A related shortcoming of some of these systems is that they fail to identify the context or contexts where the results of their analyses are valid.

In one embodiment, the Personalized Medicine Service (100) provides the functionality for integrating data from all narrow systems (4), creating a contextbase (50), developing a Personalized Medicine Service (100) and supporting the Complete Context™ Suite (625) as shown in FIG. 13. Over time, the narrow systems (4) can be eliminated and all data can be entered directly into the Personalized Medicine Service (100) as discussed previously. In an alternate mode, the Personalized Medicine Service (100) would work in tandem with a Process Integration System (99) such as an application server, laboratory information management system, middleware application, extended operating system, data exchange or grid to integrate data, create the contextbase (50), develop a Personalized Medicine Service (100) and support the Complete Context™ Suite (625) as shown in FIG. 14. In either mode, the system of the present invention supports the development and storage of all eight types of context layers in order to create a contextbase (50).

The contextbase (50) also enables the development of new types of analytical reports including a sustainability report and a controllable performance report. The sustainability report combines the element lives, factor lives, risks and an entity context to provide an estimate of the time period over which the current subject performance level can be sustained. There are three paired options for preparing the report—dynamic or static mode, local or indirect mode, risk adjusted or pre-risk mode. In the static mode, the current element and factor mix is "locked-in" and the sustainability report shows the time period over which the current inventory will be depleted. In the dynamic mode the current element and factor inventory is updated using trended replenishment rates to provide a dynamic estimate of sustainability. The local perspective reflects the sustainability of the subject in isolation while the indirect perspective reflects the impact of the subject on another entity. The indirect perspective is derived by mapping the local impacts to some other entity. The risk adjusted (aka "risk") and pre-risk modes (aka "no risk") are self explanatory as they simply reflect the impact of risks on the expected sustainability of subject performance. The different possible combinations of these three options define eight modes for report preparation as shown in Table 11.

TABLE 11

| Mode | Static or Dynamic | Local or Indirect | Risk or No Risk |
|---|---|---|---|
| 1 | Static | Local | Risk |
| 2 | Static | Local | No Risk |
| 3 | Static | Indirect | Risk |
| 4 | Static | Indirect | No Risk |
| 5 | Dynamic | Local | Risk |
| 6 | Dynamic | Local | No Risk |
| 7 | Dynamic | Indirect | Risk |
| 8 | Dynamic | Indirect | No Risk |

The sustainability report reflects the expected impact of all context elements and factors on subject performance over time. It can be combined with the Complete Context™ Forecast Service (603), described below, to produce unbiased reserve estimates. Context elements and context factors are influenced to varying degrees by the subject. The controllable performance report identifies the relative contribution of the different context elements and factors to the current level of entity performance. It then puts the current level of performance in context by comparing the current level of performance with the performance that would be expected if some or all of the elements and factors were all at the mid-point of their normal range—the choice of which elements and factors to modify could be a function of the control exercised by the subject. Both of these reports are pre-defined for display using the Complete Context™ Review Service (607) described below.

The Complete Context™ Review Service (607) and the other services in the Complete Context™ Suite (625) use context frames and sub-context frames to support the analysis, forecast, review and/or optimization of entity performance. Context frames and sub-context frames are created from the information provided by the Personalized Medicine Service (100) created by the system of the present invention (100). The ID to frame table (165) identifies the context frame(s) and/or sub-context frame(s) that will be used by each user (40), manager (41), subject matter expert (42), and/or collaborator (43). This information is used to determine which portion of the Personalized Medicine Service (100) will be made available to the devices (3) and narrow systems (4) that support the user (40), manager (41), subject matter expert (42), and/or collaborator (43) via the Complete Context™ API (application program interface). As detailed later, the system of the present invention can also use other methods to provide the required context information.

Context frames are defined by the entity function and/or mission measures and the context layers associated with the entity function and/or mission measures. The context frame provides the data, information and knowledge that quantifies the impact of actions, constraints, elements, events, factors, preferences, processes, projects, risks and resources on entity performance. Sub-context frames contain information relevant to a subset of one or more function measure/layer combinations. For example, a sub-context frame could include the portion of each of the context layers that was related to an entity process. Because a process can be defined by a combination of elements, events and resources that produce an action, the information from each layer that was associated with the elements, events, resources and actions that define the process would be included in the sub-context frame for that process. This sub-context frame would provide all the information needed to understand process performance and the impact of events, actions, element change and factor change on process performance.

The services in the Complete Context™ Suite (625) are "context aware" (with context quotients equal to 200) and have the ability to process data from the Personalized Medicine Service (100) and its contextbase (50). Another novel feature of the services in the Complete Context™ Suite (625) is that they can review entity context from prior time periods to generate reports that highlight changes over time and display the range of contexts under which the results they produce are valid. The range of contexts where results are valid will be hereinafter be referred to as the valid context space.

The services in the Complete Context™ Suite (625) also support the development of customized applications or services. They do this by:

1. providing ready access to the internal logic of the service while at the same time protecting this logic from change; and
2. using the universal context specification (see FIG. 17) to define standardized Application Program Interfaces (API's) for all Complete Context™ Services—these API's allow the specification of the different context layers using text information, numerical information and/or graphical representations of subject context in a format similar to that shown in FIG. 2A, FIG. 2B, and FIG. 2C.

The first features allow users (40), partners and external services to get information tailored to a specific context while preserving the ability to upgrade the services at a later date in an automated fashion. The second feature allows others to incorporate the Complete Context™ Services into other applications and/or services. It is worth noting that this awareness of context is also used to support a true natural language interface (714)—one that understands the meaning of the identified words—to each of the services in the Suite (625). It should be also noted that each of the services in the Suite (625) supports the use of a reference coordinate system for displaying the results of their processing when one is specified for use by the user (40). The software for each service in the suite (625) resides in an applet or service with the context frame being provided by the Personalized Medicine Service (100). This software could also reside on the computer (110) with user access through a browser (800) or through the natural language interface (714) provided by the Personalized Medicine Service (100). Other features of the services in the Complete Context™ Suite (625) are briefly described below:

1. Complete Context™ Analysis Service (602)—analyzes the impact of user (40) specified changes on a subject for a given context frame or sub-context frame by mapping the proposed change to the appropriate context layer(s) in accordance with the schema or ontology and then evaluating the impact of said change on the function and/or mission measures. Context frame information may be supplemented by simulations and information from subject matter experts (42) as appropriate. This service can also be used to analyze the impact on changes on any "view" of the entity that has been defined and pre-programmed for review. For example, accounting profit using three different standards or capital adequacy can be analyzed using the same rules defined for the Complete Context™ Review Service (607) to convert the context frame analysis to the required reporting format.
2. Complete Context™ Auditing Service (624)—is a modified Complete Context™ Review Service (607) that uses a rules engine to completely re-process all relevant transactions and compare the resulting values with the information in a report presented by management. The Complete Context™ Auditing Service then combines this information with the information stored in the Context Base (50) to complete an automated audit of all the numbers in a report—including reserve estimates—as well as producing a list of risk factors in order of importance. After the various calculations are completed, the system of the present invention produces a discrepancy report where the reported values in a report is compared to the value computed using the method and system detailed above.
3. Complete Context™ Bridge Service (624)—is a service that identifies the differences between two context frames and the best mode for bringing the frames into alignment or congruence. This service can be very useful in breaking down barriers to communication and facilitating negotiations.
4. Complete Context™ Browser (628)—supports browsing through the contextbase (50) with a focus on one or more dimensions of the Universal Context Specification for the user (40) and/or a subject.
5. Complete Context™ Capture and Collaboration Service (622)—guides one or more subject matter experts (42) and/or collaborators (43) through a series of steps in order to capture information, refine existing knowledge and/or develop plans for the future using existing knowledge. The one or more subject matter experts (42) and/or collaborators (43) will provide information and knowledge by selecting from a template of pre-defined elements, resources, events, factors, actions and entity hierarchy graphics that are developed from the subject schema table (157). The one or more subject matter experts (42) and/or collaborators (43) also have the option of defining new elements, events, factors, actions and hierarchies. The one or more subject matter experts (42) and/or collaborators (43) are first asked to define what type of information and knowledge will be provided. The choices will include each of the eight types of context layers as well as element definitions, factor definitions, event definitions, action definition, impacts, processes, uncertainty and scenarios. On this same screen, the one or more subject matter experts (42) and/or collaborators (43) will also be asked to decide whether basic structures or probabilistic structures will provided in this session, if this session will require the use of a time-line and if the session will include the lower level subject matter. The selection regarding type of structures will determine what type of samples will be displayed on the next screen. If the use of a time-line is indicated, then the user will be prompted to: select a reference point—examples would include today, event occurrence, when I started, etc.; define the scale being used to separate different times—examples would include seconds, minutes, days, years, light years, etc.; and specify the number of time slices being specified in this session. The selection regarding which type of information and knowledge will be provided determines the display for the last selection made on this screen. There is a natural hierarchy to the different types of information and knowledge that can be provided by a one or more subject matter experts (42) and/or collaborators (43). For example, measure level knowledge would be expected to include input from the impact, element, transaction and resource context layers. If the one or more subject matter experts (42) and/or collaborators (43) agrees, the service will guide the one or more subject matter experts (42) and/or collaborators (43) to provide knowledge for each of the "lower level" knowledge areas by following the natural hierarchies. Summarizing the preceding discussion, the one or more subject matter experts (42) and/or collaborators (43) has used the first screen to select the type of information and knowledge to be provided (measure layer, impact layer, transaction layer, resource layer, environment layer, element layer, reference layer, event risk or scenario). The one or more subject matter experts (42) and/or collaborators (43) has also chosen to provide this information in one of four formats: basic structure without timeline, basic structure with timeline, relational structure without timeline or relational structure with timeline. Finally, the one or more subject matter experts (42) and/or collaborators (43) has indicated whether or not the session will include an extension to capture "lower level" knowledge. Each selection made by the one or more subject matter experts (42) and/or collaborators (43) will be used to identify the combination of elements, events, actions, factors and entity hierarchy chosen for display and possible selection. This information will be displayed in a manner that is somewhat similar to the manner in which stencils are made available to Visio® users for use in the workspace. The next screen displayed by the service will depend on which combination of information, knowledge, structure and timeline selections that were made by the one or more subject matter experts (42) and/or collaborators (43). In addition to displaying the sample graphics to the one or more subject matter experts (42) and/or collaborators (43), this screen will also provide the one or more subject matter experts (42) and/or collaborators (43) with the option to use graphical operations to change impacts, define new impacts, define new elements, define new factors and/or define new events. The thesaurus table (164) in the contextbase (50) provides graphical operators for: adding an element or factor, acquiring an element, consuming an element, changing an element, factor or event risk values, adding a impact, changing the strength of a impact, identifying an event cycle, identifying a random impact, identifying commitments, identifying constraints and indicating preferences. The one or more subject matter experts (42) and/or collaborators (43) would be expected to select the structure that most closely resembles the knowledge that is being communicated or refined and add it to the workspace being displayed. After adding it to the workspace, the one or more subject matter experts (42) and/or collaborators (43) will then edit elements, factors, resources and events and add elements, factors, resources events and descriptive information in order to fully describe the information or knowledge being captured from the context frame represented on the screen. If relational information is being specified, then the one or more subject matter experts (42) and/or collaborators (43) will be given the option of using graphs, numbers or letter grades to communicate the information regarding probabilities. If a timeline is being used, then the next screen displayed will be the screen for the same perspective from the next time period in the time line. The starting point for the next period knowledge capture will be the final version of the knowledge captured in the prior time period. After completing the knowledge capture for each time period for a given level, the Service (622) will guide the one or more subject matter experts (42) and/or collaborators (43) to the "lower level" areas where the process will be repeated using samples that are appropriate to the context layer or area being reviewed. At all steps in the process, the information in the contextbase (50) and the knowledge collected during the session will be used to predict elements, resources, actions, events and impacts that are likely to be added or modified in the workspace. These "predictions" are displayed using flashing symbols in the workspace. The one or more subject matter experts (42) and/or collaborators (43) is given with the option of turning the predictive prompting feature off. After the information and knowledge has been captured, the graphical results are converted to data base entries and stored in the appropriate tables (141, 142, 143, 144, 145, 149, 154, 156, 157, 158, 162 or 168) in the contextbase (50). Data from simulation programs can also be added to the contextbase (50) to provide similar information or knowledge. This Service (622) can also be used to verify the veracity of some new assertion by mapping the new assertion to the subject model and quantifying any reduction in explanatory power and/or increase in uncertainty of the entity performance model.

6. Complete Context™ Customization Service (621)—service for analyzing and optimizing the impact of data, information, products, projects and/or services by customizing the features included in or expressed by an offering for a subject for a given context frame or sub-context frame. The context frame or sub-context frame may be provided by the Complete Context™ Summary Service (617). Some of the products and services that can be customized with this service include medicine, medical treatments, medical tests, software, technical support, equipment, computer hardware, devices, services, telecommunication equipment, living space, buildings, advertising, data, information and knowledge. Other customizations may rely on the Complete Context™ Optimization Service (604) working alone or in combination with the Complete Context™ Search Service (609). Context frame information may be supplemented by simulations and information from subject matter experts (42) as appropriate.

7. Complete Context™ Display Service (614)—manages the availability and display of data, information, and knowledge related to one or more context frames and/or sub context frames to a user (40), manager (41), subject matter expert (42), and/or collaborator (43) on a continuous basis using a portal (11), service (9), device (3), computer (110) and/or other display. To support this effort the Complete Context™ Display Service (614) supports RSS feeds, manages one or more caches (119) that support projections and display(s) utilizing the caches and/or data feeds. The priority assigned to the data and information made available is determined via a randomized algorithm that blends frequency of use, recency of use, cost to retrieve and time to retrieve measures with a relevance measure for each of the one or more context frames and/or sub context frames being supported (see Complete Context™ Scout Service (616) for a discussion of relevance measure computation). As the user (40), manager (41), subject matter expert (42), and/or collaborator (43) context changes (for example when location changes or the World Trade Center collapses), the relevance measure will change which will in turn drive this Service (614) to change the mix in the cache, RSS feed or projection in order to ensure that data and/or information that is most relevant to the new context is readily available. This Service (614) can be combined with the Complete Context™ Optimization Service (604) to ensure that messages, emails, network traffic, computer resources and related devices are providing the optimal support for a given context. In a similar fashion it can be combined with the Complete Context™ Capture and Collaboration Service (622) to ensure that the one or more subject matter experts (42) and/or collaborators (43) have the data, information and knowledge they need to complete their input to the system of the present invention. The service can be used to purge data, information and knowledge that is no longer relevant to the given context. In an interactive commerce setting this application can be used to: identify the content that is most relevant to a customer's context and/or display an ad or technical support information relevant to said context. In this same setting it can be combined with other services in the suite (625) complete a sale using the Complete Context™ Exchange Service (608), purchase content that has a value in excess of its cost in the current context using the Complete Context™ Exchange Service (608), customize and buy an offering using the Complete Context™ Customization Service (621) in conjunction with the Complete Context™ Exchange Service (608), and/or customize and sell an offering using the Complete Context™ Customization Service (621) in conjunction with the Complete Context™ Exchange Service (608).

8. Complete Context™ Exchange Service (608)—identifies desirable exchanges of resources, elements, commitments, data and information with other entities in an automated fashion. This service calls on Complete Context™ Analysis Service (602) in order to review proposed prices. In a similar manner the service calls on the Complete Context™ Optimization Service (604) to determine the optimal parameters for an exchange before completing a transaction. For partners or customers that provide access to their data that is sufficient to define a shared context, the exchange service can use the other services from the Complete Context™ Suite (625) to analyze and optimize the exchange for the combined parties. The actual transactions are completed by the Complete Context™ Input Service (601).

9. Complete Context™ Forecast Service (603)—forecasts the value of specified variable(s) using data from all relevant context layers. Completes a tournament of forecasts for specified variables and defaults to a multivalent combination of forecasts from the tournament using methods similar to those first described in cross referenced U.S. Pat. No. 5,615,109. In addition to providing the forecast, this service will provide the confidence interval associated with the forecast and provide the user (40) with the ability to identify the data that needs to be collected in order improve the confidence associated with a given forecast which will make the process of refining forecasts more efficient.

10. Complete Context™ Indexing Service (619)—service for developing composite and covering indices for data, information and knowledge in contextbase (50) using the impact cutoff and node depth specified by the user (40) in the system settings table (162) for contexts and combination of contexts.

11. Complete Context™ Input Service (601)—service for recording actions and commitments into the contextbase (50). The interface for this service is a template accessed via a browser (800) or the natural language interface (714) provided by the Medicine Service (100) that identifies the available element, transaction, resource and measure data for inclusion in a transaction. After the user has recorded a transaction the service saves the information regarding each action or commitment to the contextbase (50). Other services such as Complete Context™ Analysis (602), Planning (605) or Optimization (604) Services can interface with this service to generate actions, commitments and/or transactions in an automated fashion. Complete Context™ Bots (650) can also be programmed to provide this functionality.

12. Complete Context™ Journal Service (630) (aka the "daily me")—uses natural language generation to automatically develop and deliver a prioritized summary of news and information in any combination of formats covering a specified time period (hourly, daily, weekly, etc.) that is relevant to a given subject context or context frame. Relevance is determined in a manner identical to that described previously for the Complete Context™ Scout Service (616) save for the fact that the user (40) is free to modify the node depth, subject entity definition and/or impact cutoff used for evaluating relevance using a wizard.

13. Complete Context™ Metrics and Rules Service (611)—tracks and displays the causal performance indicators for context elements, resources and factors for a given context frame as well as the rules used for segmenting context components into smaller groups for more detailed analysis. Rules and patterns can be discovered using an algorithm tournament that includes the Apriori algorithm, the sliding window algorithm; differential association rule mining, beam-search, frequent pattern growth and decision trees.

14. Complete Context™ Optimization Service (604)—simulates entity performance and identifies the optimal mix of actions, events and/or context components for operating a specific context frame or sub context frame given the constraints, uncertainty and the defined function and/or mission measures. A tournament is used to select the best algorithm from the group consisting of genetic algorithms, the calculus of variations, constraint programming, game theory, mixed integer linear programming, multi-criteria maximization, linear programming, semi-definite programming, smoothing and highly optimized tolerance. Because most entities have more than one function (and more than one measure), the genetic algorithm and multi-criteria maximizations are used most frequently. This service can also be used to optimize Complete Context™ Review Service (607) measures using the same rules defined for the Complete Context™ Review Service (607) to define context frames in the required format before optimization.

15. Complete Context™ Planning Service (605)—service that is used to: establish measure priorities, establish action priorities, and establish expected performance levels (aka budgets) for actions, events, elements resources and measures. These priorities and performance level expectations are saved in the corresponding layer in the contextbase (50). For example, measure priorities are saved in the measure layer table (145). This service also supports collaborative planning when context frames that include one or more partners are created (see FIG. 2B).

16. Complete Context™ Profiling Service (615)—service for developing the best estimate of complete entity context from available subject related data and information. If a complete context has been developed for a similar entity, then the Complete Context™ Profiling Service (615) will identify: the portion of behavior that is generally explained by the level of detail in the profile, differences from the similar entity, expected ranges of behavior and sources of data that are generally used to produce a more complete context before completing an analysis of the available data. The contexts developed by this service (615) can be used to.

17. Complete Context™ Project Service (606)—service for analyzing and optimizing the impact of a project or a group of projects on a context frame. Project is broadly defined to include any development or diminution of any components of context and/or entities. Context frame information may be supplemented by simulations and information from subject matter experts (42) as appropriate.
18. Complete Context™ Review Service (607)—service for reviewing components of context and measures alone or in combination. These reviews can be completed with or without the use of a reference layer. This service uses a rules engine to transform contextbase (50) historical information into standardized reports that have been defined by different entities. Other standardized, non-financial performance reports have been developed for medical entities, military operations and educational institutions. The sustainability and controllable performance reports described previously are also pre-defined for calculation and display. The rules engine produces each of these reports on demand for review and optional publication.
19. Complete Context™ Scout Service (616)—service that works with the Complete Context™ Indexing Service (619) to proactively identify data, information and/or knowledge regarding choices the subject will be making in the near future using the time frame or time frames defined by user (40) in system settings table (162). The Complete Context™ Scout (616) uses process maps, preferences and the Complete Context™ Forecast Service (603) to identify the choices that it expects the subject to make in the near future. It then uses weight of evidence/satisfaction algorithms including banburismus to determine which choices need additional data, information and/or knowledge to support an informed decision within parameters selected by the user (40) in the system settings table (162). It of course, also determines which choices are already supported by sufficient data, information and/or knowledge. The relative priority given to the data, information and/or knowledge selected by the Complete Context™ Scout (616) is a blended function of the relevance rankings produced by several measures of relevance including ontology alignment measures, semantic alignment measures, cover density rankings, vector space model measurements, okapi similarity measurements, node rankings (as described in U.S. Pat. No. 6,285,999, which is incorporated herein by reference) which can be obtained from Google, three level relevance scores and hypertext induced topic selection algorithm scores. The relevance measure detailed in cross referenced application Ser. No. 10/237,021 can also be used to identify relevance. The Complete Context™ Scout Service (616) evaluates relevance by utilizing the relationships and impacts that define a complete entity context to the node depth and impact cutoff specified by the user in the system settings table (162) as the basis for scoring using the techniques outlined above. The node depth identifies the number of node connections that are used to identify components of context to be considered in determining the relevance score. For example, if a single entity (as shown in FIG. 2A) was expected to need information about a resource (906) and a node depth of one had been selected, then the relevance rankings would consider the components of context that are linked to resources by a single link. Using this approach data, information and/or knowledge that contains and/or is closely linked to a similar mix of context components will receive a higher ranking. As shown in FIG. 2A, this would include locations (901), projects (902), events (903), virtual locations (904), elements (907), actions (908), transactions (909) and processes (911) that had an impact greater than or equal to the impact cutoff. The Complete Context™ Scout Service (616) has the ability to use word sense disambiguation algorithms to clarify the terms being selected for search, normalizes the terms selected for search using the Porter Stemming algorithm or an equivalent and uses collaborative filtering to learn the combination of ranking methods that are generally preferred for identifying relevant data, information and/or knowledge given the choices being faced by the subject for each context and/or context frame.

20. Complete Context™ Search Service (609)—service for locating the most relevant data, information, services and/or knowledge for a given context frame or sub context frame in one of two modes—direct or indirect. In the direct mode, the relevant data, information and/or services are identified and presented to the user (40). In the indirect mode, candidate data, information and/or services are identified using publicly available search engine results that are re-analyzed before presentation to the user (40). This service can be combined with the Complete Context™ Customization Service (621) to identify and provide customized ads and/or other information related to a given context frame as relevance increases (through movement relative to a reference frame, external changes, etc.). Relevance is determined in a manner identical to that described previously for the Complete Context™ Scout (616) save for the fact that the user (40) is free to modify the node depth, subject definition and/or impact cutoff used for evaluating relevance using a wizard. Any indices associated with the revised subject definitions would automatically be changed by the Complete Context™ Index Service (619) as required to support the changed definition. The user (40) could choose to change the subject definition for any number of reasons. For example, he or she may wish to focus on only one entity context for a vertical search. Another reason for changing the definition would be to incorporate one or more contexts from other entities in a new definition. For example, an employee could choose to search for information relevant to a combination of one or more of his or her contexts (for example, his or her employee context) and one or more contexts of the employer/company (for example, the context of his project or division). As part of its processing, the Complete Context™ Search Engine (609) identifies the relationship between the requested information and other information by using the relationships and measure impacts identified in the contextbase (50). It uses this information to display the related data and/or information in a graphical format similar to the formats used in FIG. 2A, FIG. 2B and/or FIG. 2C. Again, the node depth cutoff is used to determine how "deep" into the graph the search is performed. The user (40) has the option of focusing on any block in a graphical summary of relevant information using the Complete Context™ Browser (628), for example the user (40) could choose to retrieve information about the resources (906) that support an entity (900). As discussed previously (see definitions), the subject may not be the user (40). If this is the case, then the user's context is considered as part of normal processing. Information obtained from the natural language interface (714) could be part of this context;
21. Complete Context™ Summary Service (617)—develops a summary of entity context using the Universal Context Specification (see FIG. 17) in an rdf format that contains the portion of the specification approved for release by the user (40) for use by other applications, services and/or entities. For example, the user (40) could send a summary of two contexts (family member and church-member) to a financial planner for use in establishing a portfolio that will help the user (40) realize his or her goals with respect to these two contexts. This Complete Context™ Summary can be used by others providing goods, services and information (such as other search engines) to tailor their offerings to the portion of context that has been revealed.
22. Complete Context™ Underwriting Service (620)—analyzes a context frame or sub-context frame for an entity in order to: evaluate entity liquidity, evaluate entity creditworthiness, evaluate entity risks and/or complete valuations. It can then use this information to support the: transfer of liquidity to or from said entity, transfer of risks to or from said entity, securitization one or more entity risks, underwriting of entity related securities, packaging of entity related securities into funds or portfolios with similar characteristics (i.e. sustainability, risk, uncertainty equivalent, value, etc.) and/or package entity related securities into funds or portfolios with dissimilar characteristics (i.e. sustainability, risk, uncertainty equivalent, value, etc.). As part of securitizing entity risks the Complete Context™ Underwriting Service (620) identifies an uncertainty equivalent for the risks being underwritten. This innovative analysis combines quantified uncertainty by type with the securitized risks to give investors a more complete picture of the risk they are assuming when they buy a risk security. All of these analyses can rely on the measure layer information stored in the contextbase (50), the sustainability reports, the controllable performance reports and any pre-defined review format. Context frame information may be supplemented by simulations and information from subject matter experts as appropriate.

The services within the Complete Context™ Suite (625) can be combined in any combination and/or joined together in any combination in order to complete a specific task. For example, the Complete Context™ Review Service (607), the Complete Context™ Forecast Service (603) and the Complete Context™ Planning Service (605) can be joined together to process a series of calculations. The Complete Context™ Analysis Service (602) and the Complete Context™ Optimization Service (604) are also joined together frequently to support performance improvement activities. In a similar fashion the Complete Context™ Optimization Service (604) and the Complete Context™ Capture and Collaboration Service (622) are often combined to support knowledge transfer and simulation based training. The services in the Complete Context™ Suite (625) will hereinafter be referred to as the standard services or the services in the Suite (625).

The Personalized Medicine Service (100) utilizes a novel software and system architecture for developing the complete entity context used to support entity related systems and services. Narrow systems (4) generally try to develop and use a picture of how part of an entity is performing (i.e. supply chain, heart functionality, etc.). The user (40) is then left with an enormous effort to integrate these different pictures—often developed from different perspectives—to form a complete picture of entity performance. By way of contrast, the Personalized Medicine Service (100) develops complete pictures of entity performance for every function using a common format (i.e. see FIG. 2A, FIG. 2B and FIG. 2C) before combining these pictures to define the complete entity context and a contextbase (50) for the subject. The detailed information from the complete entity context is then divided and recombined in a context frame or sub-context frame that is used by the standard services in any variety of combinations for analysis and performance management.

The contextbase (50) and entity contexts are continually updated by the software in the Personalized Medicine Service (100). As a result, changes are automatically discovered and incorporated into the processing and analysis completed by the Personalized Medicine Service (100). Developing the complete picture first, instead of trying to put it together from dozens of different pieces can allow the system of the present invention to reduce IT infrastructure complexity by orders of magnitude while dramatically increasing the ability to analyze and manage subject performance. The ability to use the same software services to analyze, manage, review and optimize performance of entities at different levels within a domain hierarchy and entities from a wide variety of different domains further magnifies the benefits associated with the simplification enabled by the novel software and system architecture of the present invention.

The Personalized Medicine Service (100) provides several other important features, including:
1. the system learns from the data which means that it supports the management of new aspects of entity performance as they become important without having to develop a new system;
2. the user is free to specify any combination of functions and measures for analysis; and
3. support for the automated development and use of bots and other independent software applications (such as services) that can be used to, among other things, initiate actions, complete actions, respond to events, seek information from other entities and provide information to other entities in an automated fashion.

To illustrate the use of the Personalized Medicine Service (100), a description of the use of the services in the Complete Context™ Suite (625) to support a small clinic (an organization entity) in treating a patient (an organism entity that becomes an element of the clinic entity) will be provided. The clinic has the same measures described in table 10 for a medical facility. An overview of the one embodiment of a system to support this clinic is provided in FIG. 16. The patient comes to the clinic complaining of blood in the urine. After arriving at the clinic, he fills out a form that details his medical history. After the form is filled out, the patient has his weight and blood pressure checked by an aide before seeing a doctor. The doctor reviews the patient's information, examines the patient and prescribes a treatment before moving on to see the next patient. In the narrative that follows, the support provided by the Personalized Medicine Service (100) for each step in the patient visit and the subsequent follow up will be described. The narrative assumes that the system was installed some time ago and has completed the processing used to develop a complete ontology and contextbase (50) for the clinic along with the associated process maps.

Process maps define the expected sequence and timing of events, commitments and actions as treatment progresses. If the timing or sequence of events fail to follow the expected path, then the alerts built into the tactical layer will notify designated staff (element). Process maps also identify the agents, assets and resources that will be used to support the treatment process. FIG. 15 shows a sample process map. Process maps can be established centrally in accordance with guidelines or they can be established by individual clinicians in accordance with organization policy. In all cases they are stored in the relationship layer. Before selecting a process map, the doctor could activate the Complete Context™ Analysis Service (602) to review the expected instant impacts and outcomes from different combinations of procedures and treatments that are available under the current formulary. This information could be used to support the development of a new process map (if organization policy permits this). In any event, after the doctor selects a process map for the treatment of the specified diagnosis, the associated process commitments and alerts are associated with the patient and stored in the tactical layer. The required paperwork is automatically generated by the process map and signed as required by the doctor.

If the clinic is small, the history information from the clinic can be supplemented with data provided by external sources (such as the AMA, NIH, insurance companies, HMOs, drug companies, etc.) to provide data for a sufficient population to complete the processing to establish expected ranges for the expected mix of patients and diseases.

Data entry can be completed in a number of ways for each step in the visit. The most direct route would be to use the Complete Context™ Input Service (601) or any xml compliant application (such as newer Microsoft Office and Adobe applications) with a device such as a pc or personal digital assistant to capture information obtained during the visit using the natural language interface (714) or a pre-defined form. Once the data are captured it is integrated with the contextbase (50) in an automated fashion. A paper form could be used for facilities that do not have the ability to provide pc or pda access to patients. This paper form can be transcribed or scanned and converted into an xml document where it could be integrated with the contextbase (50) in an automated fashion. If the patient has used a Personalized Medicine Service (100) that stored data related to his or her health, then this information could be communicated to the Medicine Service (100) in an automated fashion via wireless connectivity, wired connectivity or the transfer of files from the patient's Medicine Service (100) to a recordable media. Recognizing that there are a number of options for completing data entry we will simply say that "data entry is completed" when describing each step.

Step 1—the patient details prior medical history and data entry is completed. Because the patient is new, a new element for the patient will automatically be created within the ontology and contextbase (50) for the clinic. The medical history will be associated with the new element for the patient in the element layer. Any information regarding insurance will be tagged and stored in the tactical layer which would determine eligibility by communicating with the appropriate insurance provider. The measure layer will in turn use this information to determine the expected margin and/or generate a flag if the patient is not eligible for insurance.

Step 2—weight and blood pressure are checked by an aide and data entry is completed. The medical history data are used to generate a list of possible diagnoses based on the proximity of the patient's history to previously defined disease clusters and pathways by the analytics that support the instant impact and outcome layers. Any data that is out of the normal range for the cluster will be flagged for confirmation by the doctor. The Personalized Medicine Service (100) would also query external data providers to see if the out of range data correlates with any new clusters that may have been identified since the clinic's contextbase (50) and ontology were established. The analytics in the relationship layer would then identify the tests that should be conducted to validate or invalidate possible diagnoses. Preference would be given to the tests that provide information that is relevant to the highest number of potential diagnoses for the lowest cost. If the patient's history documented the diagnostic imaging history, then consideration would also be given to cumulative radiation levels when recommending tests.

Step 3—the doctor refers the patient to a diagnostic imaging center using the process map for a pet scan (to look for tumors on the patient's kidneys). He also refers the patient for genetic testing with a new process map that assesses the patients likely response to a new type of chemotherapy.

Step 4—The images and genetic tests are completed in accordance with the specified process maps. As part of this process, the Personalized Medicine Service (101) in the imaging center highlights any probable tumors before displaying the image to the radiologist for diagnosis. The Personalized Medicine Service (102) in the genetic testing center would determine if the test array displayed the biomarkers (indicators) that indicated a likely favorable response to the new chemotherapy before having the results analyzed by a technician. In both cases the results of the analyses are sent to the Personalized Medicine Service (100) in the clinic for automated integration with the patient's medical history. At this point, the Personalized Medicine Service (100) in the clinic would automatically update the list of likely diagnoses to reflect the newly gathered information.

Step 5—the doctor reviews the information for the patient from the contextbase (50) using the Complete Context™ Review Service (607) on a device (3) such as a pda or personal computer. The doctor will have the ability to define the exact format of the display by choosing the mix of graphical and text information that will be displayed. At this point, the doctor determines that the patient probably has kidney cancer and refers the patient to a surgeon for further treatment. He activates the process map for a surgical referral, among other things this process map sends the patients medical history to the surgeon's context service system (103) in an automated fashion.

Step 6—the surgeon examines the medical records and the patient before scheduling surgery for a hospital where he has privileges. He then activates the kidney surgery process map which forwards the medical records to the hospital context service system (104).

Step 7—the surgeon completes a biopsy that confirms the presence of a malignant tumor before scheduling and completing the required surgery. After the surgery is completed, the surgeon then activates the pre-defined process map for the new chemotherapy (as noted previously, the patient's genetic biomarkers indicated that he would likely respond well to this new treatment). As information is added to the patient's medical history in the hospital context service (104), it is also communicated back to the Personalized Medicine Service (100) in the clinic for inclusion in the patient's medical history in an automated fashion and to the relevant insurance company.

Step 8—follow up. The chemotherapy process map the doctor selected is used to identify the expected sequence of events that the patient will use to complete his treatment. If the patient fails to complete an event within the specified time range or in the specified order, then the alerts built into the tactical layer will generate email messages to the doctor and/or case worker assigned to monitor the patient for follow-up and possible corrective action. Bots could be used to automate some aspects of routine follow-up like sending reminders or requests for status via email or regular mail. This functionality could also be used to collect information about long-term outcomes from patients in an automated fashion.

The process map follow-up processing continues automatically until the process ends, a clinician changes the process map for the patient or the patient visits the facility again and the process described above is repeated.

In short, the services in the Complete Context™ Suite (625) work together with the Personalized Medicine Service (100) to provide knowledgeable support to anyone trying to analyze, manage and/or optimize actions, processes and outcomes for any subject. The contextbase (50) supports the services in the Complete Context™ Suite (625) as described above. The contextbase (50) provides six important benefits:

1. By directly supporting entity performance, the system of the present invention guarantees that the contextbase (50) will provide a tangible benefit to the entity.
2. The measure focus allows the system to partition the search space into two areas with different levels of processing. Data and information that is known to be relevant to the defined functions and/or measures as well as data that are not thought to be relevant. The system does not ignore data that is not known to be relevant; however, it is processed less intensely. This information can also be used to identify data for archiving or disposal.
3. The processing completed in contextbase (50) development defines and maintains the relevant schema or ontology for the entity. This schema or ontology can be flexibly matched with other ontologies in order to interact with other entities that have organized their information using a different ontology. This functionality also enables the automated extraction and integration of data from the semantic web.
4. Defining the complete subject context allows every piece of data that is generated to be placed "in context" when it is first created. Traditional systems generally treat every piece of data in an undifferentiated fashion. As a result, separate efforts are often required to find the data, define a context and then place the data in context.
5. The contextbase (50) includes robust models of the components of context that drive action and event frequency as well as levels to vary. This capability is very useful in developing action plans to improve measure performance.
6. The focus on primary subject functions also ensures the longevity of the contextbase (50) as entity primary functions rarely change. For example, the primary function of each cell in the human body has changed very little over the last 10,000 years.

Some of the important features of the patient centric approach are summarized in Table 13.

TABLE 13

| Characteristic | Personalized Medicine Service (100) |
| --- | --- |
| Tangible benefit | Built-in |
| Computation/Search Space | Partitioned |
| Ontology development and maintenance | Automated |
| Ability to analyze new element, resource or factor | Automatic - learns from data |
| Measures in alignment | Automatic |
| Data in context | Automatic |
| Service longevity | Equal to longevity of definable measure(s) |

To facilitate its use as a tool for improving performance, the Personalized Medicine Service (100) produces reports in formats that are graphical and highly intuitive. By combining this capability with the previously described capabilities (developing context, flexibly defining robust performance measures, optimizing performance, reducing IT complexity and facilitating collaboration) the Personalized Medicine Service (100) gives individuals, groups and clinicians the tools they need to model, manage and improve the performance of any subject.

BRIEF DESCRIPTION OF DRAWINGS

These and other objects, features and advantages of the present invention will be more readily apparent from the following description of one embodiment of the invention in which:

FIG. 7A, FIG. 7B, FIG. 7C, FIG. 7D, FIG. 7E, FIG. 7F, FIG. 7G and FIG. 7H are block diagrams showing the sequence of steps in the present invention used for creating a contextbase (50) for a subject;

FIG. 8A and FIG. 8B are block diagrams showing the sequence in steps in the present invention used in propagating a Personalized Medicine Service, creating bots, services and performance reports;

FIG. 17 shows a universal context specification format.

DETAILED DESCRIPTION OF ONE PREFERRED EMBODIMENT

Figure 1:
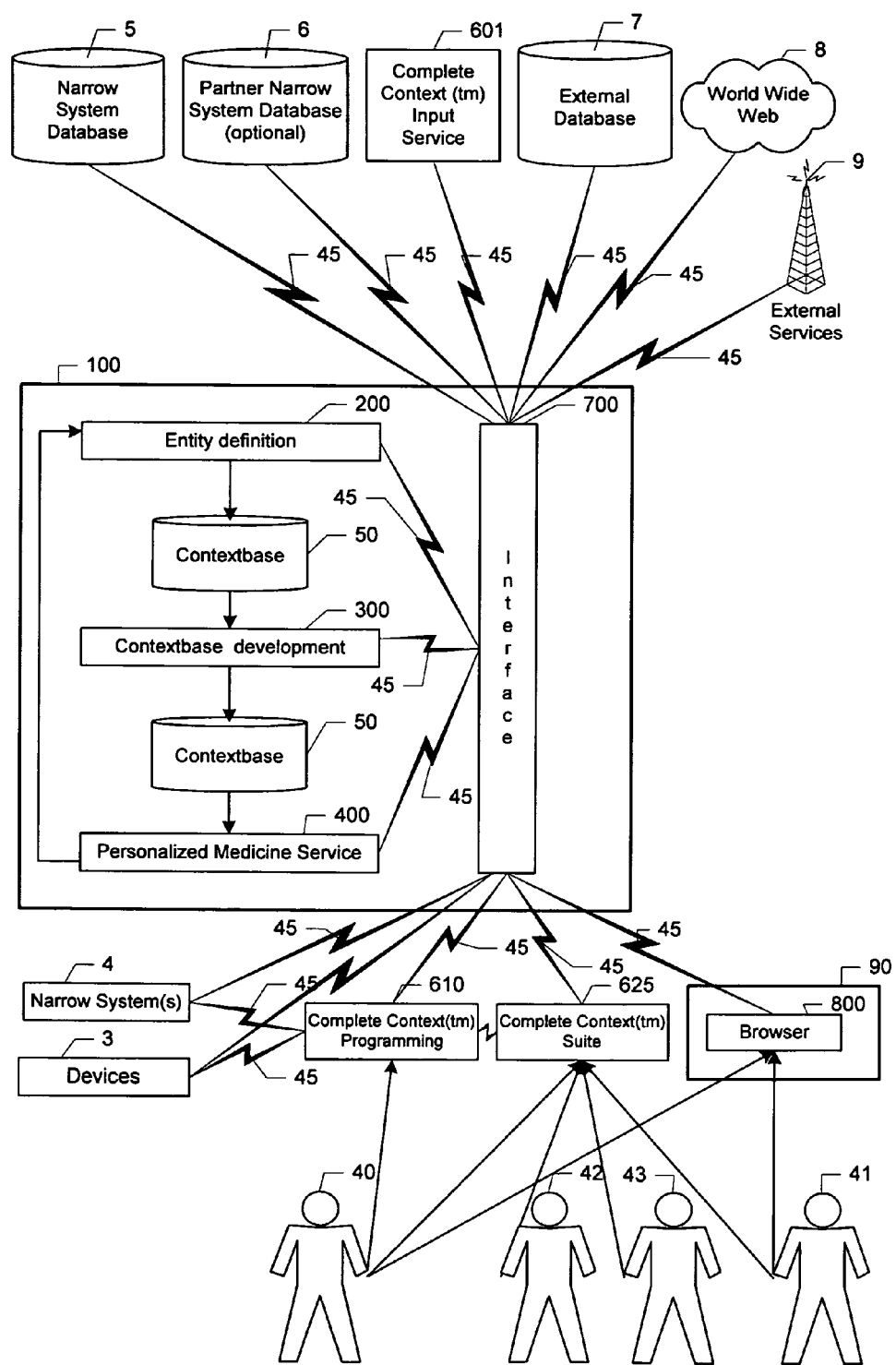
FIG. 1 is a block diagram showing the major processing steps of the present invention.
Figure 2A:
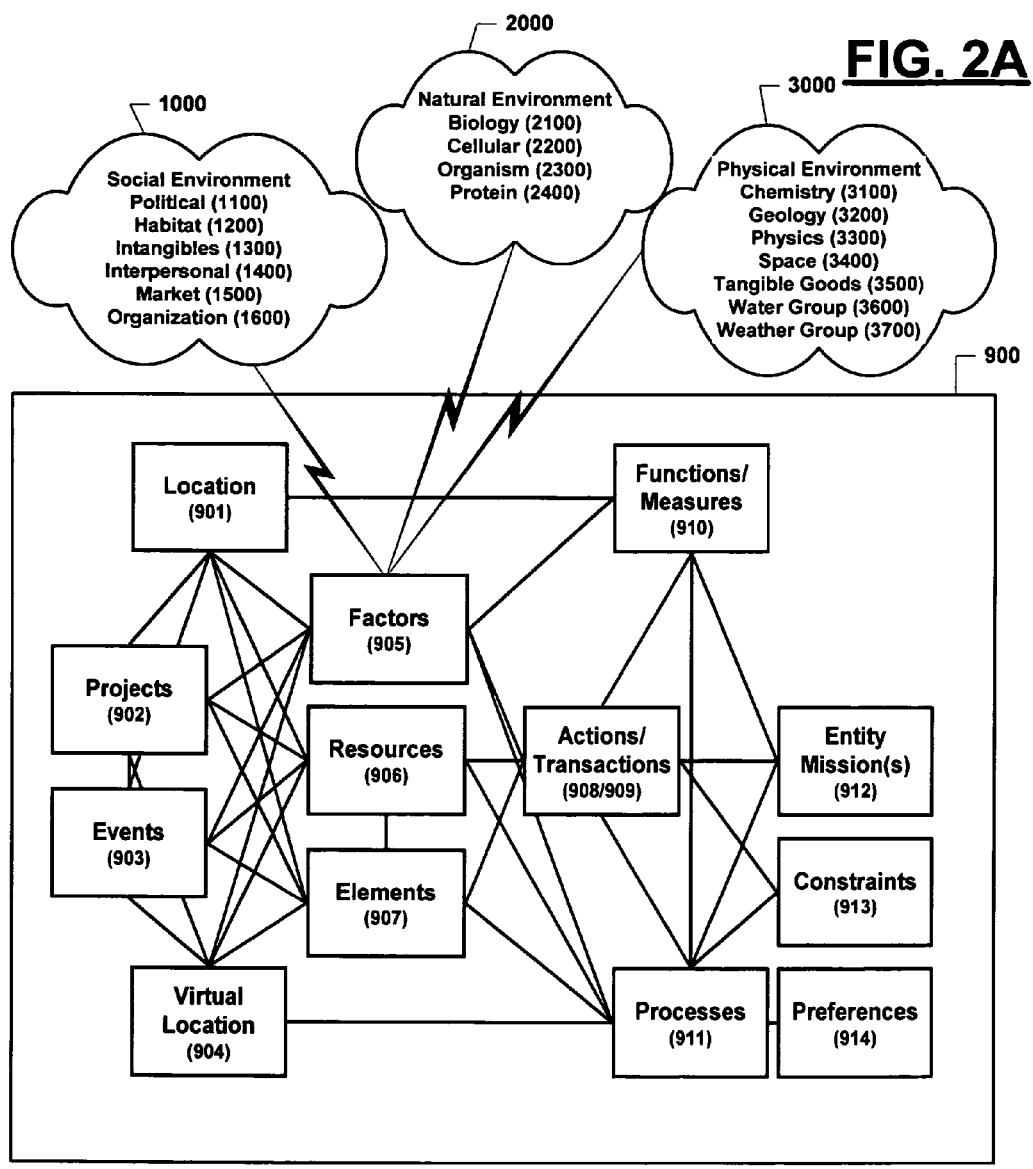
FIG. 2A, FIG. 2B and FIG. 2C are block diagrams showing a relationship between constraints, elements, events, factors, locations, measures, missions, processes and subject actions/behavior.
Figure 2B:
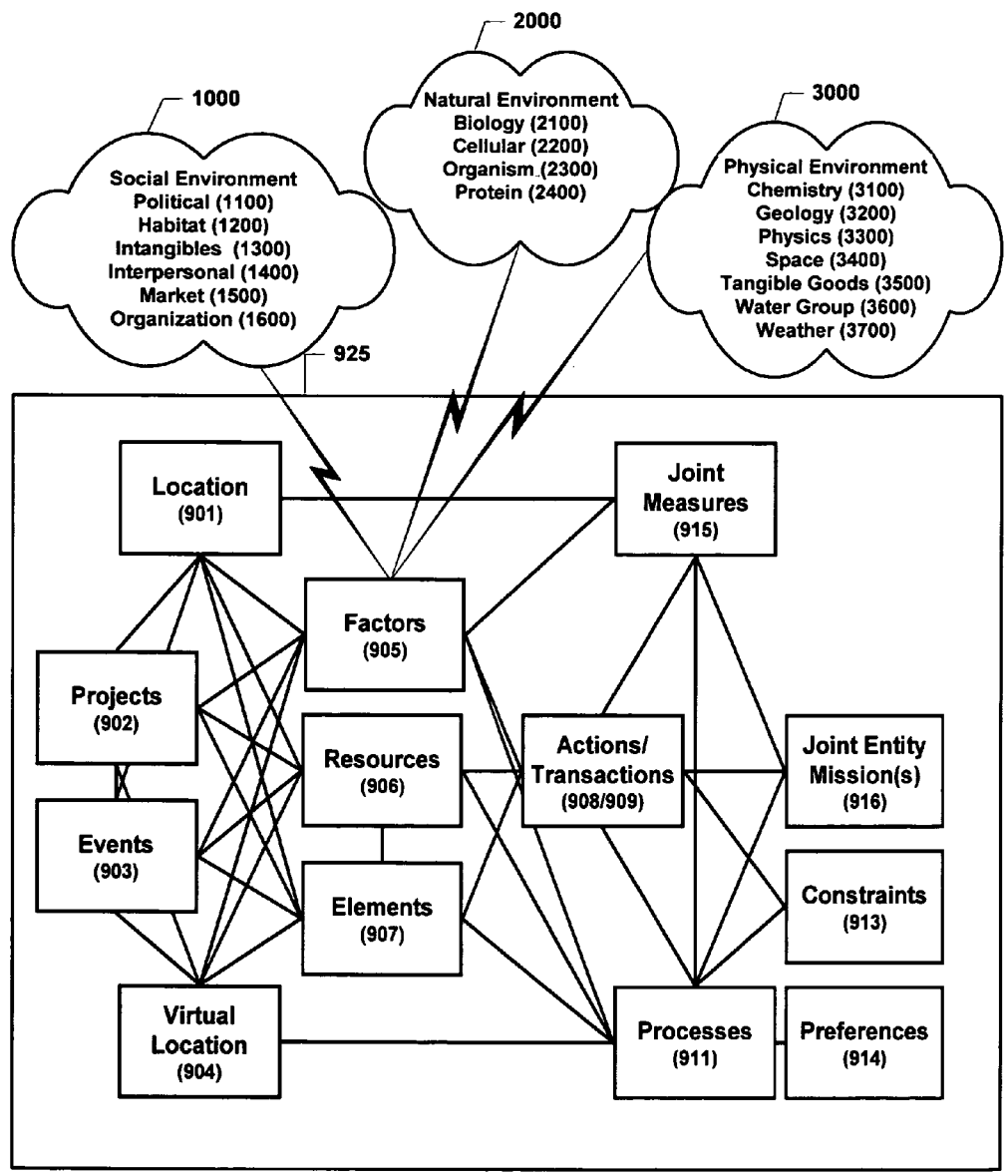
Figure 2C:
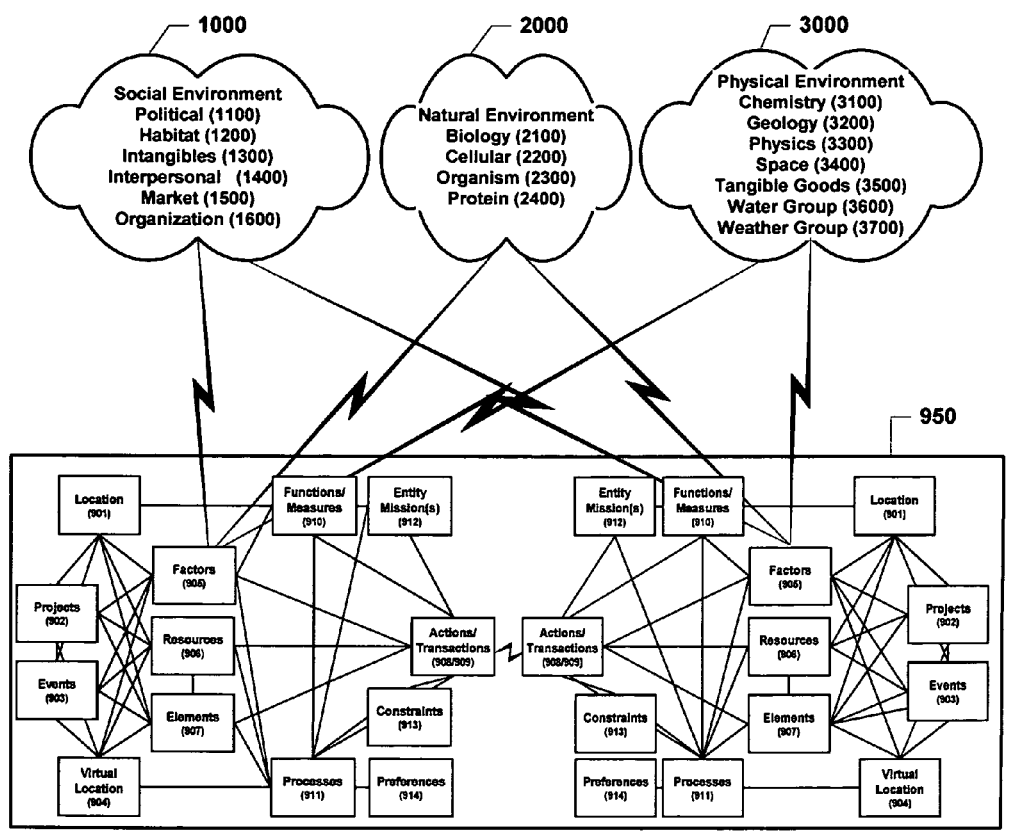
Figure 3:
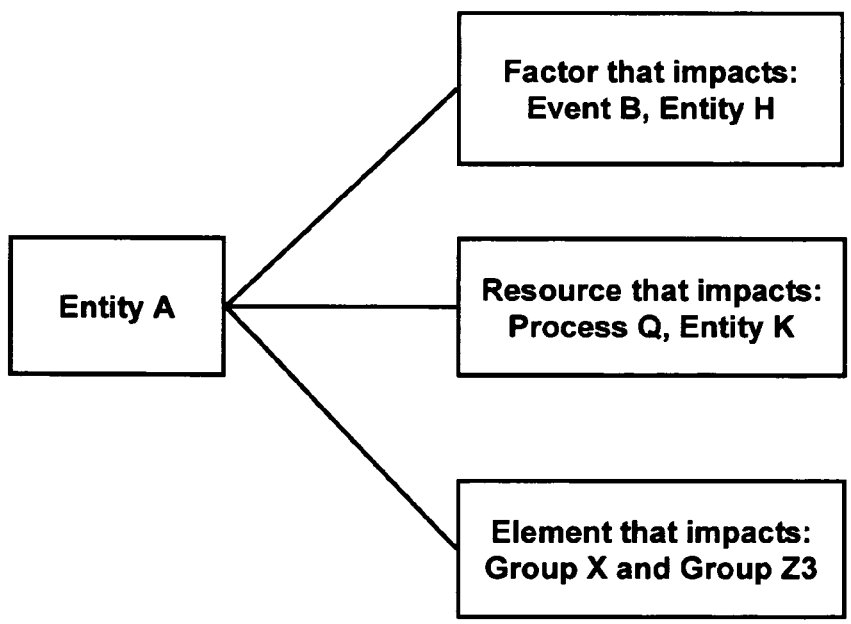
FIG. 3 shows a relationship between an entity and other entities, processes and groups.

FIG. 1 provides an overview of the processing completed by the innovative system for developing a Personalized Medicine Service (100). In accordance with the present invention, an automated system and method for developing a contextbase (50) that supports the development of a Personalized Medicine Service (100) is provided. In one preferred embodiment the contextbase (50) contains context layers for each subject measure. Processing starts in this Medicine Service (100) when the data preparation portion of the application software (200) extracts data from a narrow system database (5); an external database (7); a world wide web (8), external services (9) and optionally, a partner narrow system database (6) via a network (45). The connection to the network (45) can be via a wired connection, a wireless connection or a combination thereof. It is to be understood that the World Wide Web (8) also includes the semantic web that is being developed. Data may also be obtained from a Complete Context™ Input Service (601) or other applications that can provide xml output. For example, newer versions of Microsoft® Office and Adobe® Acrobat® can be used to provide data input to the Medicine Service (100) of the present invention.

After data are prepared, entity functions are defined and subject measures are identified, as part of contextbase (50) development in the second part of the application software (300). The contextbase (50) is then used to create a Personalized Medicine Service (100) in the third stage of processing. The processing completed by the Personalized Medicine Service (100) may be influenced by a user (40) or a manager (41) through interaction with a user-interface portion of the application software (700) that mediates the display, transmission and receipt of all information to and from the Complete Context™ Input Service (601) or browser software (800) such as the Mozilla or Opera browsers in an access device (90) such as a phone, personal digital assistant or personal computer where data are entered by the user (40). The user (40) and/or manager (41) can also use a natural language interface (714) provided by the Personalized Medicine Service (100).

While only one database of each type (5, 6 and 7) is shown in FIG. 1, it is to be understood that the Medicine Service (100) can process information from all narrow systems (4) listed in Tables 4, 5, 6 and/or 7 as well as the devices (3) listed in Table 8 for each entity being supported. In one embodiment, all functioning narrow systems (4) associated with each entity will provide data access to the Medicine Service (100) via the network (45). It should also be understood that it is possible to complete a bulk extraction of data from each database (5, 6 and 7), the World Wide Web (8) and external service (9) via the network (45) using peer to peer networking and data extraction applications. In one embodiment, the data extracted via the network (45) are tagged in a virtual database that leaves all data in the original databases where it can be retrieved and optionally converted for use in calculations by the analysis bots over a network (45). In alternate embodiments, the data could also be stored in a database, datamart, data warehouse, a cluster (accessed via GPFS), a virtual repository or a storage area network where the analysis bots could operate on the aggregated data.

Figure 4:
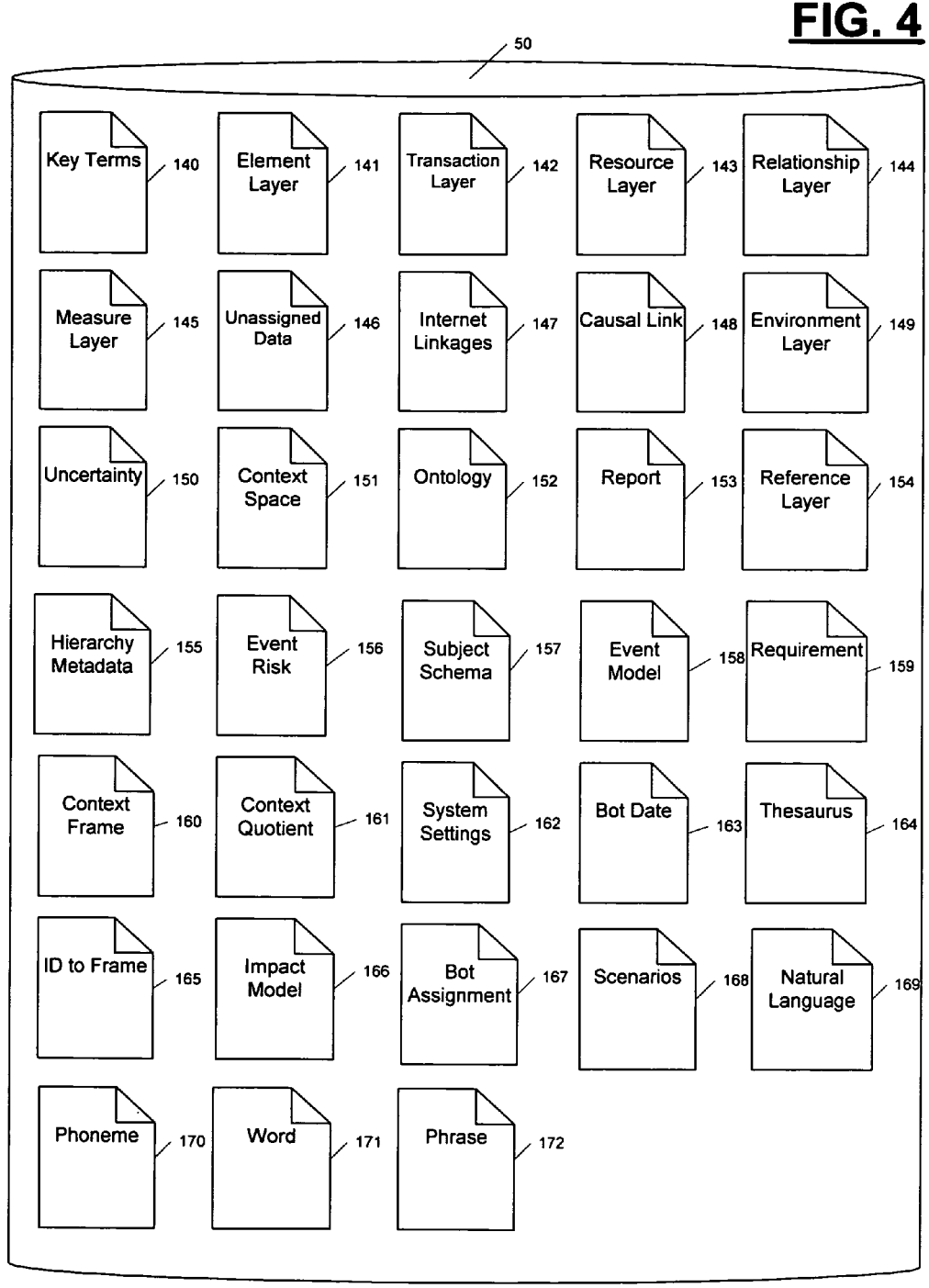
FIG. 4 is a diagram showing the tables in the contextbase (50) of the present invention that are utilized for data storage and retrieval during the processing.

The operation of the system of the present invention is determined by the options the user (40) and manager (41) specify and store in the contextbase (50). As shown in FIG. 4, the contextbase (50) contains tables for storing data by context layer including: a key terms table (140), a element layer table (141), a transaction layer table (142), an resource layer table (143), a relationship layer table (144), a measure layer table (145), a unassigned data table (146), an internet linkages table (147), a causal link table (148), an environment layer table (149), an uncertainty table (150), a context space table (151), an ontology table (152), a report table (153), a reference layer table (154), a hierarchy metadata table (155), an event risk table (156), a subject schema table (157), an event model table (158), a requirement table (159), a context frame table (160), a context quotient table (161), a system settings table (162), a bot date table (163), a Thesaurus table (164), an id to frame table (165), an impact model table (166), a bot assignment table (167), a scenarios table (168), a natural language table (169), a phoneme table (170), a word table (171) and a phrase table (172). The system of the present invention has the ability to accept and store supplemental or primary data directly from user input, a data warehouse, a virtual database, a data preparation system or other electronic files in addition to receiving data from the databases described previously. The system of the present invention also has the ability to complete the necessary calculations without receiving data from one or more of the specified databases. However, in the embodiment described herein all information used in processing is obtained from the specified data sources (5, 6, 7, 8, 9 and 601) for the subject and made available using a virtual database.

Figure 5:
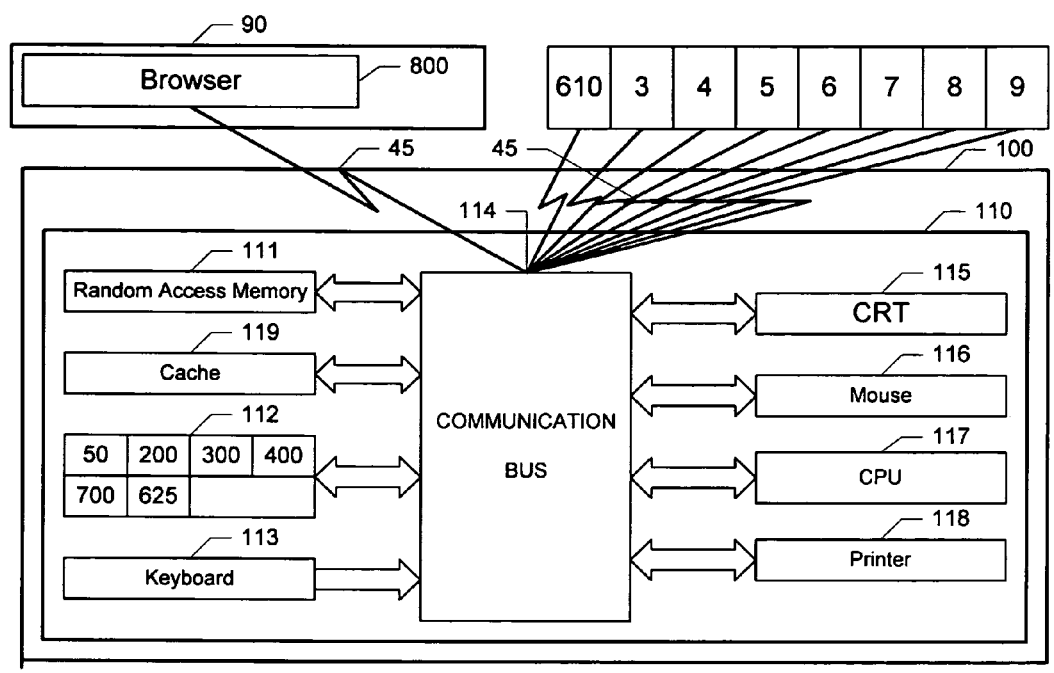
FIG. 5 is a block diagram of an implementation of the present invention.

As shown in FIG. 5, one embodiment of the present invention is a computer Medicine Service (100) illustratively comprised of a computer (110). The computer (110) is connected via the network (45) to an Internet browser appliance (90) that contains Internet software (800) such as a Mozilla browser or an Opera browser. The browser (800) will support RSS feeds.

In one embodiment, the computer (110) has a read/write random access memory (111), a hard drive (112) for storage of a contextbase (50) and the application software (200, 300, 400 and 700), a keyboard (113), a communication bus (114), a display (115), a mouse (116), a CPU (117), a printer (118) and a cache (119). As devices (3) become more capable, they be used in place of the computer (110). Larger entities may require the use of a grid or cluster in place of the computer (110) to support Complete Context™ Service processing requirements. In an alternate configuration, all or part of the contextbase (50) can be maintained separately from a device (3) or computer (110) and accessed via a network (45) or grid.

The application software (200, 300, 400 and 700) controls the performance of the central processing unit (117) as it completes the calculations used to support Complete Context™ Service development. In the embodiment illustrated herein, the application software program (200, 300, 400 and 700) is written in a combination of Java and C++. The application software (200, 300, 400 and 700) can use Structured Query Language (SQL) for extracting data from the databases and the World Wide Web (5, 6, 7 and 8). The user (40) and manager (41) can optionally interact with the user-interface portion of the application software (700) using the browser software (800) in the browser appliance (90) or through a natural language interface (714) provided by the Medicine Service (100) to provide information to the application software (200, 300, 400 and 700).

The computers (110) shown in FIG. 5 is a personal computer that is widely available for use with Linux, Unix or Windows operating systems. Typical memory configurations for client personal computers (110) used with the present invention include more than 1024 megabytes of semiconductor random access memory (111) and a hard drive (112).

Figure 6A:
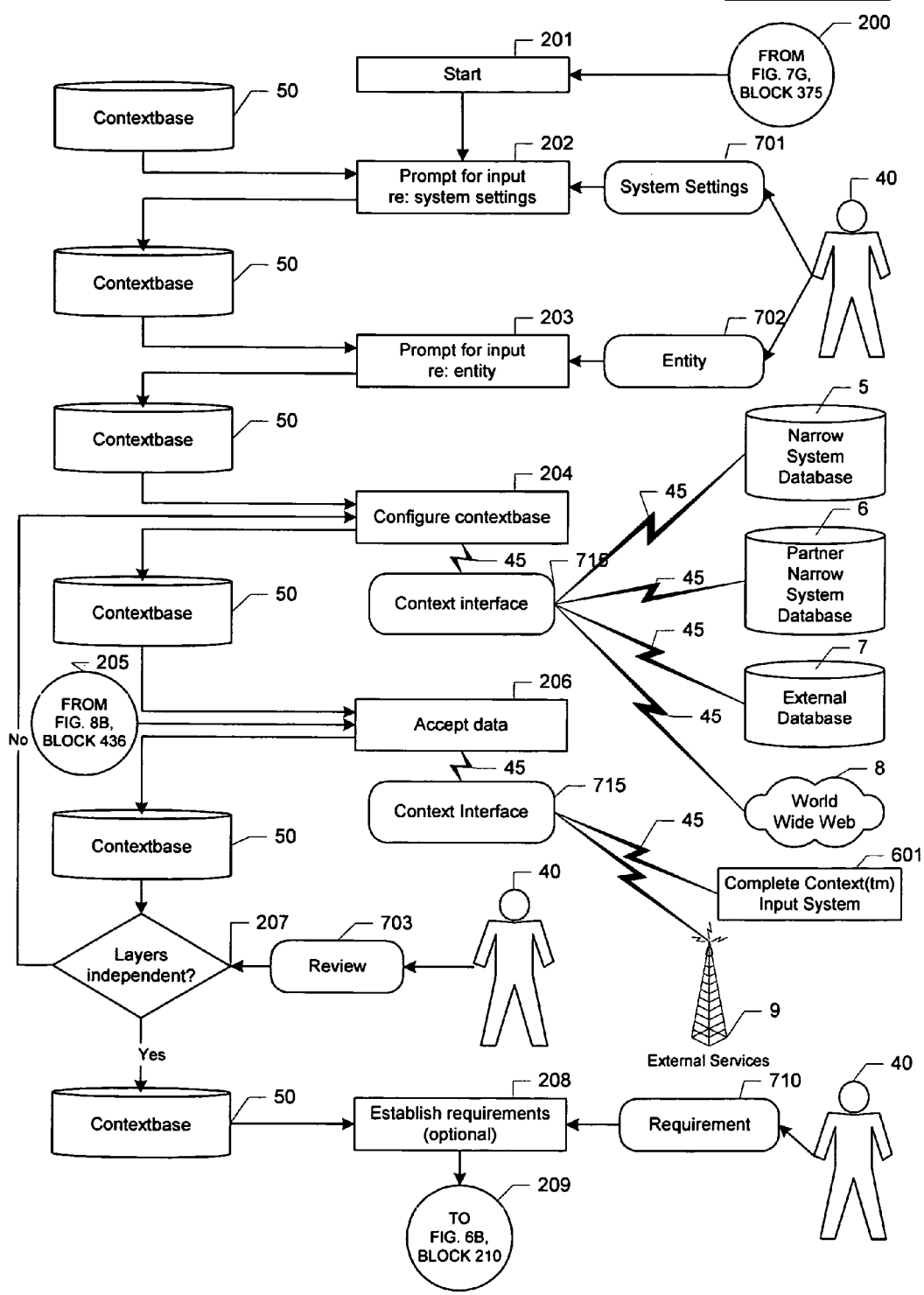
FIG. 6A, FIG. 6B and FIG. 6C are block diagrams showing the sequence of steps in the present invention used for specifying system settings, preparing data for processing and specifying the subject measures.
Figure 6B:
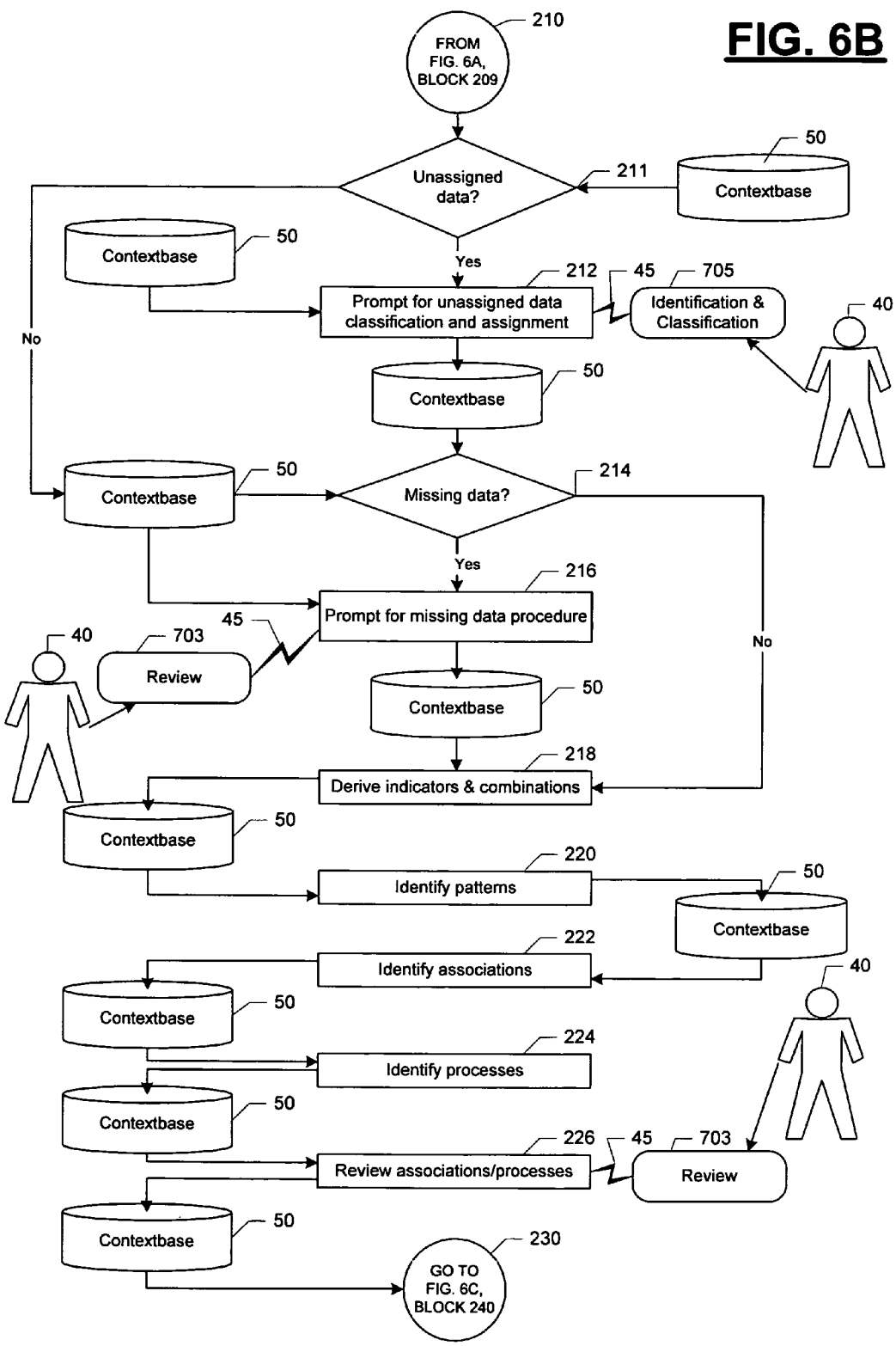
Figure 6C:
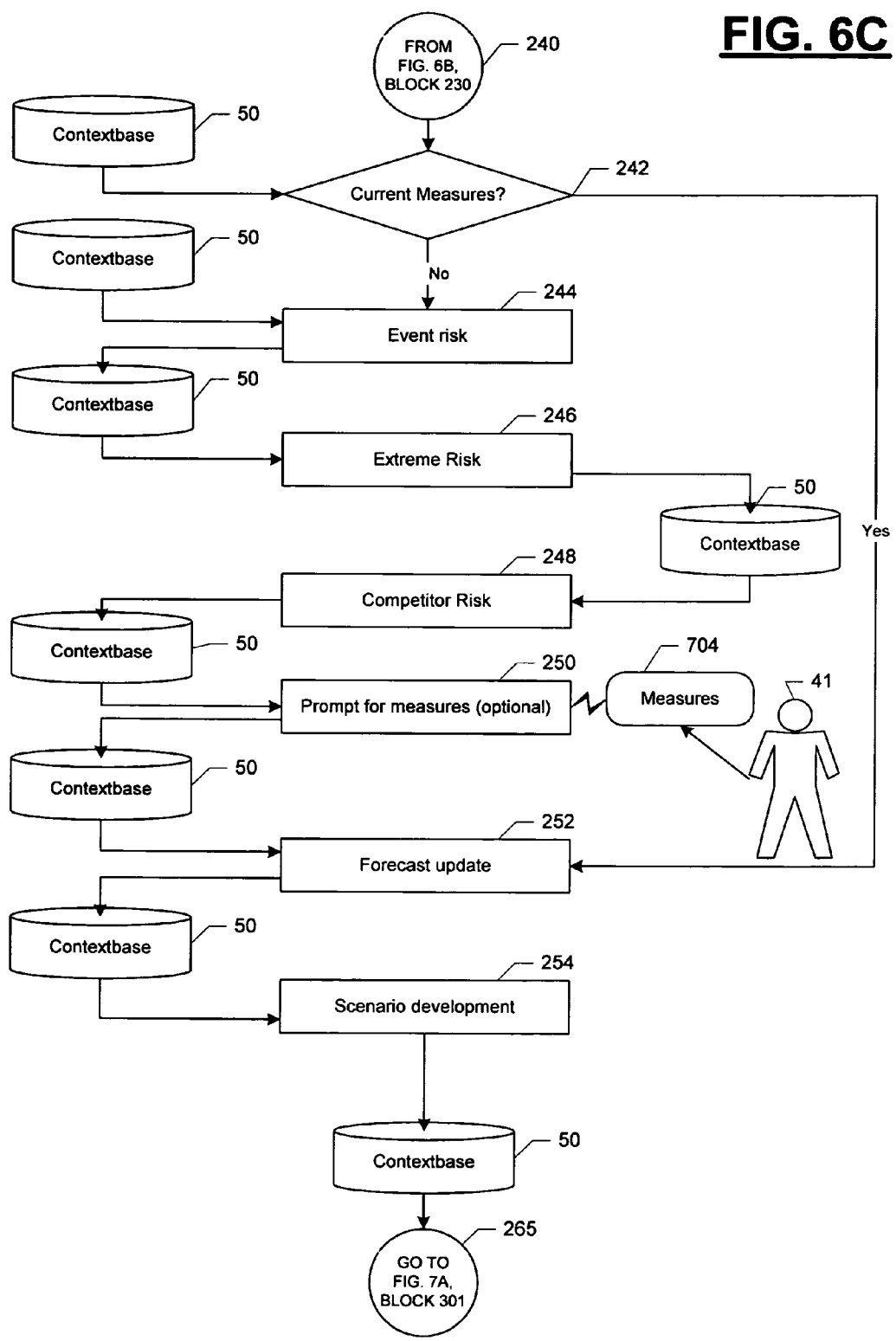
Figure 7B:
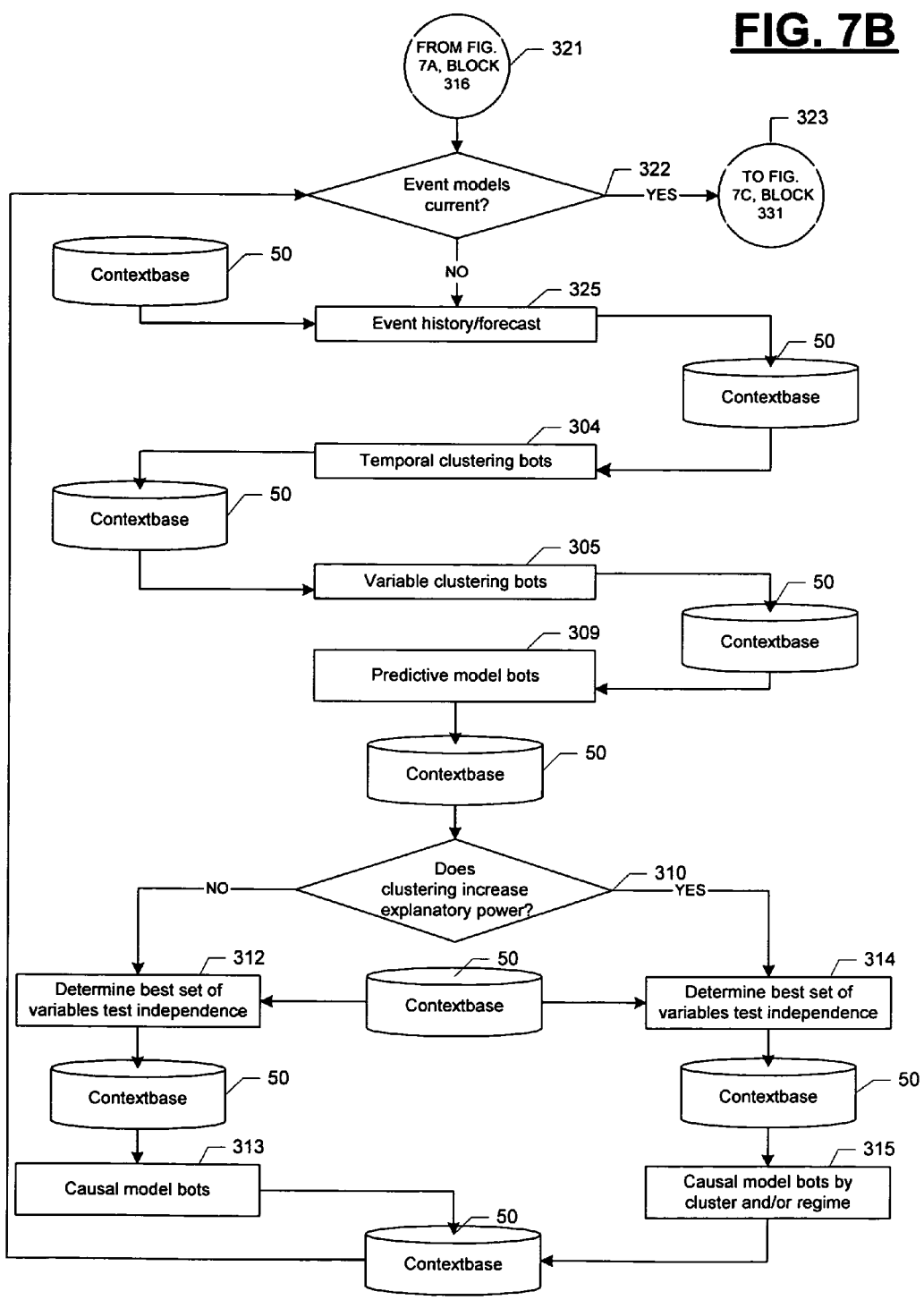
Figure 7C:
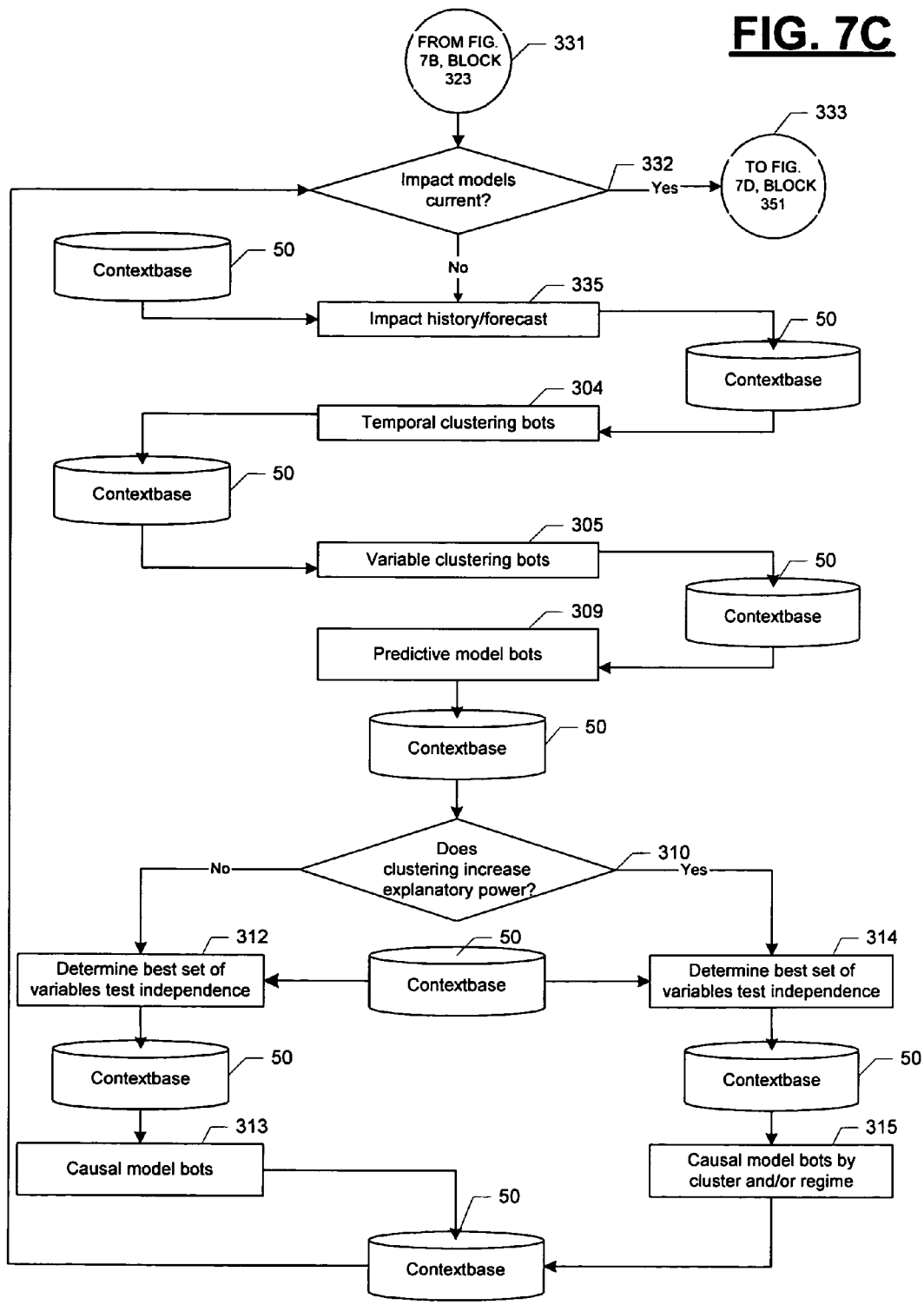
Figure 7D:
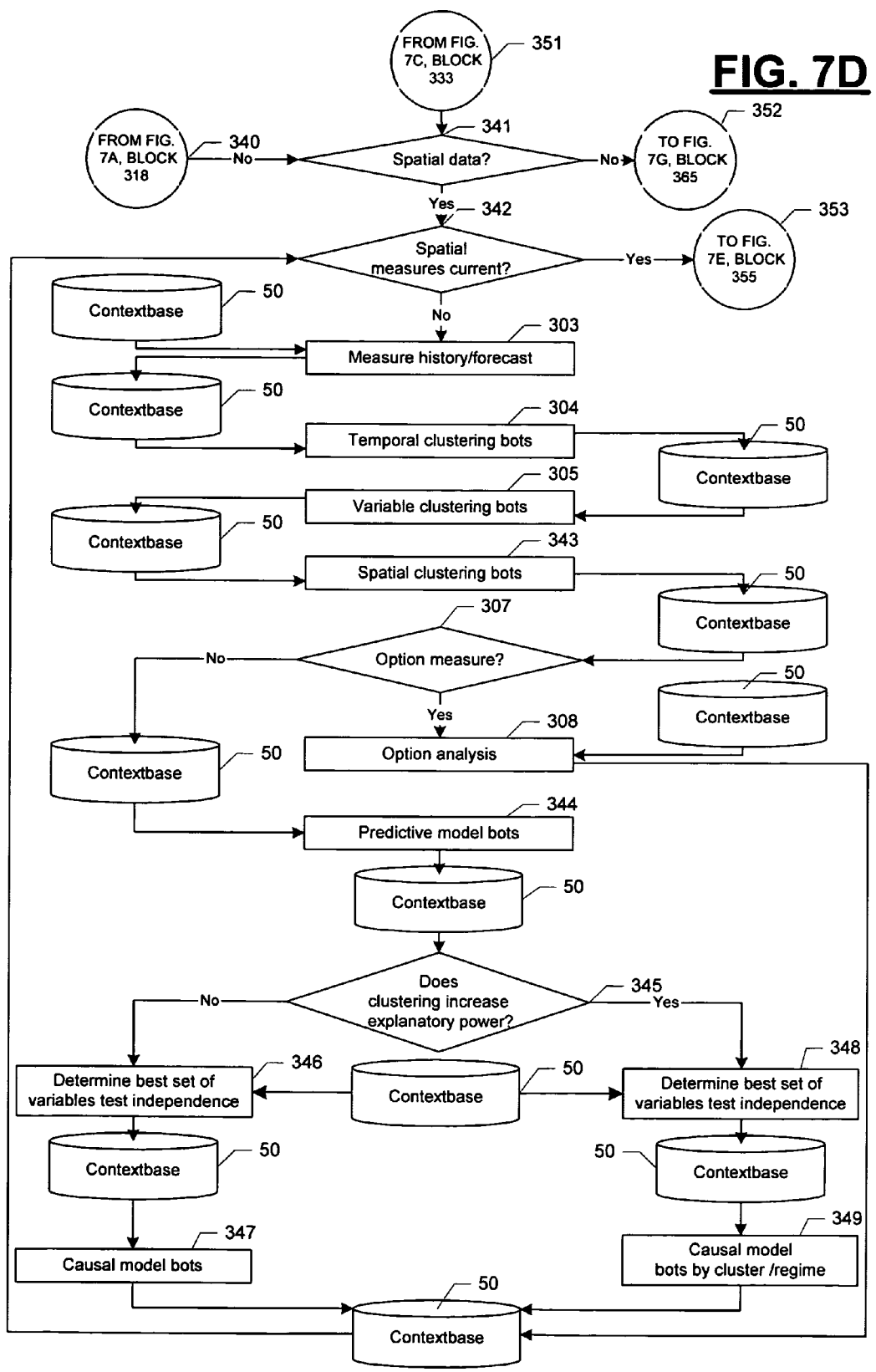
Figure 7E:
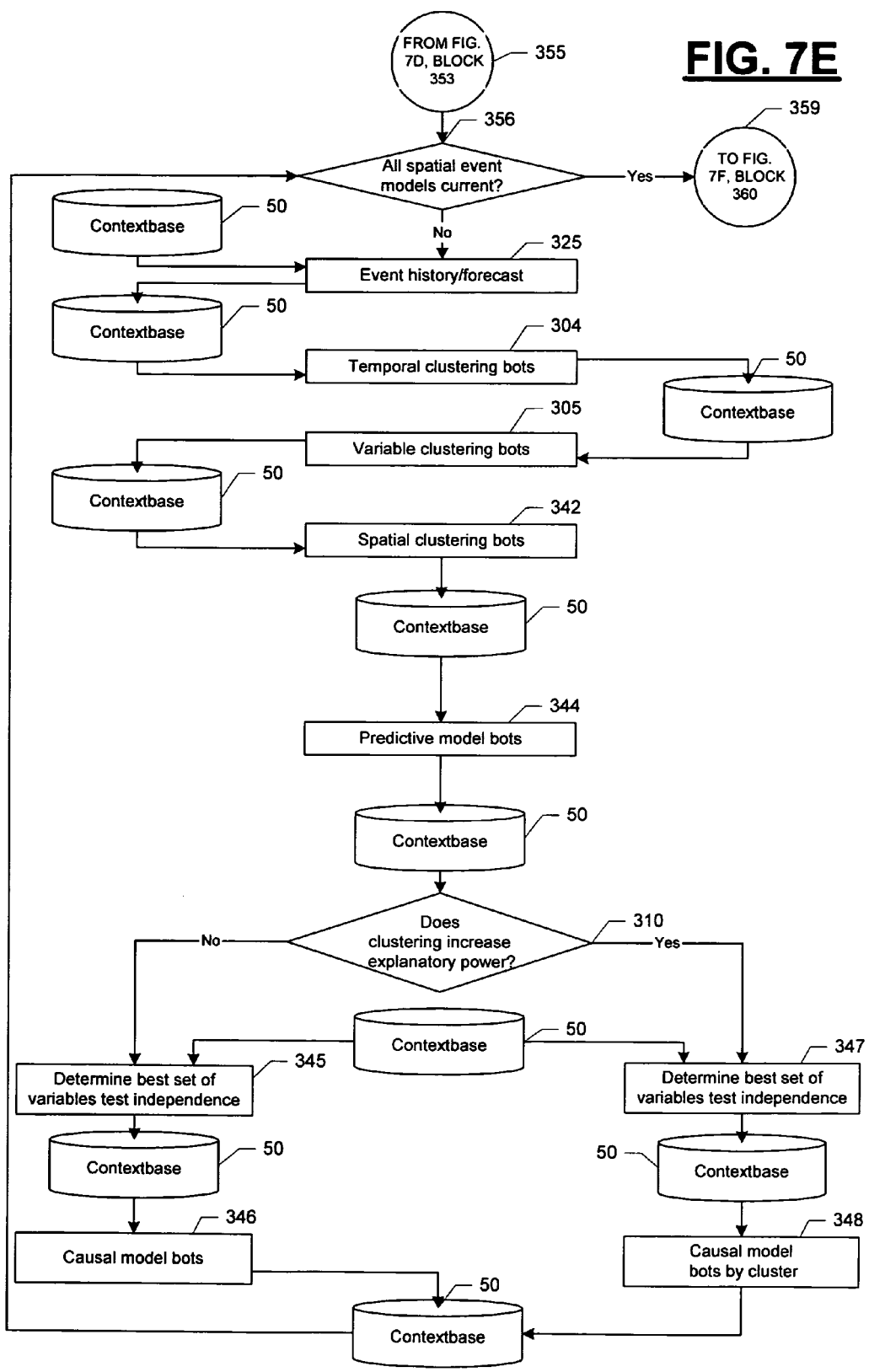
Figure 7F:
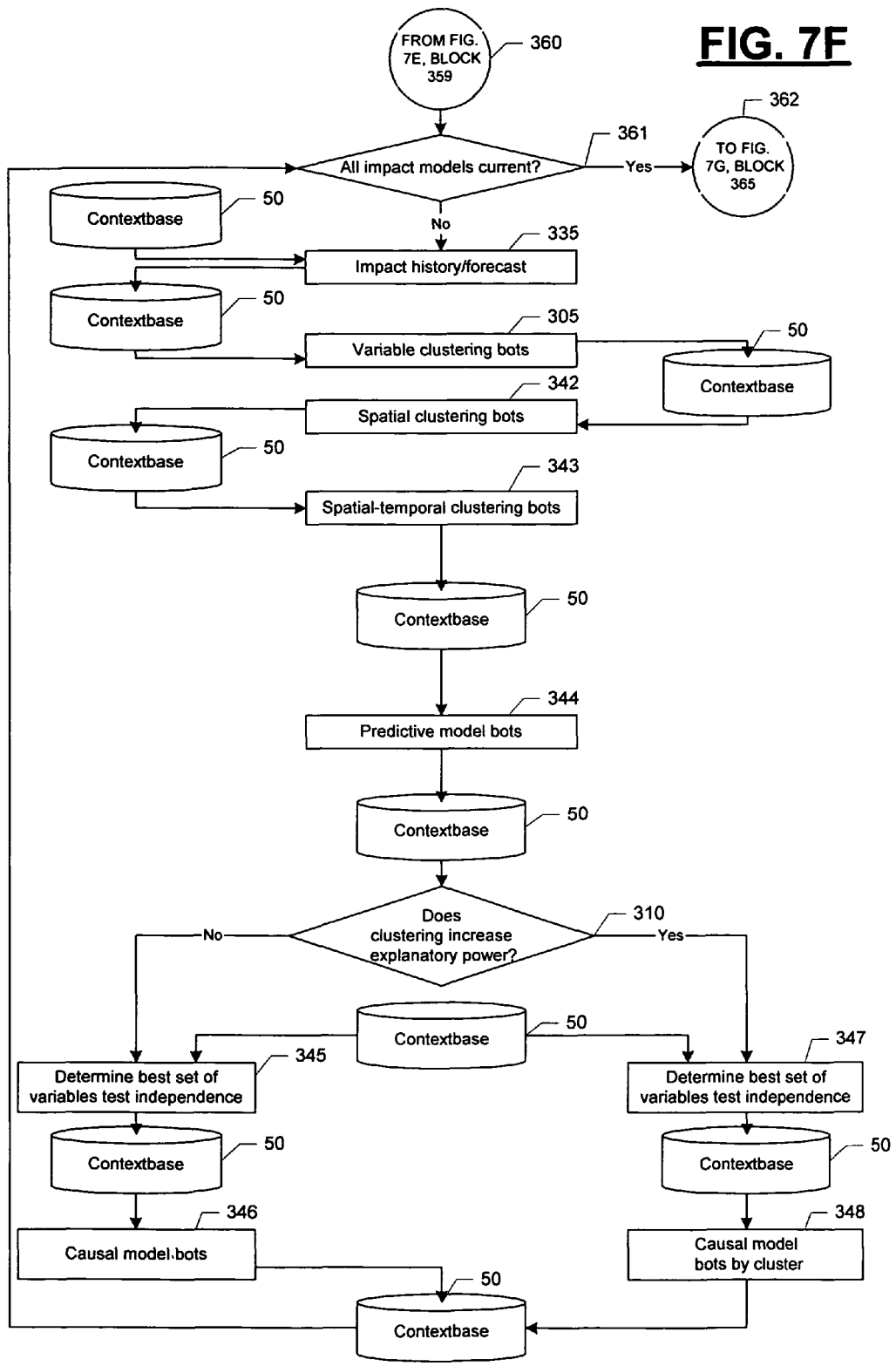
Figure 7H:
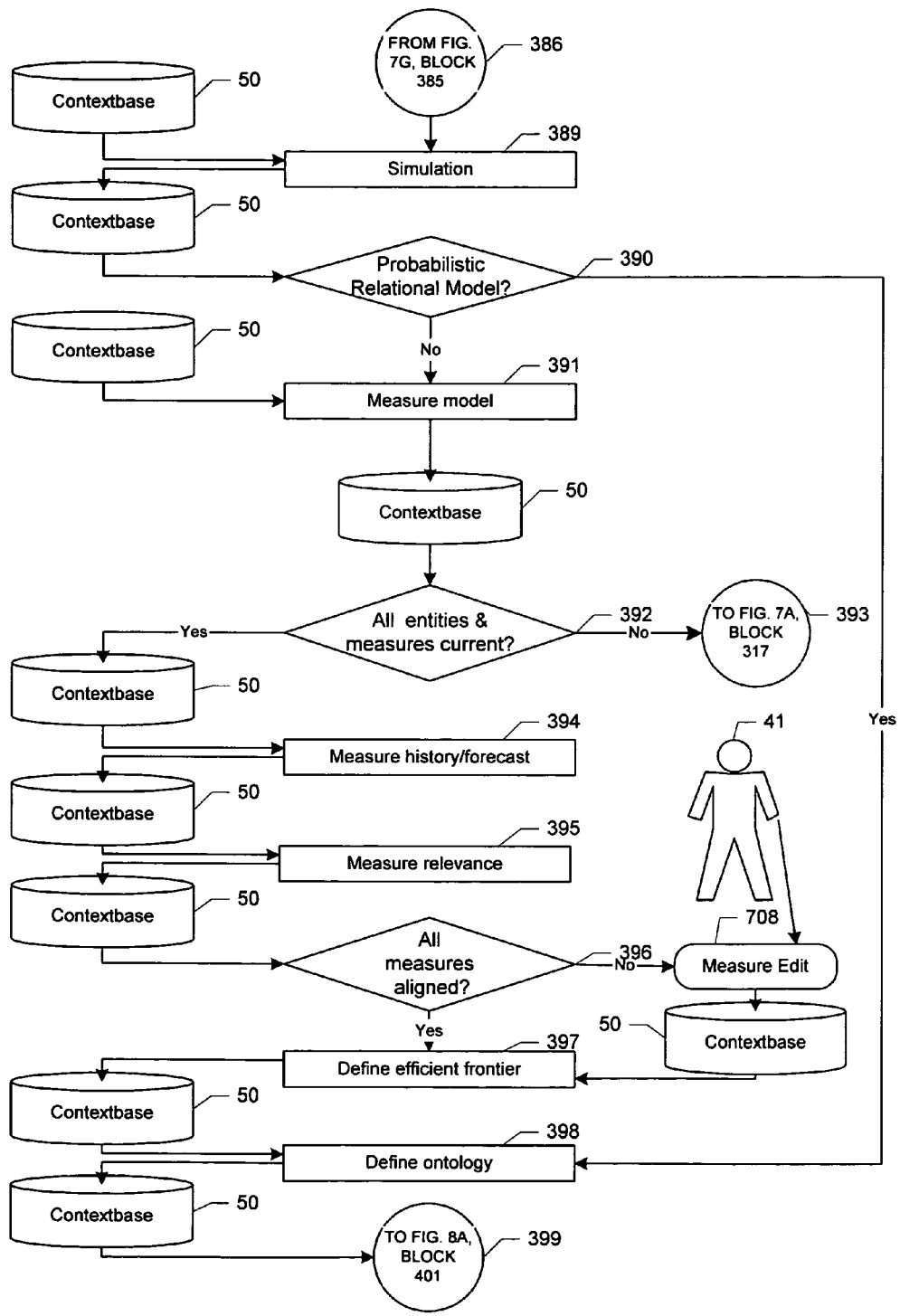
Figure 8B:
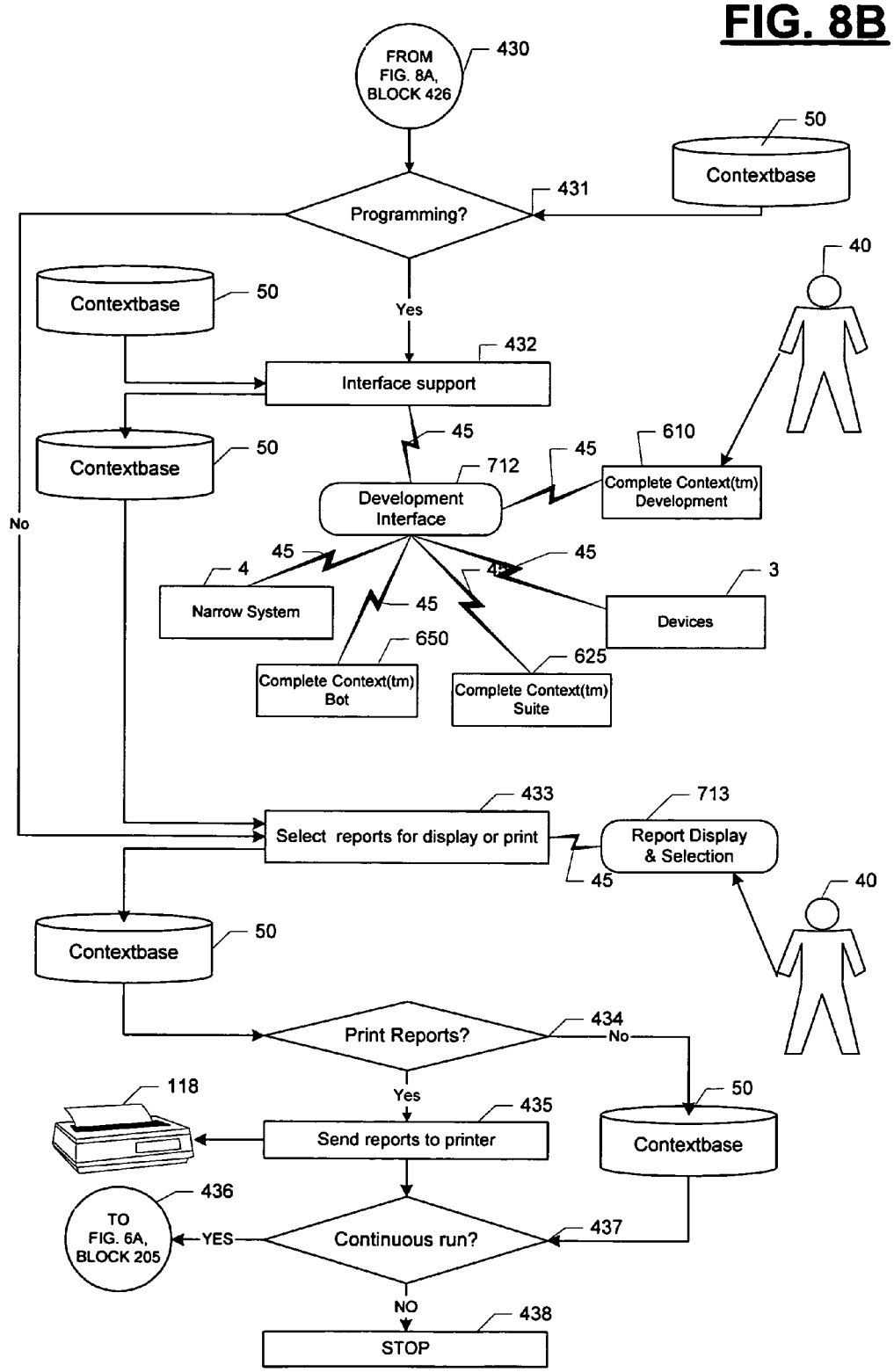
Figure 9:
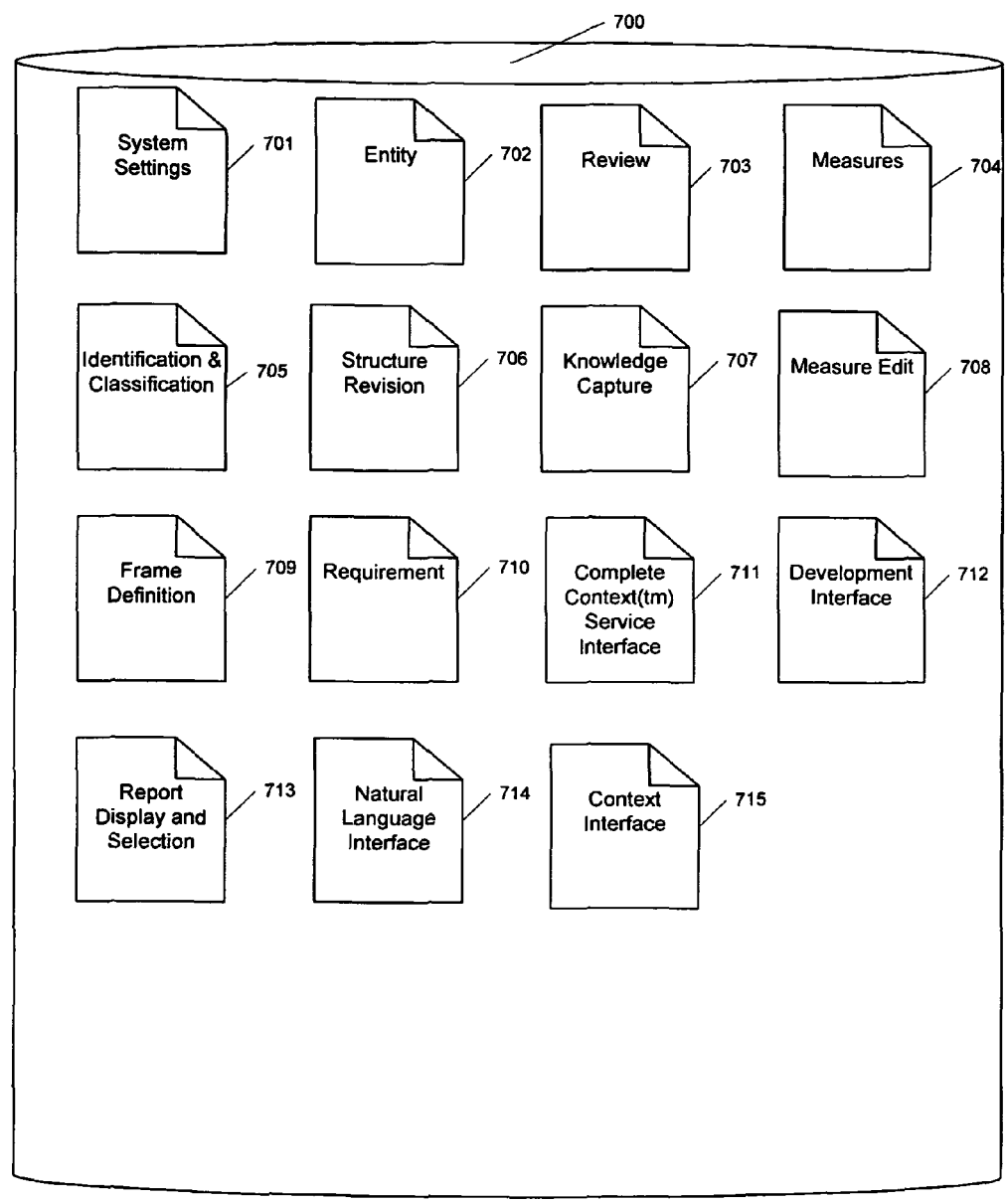
FIG. 9 is a diagram showing the data windows that are used for receiving information from and transmitting information via the interface (700)

As discussed previously, the Personalized Medicine Service (100) completes processing in three distinct stages. As shown in FIG. 6A, FIG. 6B and FIG. 6C the first stage of processing (block 200 from FIG. 1) identifies and prepares data from narrow system databases (5); external databases (7); the world wide web (8), external services (9) and optionally, a partner narrow system database (6) for processing. This stage also identifies the entity and entity function and/or mission measures. As shown in FIG. 7A, FIG. 7B, FIG. 7C, FIG. 7D, FIG. 7E, FIG. 7F, FIG. 7G and FIG. 7H, the second stage of processing (block 300 from FIG. 1) develops and then continually updates a contextbase (50) for each subject measure. As shown in FIG. 8A and FIG. 8B, the third stage of processing (block 400 from FIG. 1) identifies the valid context space before developing and distributing one or more entity contexts via a Personalized Medicine Service (100). The third stage of processing also prepares and prints optional reports. If the operation is continuous, then the processing steps described are repeated continuously. As described below, one embodiment of the software is a bot or agent architecture. Other architectures including a service architecture, an n-tier client server architecture, an integrated application architecture and combinations thereof can be used to the same effect.

Entity Definition

The flow diagrams in FIG. 6A, FIG. 6B and FIG. 6C detail the processing that is completed by the portion of the application software (200) that defines the subject, identifies the functions and measures for said subject, prepares data for use in processing and accepts user (40) and management (41) input. As discussed previously, the system of the present invention is capable of accepting data from and transmitting data to all the narrow systems (4) listed in Tables 4, 5, 6 and 7. It can also accept data from and transmit data to the devices listed in Table 8. Data extraction, processing and storage are normally completed by the Personalized Medicine Service (100). This data extraction, processing and storage can be facilitated by a separate data integration layer in an operating system or middleware application as described in cross referenced application Ser. No. 10/748,890. Operation of the Personalized Medicine Service (100) will be illustrated by describing the extraction and use of structured data from a narrow system database (5) for supply chain management and an external database (7). A brief overview of the information typically obtained from these two databases will be presented before reviewing each step of processing completed by this portion (200) of the application software.

Supply chain systems are one of the narrow systems (4) identified in Table 7. Supply chain databases are a type of narrow system database (5) that contain information that may have been in operation management system databases in the past. These systems provide enhanced visibility into the availability of resources and promote improved coordination between subject entities and their supplier entities. All supply chain systems would be expected to track all of the resources ordered by an entity after the first purchase. They typically store information similar to that shown below in Table 14.

TABLE 14

Supply chain system information

1. Stock Keeping Unit (SKU)
2. Vendor
3. Total quantity on order
4. Total quantity in transit
5. Total quantity on back order
6. Total quantity in inventory
7. Quantity available today
8. Quantity available next 7 days
9. Quantity available next 30 days
10. Quantity available next 90 days
11. Quoted lead time
12. Actual average lead time External databases (7) are used for obtaining information that enables the definition and evaluation of words, phrases, context elements, context factors and event risks. In some cases, information from these databases can be used to supplement information obtained from the other databases and the World Wide Web (5, 6 and 8). In the system of the present invention, the information extracted from external databases (7) includes the data listed in Table 15.

TABLE 15

External database information

1. Text information such as that found in the Lexis Nexis database
2. Text information from databases containing past issues of specific publications
3. Multimedia information such as video and audio clips
4. Idea market prices indicate likelihood of certain events occurring
5. Event risk data including information about risk probability and magnitude for weather and geological events
6. Known phonemes and phrases System processing of the information from the different data sources (3, 4, 5, 6, 7, 8 and 9) described above starts in a block 202, FIG. 6A. The software in block 202 prompts the user (40) via the system settings data window (701) to provide system setting information. The system setting information entered by the user (40) is stored in the system settings table (162) in the contextbase (50). The specific inputs the user (40) is asked to provide at this point in processing are shown in Table 16.

TABLE 16

1. Continuous, if yes, calculation frequency? (by minute, hour, day, week, etc.)
2. Subject (patient, group or patient-entity multi domain system)
3. SIC Codes
4. Names of primary competitors by SIC Code (if applicable)
5. Base account structure
6. Base units of measure
7. Base currency
8. Risk free interest rate
9. Program bots or applications? (yes or no)
10. Process measurements? (yes or no)
11. Probabilistic relational models? (yes or no)
12. Knowledge capture and/or collaboration? (yes or no)
13. Natural language interface? (yes, no or voice activated)
14. Video data extraction? (yes or no)
15. Image data extraction? (yes or no)
16. Internet data extraction? (yes or no)
17. Reference layer? (yes or no, if yes specify coordinate system(s))
18. Text data analysis?
19. Geo-coded data? (if yes, then specify standard)
20. Maximum number of clusters (default is six)
21. Management report types (text, graphic or both)

TABLE 16-continued

22. Default missing data procedure (chose from selection)
23. Maximum time to wait for user input
24. Maximum number of subelements
25. Most likely scenario, normal, extreme or mix (default is normal)
26. System time period (days, month, years, decades, light years, etc.)
27. Date range for history-forecast time periods (optional)
28. Uncertainty level and source by narrow system type (optionally, default is zero)
29. Weight of evidence cutoff level (by context)
30. Time frame(s) for proactive search (hours, days, weeks, etc.)
31. Node depth for scouting and/or searching for data, information and knowledge
32. Impact cutoff for scouting and/or searching for data, information and knowledge The system settings data are used by the software in block 202 to establish context layers. As described previously, there are generally eight types of context layers for the subject. The application of the remaining system settings will be further explained as part of the detailed explanation of the system operation. The software in block 202 also uses the current system date and the system time period saved in the system settings table (162) to determine the time periods (generally in months) where data will be sought to complete the calculations. The user (40) also has the option of specifying the time periods that will be used for system calculations. After the date range is stored in the system settings table (162) in the contextbase (50), processing advances to a software block 203.

The software in block 203 prompts the user (40) via the entity data window (702) to identify the subject, identify subject functions and identify any extensions to the subject hierarchy or hierarchies specified in the system settings table (162). For example if the organism hierarchy (2300) was chosen, the user (40) could extend the hierarchy by specifying a join with the cellular hierarchy (2200). As part of the processing in this block, the user (40) is also given the option to modify the subject hierarchy or hierarchies. If the user (40) elects to modify one or more hierarchies, then the software in the block will prompt the user (40) to provide information for use in modifying the pre-defined hierarchy metadata in the hierarchy metadata table (155) to incorporate the modifications. The user (40) can also elect to limit the number of separate levels that are analyzed below the subject in a given hierarchy. For example, an organization could choose to examine the impact of their divisions on organization performance by limiting the context elements to one level below the subject. After the user (40) completes the specification of hierarchy extensions, modifications and limitations, the software in block 203 selects the appropriate metadata from the hierarchy metadata table (155) and establishes the hierarchy metadata (155) and stores the ontology (152) and entity schema (157). The software in block 203 uses the extensions, modifications and limitations together with three rules for establishing the entity schema:

1. the members of the entity hierarchy that are above the subject are factors;
2. hierarchies that could be used to extend the entity hierarchy that are not selected will be excluded; and
3. all other hierarchies and groups will be potential factors.

After subject schema is developed, the user (40) is asked to define process maps and procedures. The maps and procedures identified by the user (40) are stored in the relationship layer table (144) in the contextbase (50). The information provided by the user (40) will be supplemented with information developed later in the first stage of processing. It is also possible to obtain relationship layer information concerning process maps and procedures in an automated fashion by analyzing transaction patterns or reverse engineering narrow systems (4) as they often codify the relationship between different context elements, factors, events, resources and/or actions. The Complete Context™ Capture and Collaboration Service (622) can also be used here to supplement the information provided by the user (40) with information from subject matter experts (42). After data storage is complete, processing advances to a software block 204.

The software in block 204 prompts a context interface window (715) to communicate via a network (45) with the different devices (3), systems (4), databases (5, 6, 7), the World Wide Web (8) and external services (9) that are data sources for the Personalized Medicine Service (100). As shown on FIG. 10 the context interface window (715) contains a multiple step operation where the sequence of steps depends on the nature of the interaction and the data being provided to the Medicine Service (100). In one embodiment, a data input session would be managed by the a software block (720) that identifies the data source (3, 4, 5, 6, 7, 8 or 9) using standard protocols such as UDDI or xml headers, maintains security and establishes a service level agreement with the data source (3, 4, 5, 6, 7, 8 or 9). The data provided at this point could include transaction data, descriptive data, imaging data, video data, text data, sensor data, geospatial coordinate data, array data, virtual reference coordinate data and combinations thereof. The session would proceed to a software block (722) for pre-processing such as discretization, transformation and/or filtering. After completing the pre-processing in software block 722, processing would advance to a software block (724). The software in that block would determine if the data provided by the data source (3, 4, 5, 6, 7, 8 or 9) complied with the entity schema or ontology using pairwise similarity measures on several dimensions including terminology, internal structure, external structure, extensions, hierarchical classifications (see Tables 1, 2 and 3) and semantics. If it did comply, then the data would not require alignment and the session would advance to a software block (732) where any conversions to match the base units of measure, currency or time period specified in the system settings table (162) would be identified before the session advanced to a software block (734) where the location of this data would be mapped to the appropriate context layers and stored in the contextbase (50). Establishing a virtual database in this manner eliminates the latency that can cause problems for real time processing. The virtual database information for the element layer for the subject and context elements is stored in the element layer table (141) in the contextbase (50). The virtual database information for the resource layer for the subject resources is stored in the resource layer table (143) in the contextbase (50). The virtual database information for the environment layer for the subject and context factors is stored in the environment layer table (149) in the contextbase (50). The virtual database information for the transaction layer for the subject, context elements, actions and events is stored in the transaction layer table (142) in the contextbase (50). The processing path described in this paragraph is just one of many paths for processing data input.

Figure 10:
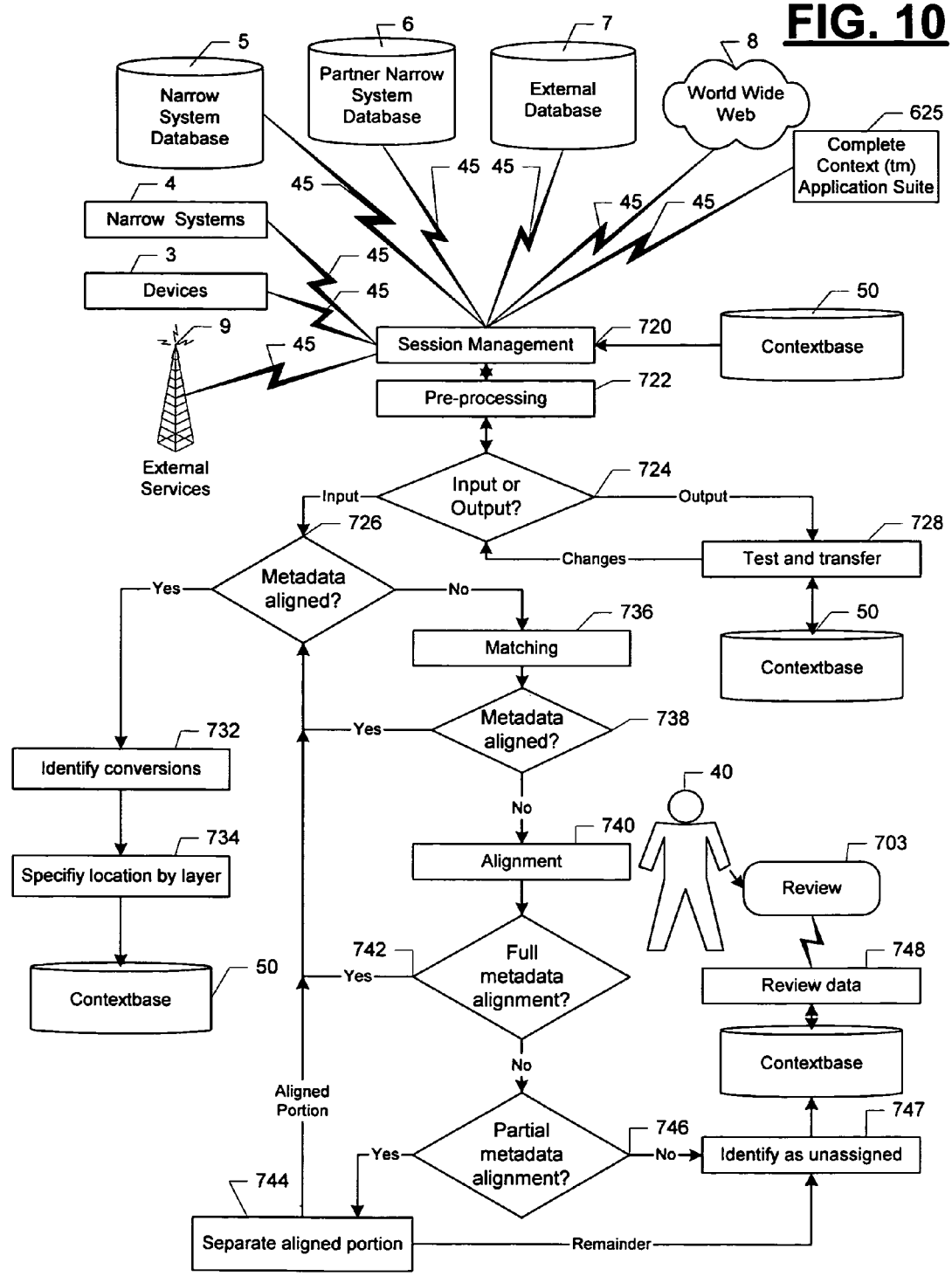
FIG. 10 is a block diagram showing the sequence of processing steps in the present invention used for identifying, receiving and transmitting data with narrow systems (4)

As shown FIG. 10, the context interface window (715) has provisions for an alternate data input processing path. This path is used if the data are not in alignment with the entity schema (157) or ontology (152). In this alternate mode, the data input session would still be managed by the session management software in block (720) that identifies the data source (3, 4, 5, 6, 7, 8 or 9) maintains security and establishes a service level agreement with the data source (3, 4, 5, 6, 7, 8 or 9). The session would proceed to the pre-processing software block (722) where the data from one or more data sources (3,4, 5, 6, 7, 8 or 9) that requires translation and optional analysis is processed before proceeding to the next step. The software in block 722 has provisions for translating, parsing and other pre-processing of audio, image, microarray, transaction, video and unformatted text data formats to schema or ontology compliant formats (xml formats in one embodiment). The audio, text and video data are prepared as detailed in cross referenced patent application Ser. No. 10/717,026. Image translation involves conversion, registration, segmentation and segment identification using object boundary models. Other image analysis algorithms can be used to the same effect. Other pre-processing steps can include discretization and stochastic resonance processing. After pre-processing is complete, the session advances to a software block 724. The software in block 724 determine whether or not the data was in alignment with the ontology (152) or schema (157) stored in the contextbase (50) using pair wise comparisons as described previously. Processing then advances to the software in block 736 which uses the mappings identified by the software in block 724 together with a series of matching algorithms including key properties, similarity, global namespace, value pattern and value range algorithms to align the input data with the entity schema (157) or ontology (152). Processing, then advances to a software block 738 where the metadata associated with the data are compared with the metadata stored in the subject schema table (157). If the metadata are aligned, then processing is completed using the path described previously. Alternatively, if the metadata are still not aligned, then processing advances to a software block 740 where joins, intersections and alignments between the two schemas or ontologies are completed in an automated fashion. Processing then advances to a software block 742 where the results of these operations are compared with the schema (157) or ontology (152) stored in the contextbase (50). If these operations have created alignment, then processing is completed using the path described previously. Alternatively, if the metadata are still not aligned, then processing advances to a software block 746 where the schemas and/or ontologies are checked for partial alignment. If there is partial alignment, then processing advances to a software block 744. Alternatively, if there is no alignment, then processing advances to a software block 747 where the data are tagged for manual review and stored in the unassigned data table (146). The software in block 744 cleaves the data in order to separate the portion that is in alignment from the portion that is not in alignment. The portion of the data that is not in alignment is forwarded to software block 747 where it is tagged for manual alignment and stored in the unassigned data table (146). The portion of the data that is in alignment is processed using the path described previously. Processing advances to a block 748 where the user (40) reviews the unassigned data table (146) using the review window (703) to see if the entity schema should be modified to encompass the currently unassigned data and the changes in the schema (157) and/or ontology (152)—if any—are saved in the contextbase (50).

After context interface window (715) processing is completed for all available data from the devices (3), systems (4), databases (5, 6 and 7), the World Wide Web (8), and external services (9), processing advances to a software block 206 where the software in block 206 optionally prompts the context interface window (715) to communicate via a network (45) with the Complete Context™ Input Service (601). The context interface window (715) uses the path described previously for data input to map the identified data to the appropriate context layers and store the mapping information in the contextbase (50) as described previously. After storage of the Complete Context™ Input Service (601) data are complete, processing advances to a software block 207.

The software in block 207 prompts the user (40) via the review data window (703) to optionally review the context layer data that has been stored in the first few steps of processing. The user (40) has the option of changing the data on a one time basis or permanently. Any changes the user (40) makes are stored in the table for the corresponding context layer (i.e. transaction layer changes are saved in the transaction layer table (142), etc.). As part of the processing in this block, an interactive GEL algorithm prompts the user (40) via the review data window (703) to check the hierarchy or group assignment of any new elements, factors and resources that have been identified. Any newly defined categories are stored in the relationship layer table (144) and the subject schema table (157) in the contextbase (50) before processing advances to a software block 208.

The software in block 208 prompts the user (40) via the requirement data window (710) to optionally identify requirements for the subject. Requirements can take a variety of forms but the two most common types of requirements are absolute and relative. For example, a requirement that the level of cash should never drop below $50,000 is an absolute requirement while a requirement that there should never be less than two months of cash on hand is a relative requirement. The user (40) also has the option of specifying requirements as a subject function later in this stage of processing. Examples of different requirements are shown in Table 17.

TABLE 17

| Entity | Requirement (reason) |
| --- | --- |
| Individual (1401) | Stop working at 67 (retirement) |
| | Keep blood pressure below 155/95 |
| | (health) Available funds > $X by |
| | Jan. 01, 2004 (college for daughter) |
| Government | Foreign currency reserves > $X |
| Organization (1607) | (IMF requirement) 3 functional divisions |
| | on standby (defense) Pension assets > |
| | liabilities (legal) |
| Circulatory | Cholesterol level between 120 and 180 |
| System (2304) | Pressure between 110/75 and 150/100 |

The software in this block provides the ability to specify absolute requirements, relative requirements and standard "requirements" for any reporting format that is defined for use by the Complete Context™ Review Service (607). After requirements are specified, they are stored in the requirement table (159) in the contextbase (50) by entity before processing advances to a software block 211.

The software in block 211 checks the unassigned data table (146) in the contextbase (50) to see if there are any data that has not been assigned to an entity and/or context layer. If there are no data without a complete assignment (entity and element, resource, factor or transaction context layer constitutes a complete assignment), then processing advances to a software block 214. Alternatively, if there are data without an assignment, then processing advances to a software block 212. The software in block 212 prompts the user (40) via the identification and classification data window (705) to identify the context layer and entity assignment for the data in the unassigned data table (146). After assignments have been specified for every data element, the resulting assignments are stored in the appropriate context layer tables in the contextbase (50) by entity before processing advances to a software block 214.

The software in block 214 checks the element layer table (141), the transaction layer table (142) and the resource layer table (143) and the environment layer table (149) in the contextbase (50) to see if data are missing for any specified time period. If data are not missing for any time period, then processing advances to a software block 218. Alternatively, if data for one or more of the specified time periods identified in the system settings table (162) for one or more items is missing from one or more context layers, then processing advances to a software block 216. The software in block 216 prompts the user (40) via the review data window (703) to specify the procedure that will be used for generating values for the items that are missing data by time period. Options the user (40) can choose at this point include: the average value for the item over the entire time period, the average value for the item over a specified time period, zero or the average of the preceding item and the following item values and direct user input for each missing value. If the user (40) does not provide input within a specified interval, then the default missing data procedure specified in the system settings table (162) is used. When the missing time periods have been filled and stored for all the items that were missing data, then system processing advances to a block 218.

The software in block 218 retrieves data from the element layer table (141), the transaction layer table (142), the resource layer table (143) and the environment layer table (149). It uses this data to calculate indicators for the data associated with each element, resource and environmental factor. The indicators calculated in this step are comprised of comparisons, regulatory measures and statistics. Comparisons and statistics are derived for: appearance, description, numeric, shape, shape/time and time characteristics. These comparisons and statistics are developed for different types of data as shown below in Table 18.

TABLE 18

| Characteristic/ Data type | Appearance | Description | Numeric | Shape | Shape-Time | Time |
|---|---|---|---|---|---|---|
| audio | | X | X | | | X |
| coordinate | | X | X | X | X | X |
| image | X | | X | X | X | X |
| text | | X | X | | | X |
| transaction | | | X | | | X |
| video | X | | X | X | X | X |

X = comparisons and statistics are developed for these characteristic/data type combinations Numeric characteristics are pre-assigned to different domains. Numeric characteristics include amperage, area, concentration, density, depth, distance, growth rate, hardness, height, hops, impedance, level, mass to charge ratio, nodes, quantity, rate, resistance, similarity, speed, tensile strength, voltage, volume, weight and combinations thereof. Time characteristics include frequency measures, gap measures (i.e. time since last occurrence, average time between occurrences, etc.) and combinations thereof. The numeric and time characteristics are also combined to calculate additional indicators. Comparisons include: comparisons to baseline (can be binary, 1 if above, 0 if below), comparisons to external expectations, comparisons to forecasts, comparisons to goals, comparisons to historical trends, comparisons to known bad, comparisons to known good, life cycle comparisons, comparisons to normal, comparisons to peers, comparisons to regulations, comparison to requirements, comparisons to a standard, sequence comparisons, comparisons to a threshold (can be binary, 1 if above, 0 if below) and combinations thereof. Statistics include: averages (mean, median and mode), convexity, copulas, correlation, covariance, derivatives, Pearson correlation coefficients, slopes, trends and variability. Time lagged versions of each piece of data, statistic and comparison are also developed. The numbers derived from these calculations are collectively referred to as "indicators" (also known as item performance indicators and factor performance indicators). The software in block 218 also calculates mathematical and/or logical combinations of indicators called composite variables (also known as composite factors when associated with environmental factors). These combinations include both pre-defined combinations and derived combinations. The AQ program is used for deriving combinations. It should be noted that other attribute derivation algorithms, such as the LINUS algorithms, may be used to generate the combinations. The indicators and the composite variables are tagged and stored in the appropriate context layer table—the element layer table (141), the resource layer table (143) or the environment layer table (149)—before processing advances to a software block 220.

The software in block 220 checks the bot date table (163) and deactivates pattern bots with creation dates before the current system date and retrieves information from the system settings table (162), the element layer table (141), the transaction layer table (142), the resource layer table (143) and the environment layer table (149). The software in block 220 then initializes pattern bots for each layer to identify patterns in each layer. Bots are independent components of the application software of the present invention that complete specific tasks. In the case of pattern bots, their tasks are to identify patterns in the data associated with each context layer. In one embodiment, pattern bots use Apriori algorithms identify patterns including frequent patterns, sequential patterns and multi-dimensional patterns. However, a number of other pattern identification algorithms including the sliding window algorithm; differential association rule, beam-search, frequent pattern growth, decision trees and the PASCAL algorithm can be used alone or in combination to the same effect. Every pattern bot contains the information shown in Table 19.

TABLE 19

1. Unique ID number (based on date, hour, minute, second of creation)
2. Creation date (date, hour, minute, second)
3. Storage location
4. Entity type(s)
5. Entity
6. Context Layer
7. Algorithm After being initialized, the bots identify patterns for the data associated with elements, resources, factors and combinations thereof. Each pattern is given a unique identifier and the frequency and type of each pattern is determined. The numeric values associated with the patterns are indicators. The values are stored in the appropriate context layer table before processing advances to a software block 222.

The software in block 222 uses causal association algorithms including LCD, CC and CU to identify causal associations between indicators, composite variables, element data, factor data, resource data and events, actions, processes and measures. The software in this block uses semantic association algorithms including path length, subsumption, source uncertainty and context weight algorithms to identify associations. The identified associations are stored in the causal link table (148) for possible addition to the relationship layer table (144) before processing advances to a software block 224.

The software in block 224 uses a tournament of petri nets, time warping algorithms and stochism algorithms to identify probable subject processes in an automated fashion. Other pathway identification algorithms can be used to the same effect. The identified processes are stored in the relationship layer table (144) before processing advances to a software block 226.

The software in block 226 prompts the user (40) via the review data window (703) to optionally review the new associations stored in the causal link table (148) and the newly identified processes stored in the relationship layer table (144). Associations and/or processes that have already been specified or approved by the user (40) will not be displayed automatically. The user (40) has the option of accepting or rejecting each identified association or process. Any associations or processes the user (40) accepts are stored in the relationship layer table (144) before processing advances a software block 242.

The software in block 242 checks the measure layer table (145) in the contextbase (50) to determine if there are current models for all measures for every entity. If all measure models are current, then processing advances to a software block 252. Alternatively, if all measure models are not current, then the next measure for the next entity is selected and processing advances to a software block 244.

The software in block 244 checks the bot date table (163) and deactivates event risk bots with creation dates before the current system date. The software in the block then retrieves the information from the transaction layer table (142), the relationship layer table (144), the event risk table (156), the subject schema table (157) and the system settings table (162) in order to initialize event risk bots for the subject in accordance with the frequency specified by the user (40) in the system settings table (162). Bots are independent components of the application software that complete specific tasks. In the case of event risk bots, their primary tasks are to forecast the frequency and magnitude of events that are associated with negative measure performance in the relationship layer table (144). In addition to forecasting risks that are traditionally covered by insurance such as fires, floods, earthquakes and accidents, the system of the present invention also uses the data to forecast standard, "non-insured" event risks such as the risk of employee resignation and the risk of customer defection. The system of the present invention uses a tournament forecasting method for event risk frequency and duration. The mapping information from the relationship layer is used to identify the elements, factors, resources and/or actions that will be affected by each event. Other forecasting methods can be used to the same effect. Every event risk bot contains the information shown in Table 20.

TABLE 20

1. Unique ID number (based on date, hour, minute, second of creation)
2. Creation date (date, hour, minute, second)
3. Mapping information
4. Storage location
5. Hierarchy or group
6. Entity
7. Event (fire, flood, earthquake, tornado, accident, defection, etc.)

After the event risk bots are initialized they activate in accordance with the frequency specified by the user (40) in the system settings table (162). After being activated the bots retrieve the specified data and forecast the frequency and measure impact of the event risks. The resulting forecasts are stored in the event risk table (156) before processing advances to a software block 246.

The software in block 246 checks the bot date table (163) and deactivates extreme risk bots with creation dates before the current system date. The software in block 246 then retrieves the information from the transaction layer table (142), the relationship layer table (144), the event risk table (156), the subject schema table (157) and the system settings table (162) in order to initialize extreme risk bots in accordance with the frequency specified by the user (40) in the system settings table (162). Bots are independent components of the application software that complete specific tasks. In the case of extreme risk bots, their primary task is to forecast the probability of extreme events for events that are associated with negative measure performance in the relationship layer table (144). The extreme risks bots use the Blocks method and the peak over threshold method to forecast extreme risk magnitude and frequency. Other extreme risk algorithms can be used to the same effect. The mapping information is then used to identify the elements, factors, resources and/or actions that will be affected by each extreme risk. Every extreme risk bot activated in this block contains the information shown in Table 21.

TABLE 21

1. Unique ID number (based on date, hour, minute, second of creation)
2. Creation date (date, hour, minute, second)
3. Mapping information
4. Storage location
5. Hierarchy or Group
6. Entity
7. Method: blocks or peak over threshold
8. Event (fire, flood, earthquake, tornado, accident, defection, etc.)

After the extreme risk bots are initialized, they activate in accordance with the frequency specified by the user (40) in the system settings table (162). Once activated, they retrieve the specified information, forecast extreme event risks and map the impacts to the different elements, factors, resources and/or actions. The extreme event risk information is stored in the event risk table (156) in the contextbase (50) before processing advances to a software block 248.

The software in block 248 checks the bot date table (163) and deactivates competitor risk bots with creation dates before the current system date. The software in block 248 then retrieves the information from the transaction layer table (142), the relationship layer table (144), the event risk table (156), the subject schema table (157) and the system settings table (162) in order to initialize competitor risk bots in accordance with the frequency specified by the user (40) in the system settings table (162). Bots are independent components of the application software that complete specific tasks. In the case of competitor risk bots, their primary task is to identify the probability of competitor actions and/or events that are associated with negative measure performance in the relationship layer table (144). The competitor risk bots use game theoretic real option models to forecast competitor risks. Other risk forecasting algorithms can be used to the same effect. The mapping information is then used to identify the elements, factors, resources and/or actions that will be affected by each customer risk. Every competitor risk bot activated in this block contains the information shown in Table 22.

TABLE 22

1. Unique ID number (based on date, hour, minute, second of creation)
2. Creation date (date, hour, minute, second)
3. Mapping information
4. Storage location
5. Entity type(s)
6. Entity
7. Competitor After the competitor risk bots are initialized, they retrieve the specified information and forecast the frequency and magnitude of competitor risks. The bots save the competitor risk information in the event risk table (156) in the contextbase (50) and processing advances to a block 250.

The software in block 250 retrieves data from the event risk table (156) and the subject schema table (157) before using a measures data window (704) to display a table showing the distribution of risk impacts by element, factor, resource and action. After the review of the table is complete, the software in block 250 prompts the manager (41) via the measures data window (704) to specify one or more measures for the subject. Measures are quantitative indications of subject behavior or performance. The primary types of behavior are production (includes improvements and new creations), destruction (includes reductions and complete destruction) and maintenance. As discussed previously, the manager (41) is given the option of using pre-defined measures or creating new measures using terms defined in the subject schema table (157). The measures can combine performance and risk measures or the performance and risk measures can be kept separate. If more than one measure is defined for the subject, then the manager (41) is prompted to assign a weighting or relative priority to the different measures that have been defined. As system processing advances, the assigned priorities can be compared to the priorities that entity actions indicate are most important. The priorities used to guide analysis can be the stated priorities, the inferred priorities or some combination thereof. The gap between stated priorities and actual priorities is a congruence measure that can be used in analyzing aspects of performance—particularly mental health.

After the specification of measures and priorities has been completed, the values of each of the newly defined measures are calculated using historical data and forecast data. If forecast data are not available, then the Complete Context™ Forecast Service (603) is used to supply the missing values. These values are then stored in the measure layer table (145) along with the measure definitions and priorities. When data storage is complete, processing advances to a software block 252.

The software in block 252 checks the bot date table (163) and deactivates forecast update bots with creation dates before the current system date. The software in block 252 then retrieves the information from the system settings table (162) and environment layer table (149) in order to initialize forecast bots in accordance with the frequency specified by the user (40) in the system settings table (162). Bots are independent components of the application software of the present invention that complete specific tasks. In the case of forecast update bots, their task is to compare the forecasts for context factors and with the information available from futures exchanges (including idea markets) and update the existing forecasts. This function is generally only used when the system is not run continuously. Every forecast update bot activated in this block contains the information shown in Table 23.

TABLE 23

1. Unique ID number (based on date, hour, minute, second of creation)
2. Creation date (date, hour, minute, second)
3. Mapping information
4. Storage location
5. Entity type(s)
6. Entity
7. Context factor
8. Measure
9. Forecast time period After the forecast update bots are initialized, they activate in accordance with the frequency specified by the user (40) in the system settings table (162). Once activated, they retrieve the specified information and determine if any forecasts need to be updated to bring them in line with the market data. The bots save the updated forecasts in the environment layer table (149) by entity and processing advances to a software block 254.

The software in block 254 checks the bot date table (163) and deactivates scenario bots with creation dates before the current system date. The software in block 254 then retrieves the information from the system settings table (162), the element layer table (141), the transaction layer table (142), the resource layer table (143), the relationship layer table (144), the environment layer table (149), the event risk table (156) and the subject schema table (157) in order to initialize scenario bots in accordance with the frequency specified by the user (40) in the system settings table (162).

Bots are independent components of the application software of the present invention that complete specific tasks. In the case of scenario bots, their primary task is to identify likely scenarios for the evolution of the elements, factors, resources and event risks by entity. The scenario bots use the statistics calculated in block 218 together with the layer information retrieved from the contextbase (50) to develop forecasts for the evolution of the elements, factors, resources, events and actions under normal conditions, extreme conditions and a blended extreme-normal scenario. Every scenario bot activated in this block contains the information shown in Table 24.

TABLE 24

1. Unique ID number (based on date, hour, minute, second of creation)
2. Creation date (date, hour, minute, second)
3. Mapping information
4. Storage location
5. Type: normal, extreme or blended
6. Entity type(s)
7. Entity
8. Measure After the scenario bots are initialized, they activate in accordance with the frequency specified by the user (40) in the system settings table (162). Once activated, they retrieve the specified information and develop a variety of scenarios as described previously. After the scenario bots complete their calculations, they save the resulting scenarios in the scenarios table (168) by entity in the contextbase (50) and processing advances to a block 301.

Contextbase Development

The flow diagrams in FIG. 7A, FIG. 7B, FIG. 7C, FIG. 7D, FIG. 7E, FIG. 7F, FIG. 7G and FIG. 7H detail the processing that is completed by the portion of the application software (300) that continually develops a function measure oriented contextbase (50) by creating and activating analysis bots that:

1. Supplement the relationship layer (144) information developed previously by identifying relationships between the elements, factors, resources, events, actions and one or more measures;
2. Complete the measure layer (145) by developing robust models of the elements, factors, resources, events and/or actions driving measure performance;
3. Develop robust models of the elements, factors, resources and events driving action and/or event occurrence rates and impact levels;
4. Analyze measures for the subject hierarchy in order to evaluate alignment and adjust measures in order to achieve alignment in an automated fashion; and
5. Determine the relationship between function and/or mission measures and subject performance.

Each analysis bot generally normalizes the data being analyzed before processing begins. As discussed previously, processing in this embodiment includes an analysis of all measures and alternative architectures that include a web and/or grid service architecture. The system of the present invention can combine any number of measures in order to evaluate the performance of any entity in the seventeen hierarchies/groups described previously.

Before discussing this stage of processing in more detail, it will be helpful to review the processing already completed. As discussed previously, we are interested developing the complete context for the behavior of a subject. We will develop this complete context by developing a detailed understanding of the impact of elements, environmental factors, resources, events, actions and other relevant entities on one or more subject function and/or mission measures. Some of the elements and resources may have been grouped together to complete processes (a special class of element). The first stage of processing reviewed the data from some or all of the narrow systems (4) listed in Table 4, 5, 6 and 7 and the devices (3) listed in Table 8 and established a contextbase (50) that formalized the understanding of the identity and description of the elements, factors, resources, events and transactions that impact subject function and/or mission measure performance. The contextbase (50) also ensures ready access to the data used for the second and third stages of computation in the Personalized Medicine Service (100). In the second stage of processing we will use the contextbase (50) to develop an understanding of the relative impact of the different elements, factors, resources, events and transactions on subject measures.

Because processes rely on elements and resources to produce actions, the user (40) is given the choice between a process view and an element view for measure analysis to avoid double counting. If the user (40) chooses the element approach, then the process impact can be obtained by allocating element and resource impacts to the processes. Alternatively, if the user (40) chooses the process approach, then the process impacts can be divided by element and resource.

Processing in this portion of the application begins in software block 301. The software in block 301 checks the measure layer table (145) in the contextbase (50) to determine if there are current models for all measures for every entity. Measures that are integrated to combine the performance and risk measures into an overall measure are considered two measures for purposes of this evaluation. If all measure models are current, then processing advances to a software block 322. Alternatively, if all measure models are not current, then processing advances to a software block 302.

The software in block 302 checks the subject schema table (157) in the contextbase (50) to determine if spatial data is being used. If spatial data is being used, then processing advances to a software block 341. Alternatively, if all spatial data are not being used, then processing advances to a software block 303.

The software in block 303 retrieves the previously calculated values for the next measure from the measure layer table (145) before processing advances to a software block 304. The software in block 304 checks the bot date table (163) and deactivates temporal clustering bots with creation dates before the current system date. The software in block 304 then initializes bots in accordance with the frequency specified by the user (40) in the system settings table (162). The bots retrieve information from the measure layer table (145) for the entity being analyzed and defines regimes for the measure being analyzed before saving the resulting cluster information in the relationship layer table (144) in the contextbase (50). Bots are independent components of the application software of the present invention that complete specific tasks. In the case of temporal clustering bots, their primary task is to segment measure performance into distinct time regimes that share similar characteristics. The temporal clustering bot assigns a unique identification (id) number to each "regime" it identifies before tagging and storing the unique id numbers in the relationship layer table (144). Every time period with data are assigned to one of the regimes. The cluster id for each regime is associated with the measure and entity being analyzed. The time regimes are developed using a competitive regression algorithm that identifies an overall, global model before splitting the data and creating new models for the data in each partition. If the error from the two models is greater than the error from the global model, then there is only one regime in the data. Alternatively, if the two models produce lower error than the global model, then a third model is created. If the error from three models is lower than from two models then a fourth model is added. The processing continues until adding a new model does not improve accuracy. Other temporal clustering algorithms may be used to the same effect. Every temporal clustering bot contains the information shown in Table 25.

TABLE 25

1. Unique ID number (based on date, hour, minute, second of creation)
2. Creation date (date, hour, minute, second)
3. Mapping information
4. Storage location
5. Maximum number of clusters
6. Entity type(s)
7. Entity
8. Measure When bots in block 304 have identified and stored regime assignments for all time periods with measure data for the current entity, processing advances to a software block 305.

The software in block 305 checks the bot date table (163) and deactivates variable clustering bots with creation dates before the current system date. The software in block 305 then initializes bots in order for each element, resource and factor for the current entity. The bots activate in accordance with the frequency specified by the user (40) in the system settings table (162), retrieve the information from the element layer table (141), the transaction layer table (142), the resource layer table (143), the environment layer table (149) and the subject schema table (157) in order and define segments for element, resource and factor data before tagging and saving the resulting cluster information in the relationship layer table (144).

Bots are independent components of the application software of the present invention that complete specific tasks. In the case of variable clustering bots, their primary task is to segment the element, resource and factor data—including performance indicators—into distinct clusters that share similar characteristics. The clustering bot assigns a unique id number to each "cluster" it identifies, tags and stores the unique id numbers in the relationship layer table (144). Every item variable for each element, resource and factor is assigned to one of the unique clusters. The element data, resource data and factor data are segmented into a number of clusters less than or equal to the maximum specified by the user (40) in the system settings table (162). The data are segmented using several clustering algorithms including: an unsupervised "Kohonen" neural network, decision tree, context distance, support vector method, K-nearest neighbor, expectation maximization (EM) and the segmental K-means algorithm. For algorithms that normally use the specified number of clusters the bot will use the maximum number of clusters specified by the user (40) in the system settings table (162). Every variable clustering bot contains the information shown in Table 26.

TABLE 26

| | |
|---|---|
| 1. | Unique ID number (based on date, hour, minute, second of creation) |
| 2. | Creation date (date, hour, minute, second) |
| 3. | Mapping information |
| 4. | Storage location |
| 5. | Context component |
| 6. | Clustering algorithm type |
| 7. | Entity type(s) |
| 8. | Entity |
| 9. | Measure |
| 10. | Maximum number of clusters |
| 11. | Variable 1 |
| ... to | |
| 11 + n. | Variable n |

When bots in block 305 have identified, tagged and stored cluster assignments for the data associated with every element, resource and factor in the relationship layer table (144), processing advances to a software block 307.

The software in block 307 checks the measure layer table (145) in the contextbase (50) to see if the current measure is an options based measure like contingent liabilities, real options or competitor risk. If the current measure is not an options based measure, then processing advances to a software block 309. Alternatively, if the current measure is an options based measure, then processing advances to a software block 308.

The software in block 308 checks the bot date table (163) and deactivates option bots with creation dates before the current system date. The software in block 308 then retrieves the information from the system settings table (162), the subject schema table (157) and the element layer table (141), the transaction layer table (142), the resource layer table (143), the relationship layer table (144), the environment layer table (149) and the scenarios table (168) in order to initialize option bots in accordance with the frequency specified by the user (40) in the system settings table (162).

Bots are independent components of the application software of the present invention that complete specific tasks. In the case of option bots, their primary task is to determine the impact of each element, resource and factor on the entity option measure under different scenarios. The option simulation bots run a normal scenario, an extreme scenario and a combined scenario with and without clusters. In one embodiment, Monte Carlo models are used to complete the probabilistic simulation, however other option models including binomial models, multinomial models and dynamic programming can be used to the same effect. The element, resource and factor impacts on option measures could be determined using the process detailed below for the other types of measures. However, in the one preferred embodiment being described herein, a separate procedure is used. Every option bot activated in this block contains the information shown in Table 27.

TABLE 27

| |
|---|
| 1. Unique ID number (based on date, hour, minute, second of creation) |
| 2. Creation date (date, hour, minute, second) |
| 3. Mapping information |
| 4. Storage location |
| 5. Scenario: normal, extreme or combined |
| 6. Option type: real option, contingent liability or competitor risk |
| 7. Entity type(s) |
| 8. Entity |
| 9. Measure |
| 10. Clustered data? (yes or no) |
| 11. Algorithm |

After the option bots are initialized, they activate in accordance with the frequency specified by the user (40) in the system settings table (162). Once activated, the bots retrieve the specified information and simulate the measure over the time periods specified by the user (40) in the system settings table (162) in order to determine the impact of each element, resource and factor on the option. After the option bots complete their calculations, the impacts and sensitivities for the option (clustered data—yes or no) that produced the best result under each scenario are saved in the measure layer table (145) in the contextbase (50) and processing returns to software block 301.

If the current measure was not an option measure, then processing advanced to software block 309. The software in block 309 checks the bot date table (163) and deactivates all predictive model bots with creation dates before the current system date. The software in block 309 then retrieves the information from the system settings table (162), the subject schema table (157), the element layer table (141), the transaction layer table (142), the resource layer table (143), the relationship layer table (144) and the environment layer table (149) in order to initialize predictive model bots for each measure layer.

Bots are independent components of the application software that complete specific tasks. In the case of predictive model bots, their primary task is to determine the relationship between the indicators and the one or more measures being evaluated. Predictive model bots are initialized for each cluster and regime of data in accordance with the cluster and regime assignments specified by the bots in blocks 304 and 305. A series of predictive model bots is initialized at this stage because it is impossible to know in advance which predictive model type will produce the "best" predictive model for the data from each entity. The series for each model includes: neural network, CART, GARCH, constraint net, projection pursuit regression, stepwise regression, logistic regression, probit regression, factor analysis, growth modeling, linear regression, redundant regression network, boosted Naive Bayes Regression, support vector method, markov models, kriging, multivalent models, Gillespie models, relevance vector method, MARS, rough-set analysis and generalized additive model (GAM). Other types predictive models can be used to the same effect. Every predictive model bot contains the information shown in Table 28.

TABLE 28

1. Unique ID number (based on date, hour, minute, second of creation)
2. Creation date (date, hour, minute, second)
3. Mapping information
4. Storage location
5. Entity type(s)
6. Entity
7. Measure
8. Type: cluster, regime, cluster & regime
9. Predictive model type After predictive model bots are initialized, the bots activate in accordance with the frequency specified by the user (40) in the system settings table (162). Once activated, the bots retrieve the specified data from the appropriate table in the contextbase (50) and randomly partition the element, resource or factor data into a training set and a test set. The software in block 309 uses "bootstrapping" where the different training data sets are created by re-sampling with replacement from the original training set so data records may occur more than once. Training with genetic algorithms can also be used. After the predictive model bots in the tournament complete their training and testing, the best fit predictive model assessments of element, resource and factor impacts on measure performance are saved in the measure layer table (145) before processing advances to a block 310.

The software in block 310 determines if clustering improved the accuracy of the predictive models generated by the bots in software block 309 by entity. The software in block 310 uses a variable selection algorithm such as stepwise regression (other types of variable selection algorithms can be used) to combine the results from the predictive model bot analyses for each type of analysis—with and without clustering—to determine the best set of variables for each type of analysis. The type of analysis having the smallest amount of error as measured by applying the root mean squared error algorithm to the test data is given preference in determining the best set of variables for use in later analysis. Other error algorithms including entropy measures may also be used. There are four possible outcomes from this analysis as shown in Table 29.

TABLE 29

1. Best model has no clustering
2. Best model has temporal clustering, no variable clustering
3. Best model has variable clustering, no temporal clustering
4. Best model has temporal clustering and variable clustering If the software in block 310 determines that clustering improves the accuracy of the predictive models for an entity, then processing advances to a software block 314. Alternatively, if clustering does not improve the overall accuracy of the predictive models for an entity, then processing advances to a software block 312.

The software in block 312 uses a variable selection algorithm such as stepwise regression (other types of variable selection algorithms can be used) to combine the results from the predictive model bot analyses for each model. The models having the smallest amount of error, as measured by applying the root mean squared error algorithm to the test data, are given preference in determining the best set of variables. Other error algorithms including entropy measures may also be used. As a result of this processing, the best set of variables contain the variables (aka element, resource and factor data), indicators and composite variables that correlate most strongly with changes in the measure being analyzed. The best set of variables will hereinafter be referred to as the "performance drivers".

Eliminating low correlation factors from the initial configuration of the vector creation algorithms increases the efficiency of the next stage of system processing. Other error algorithms including entropy measures may be substituted for the root mean squared error algorithm. After the best set of variables have been selected, tagged and stored in the relationship layer table (144) for each entity, the software in block 312 tests the independence of the performance drivers for each entity before processing advances to a block 313.

The software in block 313 checks the bot date table (163) and deactivates causal predictive model bots with creation dates before the current system date. The software in block 313 then retrieves the information from the system settings table (162), the subject schema table (157), the element layer table (141), the transaction layer table (142), the resource layer table (143), the relationship layer table (144) and the environment layer table (149) in order to initialize causal predictive model bots for each element, resource and factor in accordance with the frequency specified by the user (40) in the system settings table (162). Sub-context elements, resources and factors may be used in the same manner.

Bots are independent components of the application software that complete specific tasks. In the case of causal predictive model bots, their primary task is to refine the performance driver selection to reflect only causal variables. A series of causal predictive model bots are initialized at this stage because it is impossible to know in advance which causal predictive model will produce the "best" vector for the best fit variables from each model. The series for each model includes a number of causal predictive model bot types: Tetrad, MML, LaGrange, Bayesian, Probabilistic Relational Model (if allowed), Impact Factor Majority and path analysis. The Bayesian bots in this step also refine the estimates of element, resource and/or factor impact developed by the predictive model bots in a prior processing step by assigning a probability to the impact estimate. The software in block 313 generates this series of causal predictive model bots for each set of performance drivers stored in the relationship layer table (144) in the previous stage in processing. Every causal predictive model bot activated in this block contains the information shown in Table 30.

TABLE 30

1. Unique ID number (based on date, hour, minute, second of creation)
2. Creation date (date, hour, minute, second)
3. Mapping information
4. Storage location
5. Causal predictive model type
6. Entity type(s)
7. Entity
8. Measure After the causal predictive model bots are initialized by the software in block 313, the bots activate in accordance with the frequency specified by the user (40) in the system settings table (162). Once activated, they retrieve the specified information for each model and sub-divide the variables into two sets, one for training and one for testing. After the causal predictive model bots complete their processing for each model, the software in block 313 uses a model selection algorithm to identify the model that best fits the data. For the system of the present invention, a cross validation algorithm is used for model selection. The software in block 313 then saves the refined impact estimates in the measure layer table (145) and the best fit causal element, resource and/or factor indicators are identified in the relationship layer table (144) in the contextbase (50) before processing returns to software block 301.

If software in block 310 determines that clustering improves predictive model accuracy, then processing advances directly to block 314 as described previously. The software in block 314 uses a variable selection algorithm such as stepwise regression (other types of variable selection algorithms can be used) to combine the results from the predictive model bot analyses for each model, cluster and/or regime to determine the best set of variables for each model. The models having the smallest amount of error as measured by applying the root mean squared error algorithm to the test data are given preference in determining the best set of variables. Other error algorithms including entropy measures may also be used. As a result of this processing, the best set of variables contains: the element data and factor data that correlate most strongly with changes in the function measure. The best set of variables will hereinafter be referred to as the "performance drivers". Eliminating low correlation factors from the initial configuration increases the efficiency of the next stage of system processing. Other error algorithms including entropy measures may be substituted for the root mean squared error algorithm. After the best set of variables have been selected, they are tagged as performance drivers and stored in the relationship layer table (144), the software in block 314 tests the independence of the performance drivers before processing advances to a block 315.

The software in block 315 checks the bot date table (163) and deactivates causal predictive model bots with creation dates before the current system date. The software in block 315 then retrieves the information from the system settings table (162), the subject schema table (157), the element layer table (141), the transaction layer table (142), the resource layer table (143), the relationship layer table (144) and the environment layer table (149) in order to initialize causal predictive model bots in accordance with the frequency specified by the user (40) in the system settings table (162). Bots are independent components of the application software of the present invention that complete specific tasks. In the case of causal predictive model bots, their primary task is to refine the element, resource and factor performance driver selection to reflect only causal variables. (Note: these variables are grouped together to represent a single element vector when they are dependent). In some cases it may be possible to skip the correlation step before selecting causal item variables, factor variables, indicators, and composite variables. A series of causal predictive model bots are initialized at this stage because it is impossible to know in advance which causal predictive model will produce the "best" vector for the best fit variables from each model. The series for each model includes: Tetrad, LaGrange, Bayesian, Probabilistic Relational Model and path analysis. The Bayesian bots in this step also refine the estimates of element or factor impact developed by the predictive model bots in a prior processing step by assigning a probability to the impact estimate. The software in block 315 generates this series of causal predictive model bots for each set of performance drivers stored in the subject schema table (157) in the previous stage in processing. Every causal predictive model bot activated in this block contains the information shown in Table 31.

TABLE 31

1. Unique ID number (based on date, hour, minute, second of creation)
2. Creation date (date, hour, minute, second)
3. Mapping information
4. Storage location
5. Type: cluster, regime, cluster & regime
5. Entity type(s)
6. Entity
7. Measure
8. Causal predictive model type After the causal predictive model bots are initialized by the software in block 315, the bots activate in accordance with the frequency specified by the user (40) in the system settings table (162). Once activated, they retrieve the specified information for each model and subdivide the variables into two sets, one for training and one for testing. The same set of training data are used by each of the different types of bots for each model. After the causal predictive model bots complete their processing for each model, the software in block 315 uses a model selection algorithm to identify the model that best fits the data for each element, resource and factor being analyzed by model and/or regime by entity. For the system of the present invention, a cross validation algorithm is used for model selection. The software in block 315 saves the refined impact estimates in the measure layer table (145) and identifies the best fit causal element, resource and/or factor indicators in the relationship layer table (144) in the contextbase (50) before processing returns to software block 301.

When the software in block 301 determines that all measure models are current, then processing advances to a software block 322. The software in block 322 checks the measure layer table (145) and the event model table (158) in the contextbase (50) to determine if all event models are current. If all event models are current, then processing advances to a software block 332. Alternatively, if new event models need to be developed, then processing advances to a software block 325. The software in block 325 retrieves information from the system settings table (162), the subject schema table (157), the element layer table (141), the transaction layer table (142), the resource layer table (143), the relationship layer table (144), the environment layer table (149) and the event model table (158) in order to complete summaries of event history and forecasts before processing advances to a software block 304 where the processing sequence described above (save for the option bot processing)—is used to identify drivers for event frequency. After all event frequency models have been developed they are stored in the event model table (158), processing advances to a software block 332.

The software in block 332 checks the measure layer table (145) and impact model table (166) in the contextbase (50) to determine if impact models are current for all event risks and transactions. If all impact models are current, then processing advances to a software block 341. Alternatively, if new impact models need to be developed, then processing advances to a software block 335. The software in block 335 retrieves information from the system settings table (162), the subject schema table (157), the element layer table (141), the transaction layer table (142), the resource layer table (143), the relationship layer table (144), the environment layer table (149) and the impact model table (166) in order to complete summaries of impact history and forecasts before processing advances to a software block 304 where the processing sequence described above—save for the option bot processing—is used to identify drivers for event and action impact (or magnitude). After impact models have been developed for all event risks and transaction impacts they are stored in the impact model table (166) and processing advances to a software block 341.

If a spatial coordinate system is being used, then processing advances to a block 341 before the processing described above begins. The software in block 341 checks the subject schema table (157) in the contextbase (50) to determine if spatial data is being used. If spatial data is being used, then processing advances to a software block 342. Alternatively, if all spatial data are not being used, then processing advances to a software block 370.

The software in block 342 checks the measure layer table (145) in the contextbase (50) to determine if there are current models for all spatial measures for every entity level. If all measure models are current, then processing advances to a software block 356. Alternatively, if all spatial measure models are not current, then processing advances to a software block 303. The software in block 303 retrieves the previously calculated values for the measure from the measure layer table (145) before processing advances to software block 304.

The software in block 304 checks the bot date table (163) and deactivates temporal clustering bots with creation dates before the current system date. The software in block 304 then initializes bots in accordance with the frequency specified by the user (40) in the system settings table (162). The bots retrieve information from the measure layer table (145) for the entity being analyzed and defines regimes for the measure being analyzed before saving the resulting cluster information in the relationship layer table (144) in the contextbase (50). Bots are independent components of the application software of the present invention that complete specific tasks. In the case of temporal clustering bots, their primary task is to segment measure performance into distinct time regimes that share similar characteristics. The temporal clustering bot assigns a unique identification (id) number to each "regime" it identifies before tagging and storing the unique id numbers in the relationship layer table (144). Every time period with data is assigned to one of the regimes. The cluster id for each regime is associated with the measure and entity being analyzed. The time regimes are developed using a competitive regression algorithm that identifies an overall, global model before splitting the data and creating new models for the data in each partition. If the error from the two models is greater than the error from the global model, then there is only one regime in the data. Alternatively, if the two models produce lower error than the global model, then a third model is created. If the error from three models is lower than from two models then a fourth model is added. The processing continues until adding a new model does not improve accuracy. Other temporal clustering algorithms may be used to the same effect. Every temporal clustering bot contains the information shown in Table 32.

TABLE 32

1. Unique ID number (based on date, hour, minute, second of creation)
2. Creation date (date, hour, minute, second)
3. Mapping information
4. Storage location
5. Maximum number of clusters
6. Entity type(s)
7. Entity
8. Measure When bots in block 304 have identified and stored regime assignments for all time periods with measure data for the current entity, processing advances to a software block 305.

The software in block 305 checks the bot date table (163) and deactivates variable clustering bots with creation dates before the current system date. The software in block 305 then initializes bots in order for each context element, resource and factor for the current entity level. The bots activate in accordance with the frequency specified by the user (40) in the system settings table (162), retrieve the information from the element layer table (141), the transaction layer table (142), the resource layer table (143), the environment layer table (149) and the subject schema table (157) and define segments for context element, resource and factor data before tagging and saving the resulting cluster information in the relationship layer table (144). Bots are independent components of the application software of the present invention that complete specific tasks. In the case of variable clustering bots, their primary task is to segment the element, resource and factor data—including indicators—into distinct clusters that share similar characteristics. The clustering bot assigns a unique id number to each "cluster" it identifies, tags and stores the unique id numbers in the relationship layer table (144). Every variable for every context element, resource and factor is assigned to one of the unique clusters. The element data, resource data and factor data are segmented into a number of clusters less than or equal to the maximum specified by the user (40) in the system settings table (162). The data are segmented using several clustering algorithms including: an unsupervised "Kohonen" neural network, decision tree, support vector method, K-nearest neighbor, expectation maximization (EM) and the segmental K-means algorithm. For algorithms that normally have the number of clusters specified by a user, the bot will use the maximum number of clusters specified by the user (40). Every variable clustering bot contains the information shown in Table 33.

TABLE 33

| 1. | Unique ID number (based on date, hour, minute, second of creation) |
|---|---|
| 2. | Creation date (date, hour, minute, second) |
| 3. | Mapping information |
| 4. | Storage location |
| 5. | Context component |
| 6. | Clustering algorithm |
| 7. | Entity type(s) |
| 8. | Entity |
| 9. | Measure |
| 10. | Maximum number of clusters |
| 11. | Variable 1 |
| ... to | |
| 11 + n. | Variable n |

When bots in block 305 have identified, tagged and stored cluster assignments for the data associated with every element, resource and factor in the relationship layer table (144), processing advances to a software block 343.

The software in block 343 checks the bot date table (163) and deactivates spatial clustering bots with creation dates before the current system date. The software in block 343 then retrieves the information from the system settings table (162), the subject schema table (157), the element layer table (141), the transaction layer table (142), the resource layer table (143), the relationship layer table (144), the environment layer table (149), the reference layer table (154) and the scenarios table (168) in order to initialize spatial clustering bots in accordance with the frequency specified by the user (40) in the system settings table (162). Bots are independent components of the application software that complete specific tasks. In the case of spatial clustering bots, their primary task is to segment the element, resource and factor data— including performance indicators—into distinct clusters that share similar characteristics. The clustering bot assigns a unique id number to each "cluster" it identifies, tags and stores the unique id numbers in the relationship layer table (144). Data for each context element, resource and factor are assigned to one of the unique clusters. The element, resource and factor data are segmented into a number of clusters less than or equal to the maximum specified by the user (40) in the system settings table (162). The system of the present invention uses several spatial clustering algorithms including: hierarchical clustering, cluster detection, k-ary clustering, variance to mean ratio, lacunarity analysis, pair correlation, join correlation, mark correlation, fractal dimension, wavelet, nearest neighbor, local index of spatial association (LISA), spatial analysis by distance indices (SADIE), mantel test and circumcircle. Every spatial clustering bot activated in this block contains the information shown in Table 34.

TABLE 34

| | |
|---|---|
| 1. | Unique ID number (based on date, hour, minute, second of creation) |
| 2. | Creation date (date, hour, minute, second) |
| 3. | Mapping information |
| 4. | Storage location |
| 5. | Context component |
| 6. | Clustering algorithm |
| 7. | Entity type(s) |
| 8. | Entity |
| 9. | Measure |
| 10. | Maximum number of clusters |
| 11. | Variable 1 |
| ... to | |
| 11 + n. | Variable n |

When bots in block 343 have identified, tagged and stored cluster assignments for the data associated with every element, resource and factor in the relationship layer table (144), processing advances to a software block 307.

The software in block 307 checks the measure layer table (145) in the contextbase (50) to see if the current measure is an options based measure like contingent liabilities, real options or competitor risk. If the current measure is not an options based measure, then processing advances to a software block 344. Alternatively, if the current measure is an options based measure, then processing advances to a software block 308.

The software in block 308 checks the bot date table (163) and deactivates option bots with creation dates before the current system date. The software in block 308 then retrieves the information from the system settings table (162), the subject schema table (157), the element layer table (141), the transaction layer table (142), the resource layer table (143), the relationship layer table (144), the environment layer table (149), the reference layer table (154) and the scenarios table (168) in order to initialize option bots in accordance with the frequency specified by the user (40) in the system settings table (162).

Bots are independent components of the application software of the present invention that complete specific tasks. In the case of option bots, their primary task is to determine the impact of each element, resource and factor on the entity option measure under different scenarios. The option simulation bots run a normal scenario, an extreme scenario and a combined scenario with and without clusters. In one embodiment, Monte Carlo models are used to complete the probabilistic simulation. However, other option models including binomial models, multinomial models and dynamic programming can be used to the same effect. The element, resource and factor impacts on option measures could be determined using the processed detailed below for the other types of measures, however, in this embodiment a separate procedure is used. The models are initialized with specifications used in the baseline calculations. Every option bot activated in this block contains the information shown in Table 35.

TABLE 35

| | |
|---|---|
| 1. | Unique ID number (based on date, hour, minute, second of creation) |
| 2. | Creation date (date, hour, minute, second) |
| 3. | Mapping information |
| 4. | Storage location |
| 5. | Scenario: normal, extreme or combined |
| 6. | Option type: real option, contingent liability or competitor risk |
| 7. | Entity type(s) |
| 8. | Entity |
| 9. | Measure |
| 10. | Clustered data? (Yes or No) |
| 11. | Algorithm |

After the option bots are initialized, they activate in accordance with the frequency specified by the user (40) in the system settings table (162). Once activated, the bots retrieve the specified information and simulate the measure over the time periods specified by the user (40) in the system settings table (162) in order to determine the impact of each element, resource and factor on the option. After the option bots complete their calculations, the impacts and sensitivities for the option (clustered data—yes or no) that produced the best result under each scenario are saved in the measure layer table (145) in the contextbase (50) and processing returns to software block 341.

If the current measure was not an option measure, then processing advanced to software block 344. The software in block 309 checks the bot date table (163) and deactivates all predictive model bots with creation dates before the current system date. The software in block 344 then retrieves the information from the system settings table (162), the subject schema table (157) and the element layer table (141), the transaction layer table (142), the resource layer table (143), the relationship layer table (144), the environment layer table (149) and the reference layer (154) in order to initialize predictive model bots for the measure being evaluated.

Bots are independent components of the application software that complete specific tasks. In the case of predictive model bots, their primary task is to determine the relationship between the indicators and the measure being evaluated. Predictive model bots are initialized for each cluster and/or regime of data in accordance with the cluster and/or regime assignments specified by the bots in blocks 304, 305 and 343. A series of predictive model bots is initialized at this stage because it is impossible to know in advance which predictive model type will produce the "best" predictive model for the data from each entity. The series for each model includes: neural network, CART, GARCH, projection pursuit regression, stepwise regression, logistic regression, probit regression, factor analysis, growth modeling, linear regression, redundant regression network, boosted naive bayes regression, support vector method, markov models, rough-set analysis, kriging, simulated annealing, latent class models, gaussian mixture models, triangulated probability and kernel estimation. Each model includes spatial autocorrelation indicators as performance indicators. Other types predictive models can be used to the same effect. Every predictive model bot contains the information shown in Table 36.

TABLE 36

1. Unique ID number (based on date, hour, minute, second of creation)
2. Creation date (date, hour, minute, second)
3. Mapping information
4. Storage location
5. Entity type(s)
6. Entity
7. Measure
8. Type: variable (y or n), spatial (y or n), spatial-temporal (y or n)
9. Predictive model type After predictive model bots are initialized, the bots activate in accordance with the frequency specified by the user (40) in the system settings table (162). Once activated, the bots retrieve the specified data from the appropriate table in the contextbase (50) and randomly partition the element, resource and/or factor data into a training set and a test set. The software in block 344 uses "bootstrapping" where the different training data sets are created by re-sampling with replacement from the original training set so data records may occur more than once. Training with genetic algorithms can also be used. After the predictive model bots complete their training and testing, the best fit predictive model assessments of element, resource and factor impacts on measure performance are saved in the measure layer table (145) before processing advances to a block 345.

The software in block 345 determines if clustering improved the accuracy of the predictive models generated by the bots in software block 344. The software in block 345 uses a variable selection algorithm such as stepwise regression (other types of variable selection algorithms can be used) to combine the results from the predictive model bot analyses for each type of analysis—with and without clustering—to determine the best set of variables for each type of analysis. The type of analysis having the smallest amount of error as measured by applying the root mean squared error algorithm to the test data are given preference in determining the best set of variables for use in later analysis. Other error algorithms including entropy measures may also be used. There are eight possible outcomes from this analysis as shown in Table 37.

TABLE 37

1. Best model has no clustering
2. Best model has temporal clustering, no variable clustering, no spatial clustering
3. Best model has variable clustering, no temporal clustering, no spatial clustering
4. Best model has temporal clustering, variable clustering, no spatial clustering
5. Best model has no temporal clustering, no variable clustering, spatial clustering
6. Best model has temporal clustering, no variable clustering, spatial clustering
7. Best model has variable clustering, no temporal clustering, spatial clustering
8. Best model has temporal clustering, variable clustering, spatial clustering If the software in block 345 determines that clustering improves the accuracy of the predictive models for an entity, then processing advances to a software block 348. Alternatively, if clustering does not improve the overall accuracy of the predictive models for an entity, then processing advances to a software block 346.

The software in block 346 uses a variable selection algorithm such as stepwise regression (other types of variable selection algorithms can be used) to combine the results from the predictive model bot analyses for each model to determine the best set of variables for each model. The models having the smallest amount of error, as measured by applying the root mean squared error algorithm to the test data, are given preference in determining the best set of variables. Other error algorithms including entropy measures may also be used. As a result of this processing, the best set of variables contain the variables (aka element, resource and factor data), indicators, and composite variables that correlate most strongly with changes in the measure being analyzed. The best set of variables will hereinafter be referred to as the "performance drivers".

Eliminating low correlation factors from the initial configuration of the vector creation algorithms increases the efficiency of the next stage of system processing. Other error algorithms including entropy measures may be substituted for the root mean squared error algorithm. After the best set of variables have been selected, tagged and stored in the relationship layer table (144) for each entity level, the software in block 346 tests the independence of the performance drivers for each entity level before processing advances to a block 347.

The software in block 347 checks the bot date table (163) and deactivates causal predictive model bots with creation dates before the current system date. The software in block 347 then retrieves the information from the system settings table (162), the subject schema table (157), the element layer table (141), the transaction layer table (142), the resource layer table (143), the relationship layer table (144) and the environment layer table (149) in order to initialize causal predictive model bots for each element, resource and factor in accordance with the frequency specified by the user (40) in the system settings table (162). Sub-context elements, resources and factors may be used in the same manner.

Bots are independent components of the application software that complete specific tasks. In the case of causal predictive model bots, their primary task is to refine the performance driver selection to reflect only causal variables. A series of causal predictive model bots are initialized at this stage because it is impossible to know in advance which causal predictive model will produce the "best" fit for variables from each model. The series for each model includes six causal predictive model bot types: kriging, latent class models, gaussian mixture models, kernel estimation and Markov-Bayes. The software in block 347 generates this series of causal predictive model bots for each set of performance drivers stored in the relationship layer table (144) in the previous stage in processing. Every causal predictive model bot activated in this block contains the information shown in Table 38.

TABLE 38

1. Unique ID number (based on date, hour, minute, second of creation)
2. Creation date (date, hour, minute, second)
3. Mapping information
4. Storage location
5. Causal predictive model type
6. Entity type(s)
7. Entity
8. Measure After the causal predictive model bots are initialized by the software in block 347, the bots activate in accordance with the frequency specified by the user (40) in the system settings table (162). Once activated, they retrieve the specified information for each model and sub-divide the variables into two sets, one for training and one for testing. After the causal predictive model bots complete their processing for each model, the software in block 347 uses a model selection algorithm to identify the model that best fits the data. For the system of the present invention, a cross validation algorithm is used for model selection. The software in block 347 then saves the refined impact estimates in the measure layer table (145) and the best fit causal element, resource and/or factor indicators are identified in the relationship layer table (144) in the contextbase (50) before processing returns to software block 342.

If software in block 345 determines that clustering improves predictive model accuracy, then processing advances directly to block 348 as described previously. The software in block 348 uses a variable selection algorithm such as stepwise regression (other types of variable selection algorithms can be used) to combine the results from the predictive model bot analyses for each model, cluster and/or regime to determine the best set of variables for each model. The models having the smallest amount of error as measured by applying the root mean squared error algorithm to the test data are given preference in determining the best set of variables. Other error algorithms including entropy measures can also be used. As a result of this processing, the best set of variables contains the element data, resource data and factor data that correlate most strongly with changes in the function and/or mission measures. The best set of variables will hereinafter be referred to as the "performance drivers". Eliminating low correlation factors from the initial configuration of the vector creation algorithms increases the efficiency of the next stage of system processing. Other error algorithms including entropy measures may be substituted for the root mean squared error algorithm. After the best set of variables have been selected, they are tagged as performance drivers and stored in the relationship layer table (144), the software in block 348 tests the independence of the performance drivers before processing advances to a block 349.

The software in block 349 checks the bot date table (163) and deactivates causal predictive model bots with creation dates before the current system date. The software in block 349 then retrieves the information from the system settings table (162), the subject schema table (157), the element layer table (141), the transaction layer table (142), the resource layer table (143), the relationship layer table (144) and the environment layer table (149) in order to initialize causal predictive model bots in accordance with the frequency specified by the user (40) in the system settings table (162). Bots are independent components of the application software of the present invention that complete specific tasks. In the case of causal predictive model bots, their primary task is to refine the element, resource and factor performance driver selection to reflect only causal variables. (Note: these variables are grouped together to represent a single vector when they are dependent). In some cases it may be possible to skip the correlation step before selecting causal the item variables, factor variables, indicators and composite variables. A series of causal predictive model bots are initialized at this stage because it is impossible to know in advance which causal predictive model will produce the "best" fit variables for each measure. The series for each measure includes six causal predictive model bot types: kriging, latent class models, gaussian mixture models, kernel estimation and Markov-Bayes. The software in block 349 generates this series of causal predictive model bots for each set of performance drivers stored in the subject schema table (157) in the previous stage in processing. Every causal predictive model bot activated in this block contains the information shown in Table 39.

TABLE 39

1. Unique ID number (based on date, hour, minute, second of creation)
2. Creation date (date, hour, minute, second)
3. Mapping information
4. Storage location
5. Type: cluster, regime, cluster & regime
6. Entity type(s)
7. Entity
8. Measure
9. Causal predictive model type After the causal predictive model bots are initialized by the software in block 349, the bots activate in accordance with the frequency specified by the user (40) in the system settings table (162). Once activated, they retrieve the specified information for each model and sub-divide the variables into two sets, one for training and one for testing. The same set of training data is used by each of the different types of bots for each model. After the causal predictive model bots complete their processing for each model, the software in block 349 uses a model selection algorithm to identify the model that best fits the data for each process, element, resource and/or factor being analyzed by model and/or regime by entity. For the system of the present invention, a cross validation algorithm is used for model selection. The software in block 349 saves the refined impact estimates in the measure layer table (145) and identifies the best fit causal element, resource and/or factor indicators in the relationship layer table (144) in the contextbase (50) before processing returns to software block 342.

When the software in block 342 determines that all spatial measure models are current processing advances to a software block 356. The software in block 356 checks the measure layer table (145) and the event model table (158) in the contextbase (50) to determine if all event models are current. If all event models are current, then processing advances to a software block 361. Alternatively, if new event models need to be developed, then processing advances to a software block 325. The software in block 325 retrieves information from the system settings table (162), the subject schema table (157), the element layer table (141), the transaction layer table (142), the resource layer table (143), the relationship layer table (144), the environment layer table (149), the reference layer table (154) and the event model table (158) in order to complete summaries of event history and forecasts before processing advances to a software block 304 where the processing sequence described above—save for the option bot processing—is used to identify drivers for event risk and transaction frequency. After all event frequency models have been developed they are stored in the event model table (158) and processing advances to software block 361.

The software in block 361 checks the measure layer table (145) and impact model table (166) in the contextbase (50) to determine if impact models are current for all event risks and actions. If all impact models are current, then processing advances to a software block 370. Alternatively, if new impact models need to be developed, then processing advances to a software block 335. The software in block 335 retrieves information from the system settings table (162), the subject schema table (157), the element layer table (141), the transaction layer table (142), the resource layer table (143), the relationship layer table (144), the environment layer table (149)), the reference layer table (154) and the impact model table (166) in order to complete summaries of impact history and forecasts before processing advances to a software block 305 where the processing sequence described above—save for the option bot processing—is used to identify drivers for event risk and transaction impact (or magnitude). After impact models have been developed for all event risks and action impacts they are stored in the impact model table (166) and processing advances to a software block 370 via software block 361.

The software in block 370 determines if adding spatial data improves the accuracy of the predictive models. The software in block 370 uses a variable selection algorithm such as stepwise regression (other types of variable selection algorithms can be used) to combine the results from each type of prior analysis—with and without spatial data—to determine the best set of variables for each type of analysis. The type of analysis having the smallest amount of error as measured by applying the root mean squared error algorithm to the test data are used for subsequent later analysis. Other error algorithms including entropy measures may also be used. There are eight possible outcomes from this analysis as shown in Table 40.

TABLE 40

1. Best measure, event and impact models are spatial
2. Best measure and event models are spatial, best impact model is not spatial
3. Best measure and impact models are spatial, best event model is not spatial
5. Best measure models are spatial, best event and impact models are not spatial
5. Best measure models are not spatial, best event and impact models are spatial
6. Best measure and impact models are not spatial, best event model is spatial
7. Best measure and event models are not spatial, best impact model is spatial
8. Best measure, event and impact models are not spatial The best set of models identified by the software in block 370 are tagged for use in subsequent processing before processing advances to a software block 371.

The software in block 371 checks the measure layer table (145) in the contextbase (50) to determine if probabilistic relational models were used in measure impacts. If probabilistic relational models were used, then processing advances to a software block 377. Alternatively, if probabilistic relational models were not used, then processing advances to a software block 372.

The software in block 372 tests the performance drivers to see if there is interaction between elements, factors and/or resources by entity. The software in this block identifies interaction by evaluating a chosen model based on stochastic-driven pairs of value-driver subsets. If the accuracy of such a model is higher that the accuracy of statistically combined models trained on attribute subsets, then the attributes from subsets are considered to be interacting and then they form an interacting set. Other tests of driver interaction can be used to the same effect. The software in block 372 also tests the performance drivers to see if there are "missing" performance drivers that are influencing the results. If the software in block 372 does not detect any performance driver interaction or missing variables for each entity, then system processing advances to a block 376. Alternatively, if missing data or performance driver interactions across elements, factors and/or resources are detected by the software in block 372 for one or more measures, processing advances to a software block 373.

The software in block 373 evaluates the interaction between performance drivers in order to classify the performance driver set. The performance driver set generally matches one of the six patterns of interaction: a multi-component loop, a feed forward loop, a single input driver, a multi-input driver, auto-regulation or a chain. After classifying each performance driver set the software in block 373 prompts the user (40) via the structure revision window (706) to accept the classification and continue processing, establish probabilistic relational models as the primary causal model and/or adjust the specification(s) for the context elements and factors in some other way in order to minimize or eliminate interaction that was identified. For example, the user (40) can also choose to re-assign a performance driver to a new context element or factor to eliminate an identified inter-dependency. After the optional input from the user (40) is saved in the element layer table (141), the environment layer table (149) and the system settings table (162), processing advances to a software block 374. The software in block 374 checks the element layer table (141), the environment layer table (149) and system settings table (162) to see if there are any changes in structure. If there have been changes in the structure, then processing returns to block 201 and the system processing described previously is repeated. Alternatively, if there are no changes in structure, then the information regarding the element interaction is saved in the relationship layer table (144) before processing advances to a block 376.

The software in block 376 checks the bot date table (163) and deactivates vector generation bots with creation dates before the current system date. The software in block 376 then initializes vector generation bots for each context element, sub-context element, element combination, factor combination, context factor and sub-context factor. The bots activate in accordance with the frequency specified by the user (40) in the system settings table (162) and retrieve information from the element layer table (141), the transaction layer table (142), the resource layer table (143), the relationship layer table (144) and the environment layer table (149). Bots are independent components of the application software that complete specific tasks. In the case of vector generation bots, their primary task is to produce vectors that summarize the relationship between the causal performance drivers and changes in the measure being examined. The vector generation bots use induction algorithms to generate the vectors. Other vector generation algorithms can be used to the same effect. Every vector generation bot contains the information shown in Table 41.

TABLE 41

| | |
|---|---|
| 1. | Unique ID number (based on date, hour, minute, second of creation) |
| 2. | Creation date (date, hour, minute, second) |
| 3. | Mapping information |
| 4. | Storage location |
| 5. | Hierarchy or group |
| 6. | Entity |
| 7. | Measure |
| 8. | Context component or combination |
| 9. | Factor 1 |
| . . . to | |
| 9 + n. | Factor n |

When bots in block 376 have created and stored vectors for all time periods with data for all the elements, sub-elements, factors, sub-factors, resources, sub-resources and combinations that have vectors in the subject schema table (157) by entity, processing advances to a software block 377.

The software in block 377 checks the bot date table (163) and deactivates life bots with creation dates before the current system date. The software in block 377 then retrieves the information from the system settings table (162), the element layer table (141), the transaction layer table (142), the resource layer table (143), the relationship layer table (144) and the environment layer table (149) in order to initialize life bots for each element and factor. Bots are independent components of the application software that complete specific tasks. In the case of life bots, their primary task is to determine the expected life of each element, resource and factor. There are three methods for evaluating the expected life:

1. Elements, resources and factors that are defined by a population of members or items (such as: channel partners, customers, employees and vendors) will have their lives estimated by forecasting the lives of members of the population and then integrating the results into an overall population density matrix. The forecast of member lives will be determined by the "best" fit solution from competing life estimation methods including the Iowa type survivor curves, Weibull distribution survivor curves, growth models, Gompertz-Makeham survivor curves, Bayesian population matrix estimation and polynomial equations using the tournament method for selecting from competing forecasts;
2. Elements, resources and factors (such as patents, long term supply agreements, certain laws and insurance contracts) that have legally defined lives will have their lives calculated using the time period between the current date and the expiration date of their defined life; and
3. Finally, elements, resources and factors that do not have defined lives will have their lives estimated to equal the forecast time period.

Every element life bot contains the information shown in Table 42.

TABLE 42

1. Unique ID number (based on date, hour, minute, second of creation)
2. Creation date (date, hour, minute, second)
3. Mapping information
4. Storage location
5. Hierarchy or group
6. Entity
7. Measure
8. Context component or combination
9. Life estimation method (item analysis, defined or forecast period)

After the life bots are initialized, they are activated in accordance with the frequency specified by the user (40) in the system settings table (162). After being activated, the bots retrieve information for each element and sub-context element from the contextbase (50) in order to complete the estimate of element life. The resulting values are then tagged and stored in the element layer table (141), the resource layer table (143) or the environment layer table (149) in the contextbase (50) before processing advances to a block 379.

The software in block 379 checks the bot date table (163) and deactivates dynamic relationship bots with creation dates before the current system date. The software in block 379 then retrieves the information from the system settings table (162), the element layer table (141), the transaction layer table (142), the resource layer table (143), the relationship layer table (144), the environment layer table (149) and the event risk table (156) in order to initialize dynamic relationship bots for the measure. Bots are independent components of the application software that complete specific tasks. In the case of dynamic relationship bots, their primary task is to identify the best fit dynamic model of the interrelationship between the different elements, factors, resources and events that are driving measure performance. The best fit model is selected from a group of potential linear models and non-linear models including swarm models, complexity models, maximal time step models, simple regression models, power law models and fractal models. Every dynamic relationship bot contains the information shown in Table 43.

TABLE 43

1. Unique ID number (based on date, hour, minute, second of creation)
2. Creation date (date, hour, minute, second)
3. Mapping information
4. Storage location
5. Hierarchy or group
6. Entity
7. Measure
8. Algorithm The bots in block 379 identify the best fit model of the dynamic interrelationship between the elements, factors, resources and risks for the reviewed measure and store information regarding the best fit model in the relationship layer table (144) before processing advances to a software block 380.

The software in block 380 checks the bot date table (163) and deactivates partition bots with creation dates before the current system date. The software in the block then retrieves the information from the system settings table (162), the element layer table (141), the transaction layer table (142), the resource layer table (143), the relationship layer table (144), the measure layer table (145), the environment layer table (149), the event risk table (156) and the scenarios table (168) to initialize partition bots in accordance with the frequency specified by the user (40) in the system settings table (162). Bots are independent components of the application software of the present invention that complete specific tasks. In the case of partition bots, their primary task is to use the historical and forecast data to segment the performance measure contribution of each element, factor, resource, combination and performance driver into a base value and a variability or risk component. The system of the present invention uses wavelet algorithms to segment the performance contribution into two components although other segmentation algorithms such as GARCH could be used to the same effect. Every partition bot contains the information shown in Table 44.

TABLE 44

1. Unique ID number (based on date, hour, minute, second of creation)
2. Creation date (date, hour, minute, second)
3. Mapping information
4. Storage location
5. Hierarchy or group
6. Entity
7. Measure
8. Context component or combination
9. Segmentation algorithm After the partition bots are initialized, the bots activate in accordance with the frequency specified by the user (40) in the system settings table (162). After being activated the bots retrieve data from the contextbase (50) and then segment the performance contribution of each element, factor, resource or combination into two segments. The resulting values by period for each entity are then stored in the measure layer table (145), before processing advances to a software block 382.

The software in block 382 retrieves the information from the event model table (158) and the impact model table (166) and combines the information from both tables in order to update the event risk estimate for the entity. The resulting values by period for each entity are then stored in the event risk table (156), before processing advances to a software block 389.

The software in block 389 checks the bot date table (163) and deactivates simulation bots with creation dates before the current system date. The software in block 389 then retrieves the information from the relationship layer table (144), the measure layer table (145), the event risk table (156), the subject schema table (157), the system settings table (162) and the scenarios table (168) in order to initialize simulation bots in accordance with the frequency specified by the user (40) in the system settings table (162).

Bots are independent components of the application software that complete specific tasks. In the case of simulation bots, their primary task is to run three different types of simulations of subject measure performance. The simulation bots run probabilistic simulations of measure performance using the normal scenario, the extreme scenario and the blended scenario. They also run an unconstrained genetic algorithm simulation that evolves to the most negative value possible over the specified time period. In one embodiment, Monte Carlo models are used to complete the probabilistic simulation, however other probabilistic simulation models such as Quasi Monte Carlo, genetic algorithm and Markov Chain Monte Carlo can be used to the same effect. The models are initialized using the statistics and relationships derived from the calculations completed in the prior stages of processing to relate measure performance to the performance driver, element, factor, resource and event risk scenarios. Every simulation bot activated in this block contains the information shown in Table 46.

TABLE 46

1. Unique ID number (based on date, hour, minute, second of creation)
2. Creation date (date, hour, minute, second)
3. Mapping information
4. Storage location
5. Type: normal, extreme, blended or genetic algorithm
6. Measure
7. Hierarchy or group
8. Entity After the simulation bots are initialized, they activate in accordance with the frequency specified by the user (40) in the system settings table (162). Once activated, they retrieve the specified information and simulate measure performance by entity over the time periods specified by the user (40) in the system settings table (162). In doing so, the bots will forecast the range of performance and risk that can be expected for the specified measure by entity within the confidence interval defined by the user (40) in the system settings table (162) for each scenario. The bots also create a summary of the overall risks facing the entity for the current measure. After the simulation bots complete their calculations, the resulting forecasts are saved in the scenarios table (168) by entity and the risk summary is saved in the report table (153) in the contextbase (50) before processing advances to a software block 390.

The software in block 390 checks the measure layer table (145) and the system settings table (162) in the contextbase (50) to see if probabilistic relational models were used. If probabilistic relational models were used, then processing advances to a software block 398. Alternatively, if the current calculations did not rely on probabilistic relational models, then processing advances to a software block 391.

The software in block 391 checks the bot date table (163) and deactivates measure bots with creation dates before the current system date. The software in block 391 then retrieves the information from the system settings table (162), the measure layer table (145) and the subject schema table (157) in order to initialize bots for each context element, context factor, context resource, combination or performance driver for the measure being analyzed. Bots are independent components of the application software of the present invention that complete specific tasks. In the case of measure bots, their task is to determine the net contribution of the network of elements, factors, resources, events, combinations and performance drivers to the measure being analyzed. The relative contribution of each element, factor, resource, combination and performance driver is determined by using a series of predictive models to find the best fit relationship between the context element vectors, context factor vectors, combination vectors and performance drivers and the measure. The system of the present invention uses different types of predictive models to identify the best fit relationship: neural network, CART, projection pursuit regression, generalized additive model (GAM), GARCH, MMDR, MARS, redundant regression network, ODE, boosted Naïve Bayes Regression, relevance vector, hierarchical Bayes, Gillespie algorithm models, the support vector method, markov, linear regression, and stepwise regression. The model having the smallest amount of error as measured by applying the root mean squared error algorithm to the test data are the best fit model. Other error algorithms and/or uncertainty measures including entropy measures may also be used. The "relative contribution algorithm" used for completing the analysis varies with the model that was selected as the "best-fit". For example, if the "best-fit" model is a neural net model, then the portion of the measure attributable to each input vector is determined by the formula shown in Table 47.

TABLE 47

$$\left(\underset{k=1}{\overset{k=m}{\text{Sum}}}\underset{j=1}{\overset{j=n}{\text{Sum}}} I_{jk} \times O_k \Big/ \underset{j=1}{\overset{j=n}{\text{Sum}}} I_{ik}\right) \Big/ \underset{k=1}{\overset{k=m}{\text{Sum}}}\left(\underset{j=1}{\overset{j=n}{\text{Sum}}} I_{jk} \times O_k\right)$$

Where
$I_{jk}$ = Absolute value of the input weight from input node j to hidden node k
$O_k$ = Absolute value of output weight from hidden node k
M = number of hidden nodes
N = number of input nodes After completing the best fit calculations, the bots review the lives of the context elements that impact measure performance. If one or more of the elements has an expected life that is shorter than the forecast time period stored in the system settings table (162), then a separate model will be developed to reflect the removal of the impact from the element(s) that are expiring. The resulting values for relative component of context contributions to measure performance are then calculated and saved in the subject schema table (157). If the calculations are related to a commercial business then the value of each contribution will also be saved. The overall model of measure performance is saved in the measure layer table (145). Every measure bot contains the information shown in Table 48.

TABLE 48

1. Unique ID number (based on date, hour, minute, second of creation)
2. Creation date (date, hour, minute, second)
3. Mapping information
4. Storage location
5. Hierarchy or group
6. Entity
7. Measure
8. Context component or combination After the measure bots are initialized by the software in block 391 they activate in accordance with the frequency specified by the user (40) in the system settings table (162). After being activated, the bots retrieve information and complete the analysis of the measure performance. As described previously, the resulting relative contribution percentages are saved in the subject schema table (157) by entity. The overall model of measure performance is saved in the measure layer table (145) by entity before processing advances to a software block 392.

The software in block 392 checks the measure layer table (145) in the contextbase (50) to determine if all subject measures are current. If all measures are not current, then processing returns to software block 302 and the processing described above for this portion (300) of the application software is repeated. Alternatively, if all measure models are current, then processing advances to a software block 394.

The software in block 394 retrieves the previously stored values for measure performance from the measure layer table (145) before processing advances to a software block 395. The software in block 395 checks the bot date table (163) and deactivates measure relevance bots with creation dates before the current system date. The software in block 395 then retrieves the information from the system settings table (162) and the measure layer table (145) in order to initialize a bot for each entity being analyzed. bots are independent components of the application software of the present invention that complete specific tasks. In the case of measure relevance bots, their tasks are to determine the relevance of each of the different measures to entity performance and determine the priority that appears to be placed on each of the different measures is there is more than one. The relevance and ranking of each measure is determined by using a series of predictive models to find the best fit relationship between the measures and entity performance. The system of the present invention uses several different types of predictive models to identify the best fit relationship: neural network, CART, projection pursuit regression, generalized additive model (GAM), GARCH, MMDR, redundant regression network, markov, ODE, boosted naive Bayes Regression, the relevance vector method, the support vector method, linear regression, and stepwise regression. The model having the smallest amount of error as measured by applying the root mean squared error algorithm to the test data are the best fit model. Other error algorithms including entropy measures may also be used. Bayes models are used to define the probability associated with each relevance measure and the Viterbi algorithm is used to identify the most likely contribution of all elements, factors, resources, projects, events, and risks by entity. The relative contributions are saved in the measure layer table (145) by entity. Every measure relevance bot contains the information shown in Table 49.

TABLE 49

1. Unique ID number (based on date, hour, minute, second of creation)
2. Creation date (date, hour, minute, second)
3. Mapping information
4. Storage location
5. Hierarchy or group
6. Entity
7. Measure After the measure relevance bots are initialized by the software in block 395 they activate in accordance with the frequency specified by the user (40) in the system settings table (162). After being activated, the bots retrieve information and complete the analysis of the measure performance. As described previously, the relative measure contributions to measure performance and the associated probability are saved in the measure layer table (145) by entity before processing advances to a software block 396.

The software in block 396 retrieves information from the measure table (145) and then checks the measures for the entity hierarchy to determine if the different levels are in alignment. As discussed previously, lower level measures that are out of alignment can be identified by the presence of measures from the same level with more impact on subject measure performance. For example, employee training could be shown to be a strong performance driver for the entity. If the human resources department (that is responsible for both training and performance evaluations) had been using only a timely performance evaluation measure, then the measures would be out of alignment. If measures are out of alignment, then the software in block 396 prompts the manager (41) via the measure edit data window (708) to change the measures by entity in order to bring them into alignment. Alternatively, if measures by entity are in alignment, then processing advances to a software block 397.

The software in block 397 checks the bot date table (163) and deactivates frontier bots with creation dates before the current system date. The software in block 397 then retrieves information from the event risk table (156), the system settings table (162) and the scenarios table (168) in order to initialize frontier bots for each scenario. Bots are independent components of the application software of the present invention that complete specific tasks. In the case of frontier bots, their primary task is to define the efficient frontier for entity performance measures under each scenario. The top leg of the efficient frontier for each scenario is defined by successively adding the features, options and performance drivers that improve performance while increasing risk to the optimal mix in resource efficiency order. The bottom leg of the efficient frontier for each scenario is defined by successively adding the features, options and performance drivers that decrease performance while decreasing risk to the optimal mix in resource efficiency order. Every frontier bot contains the information shown in Table 50.

TABLE 50

Figure 12:
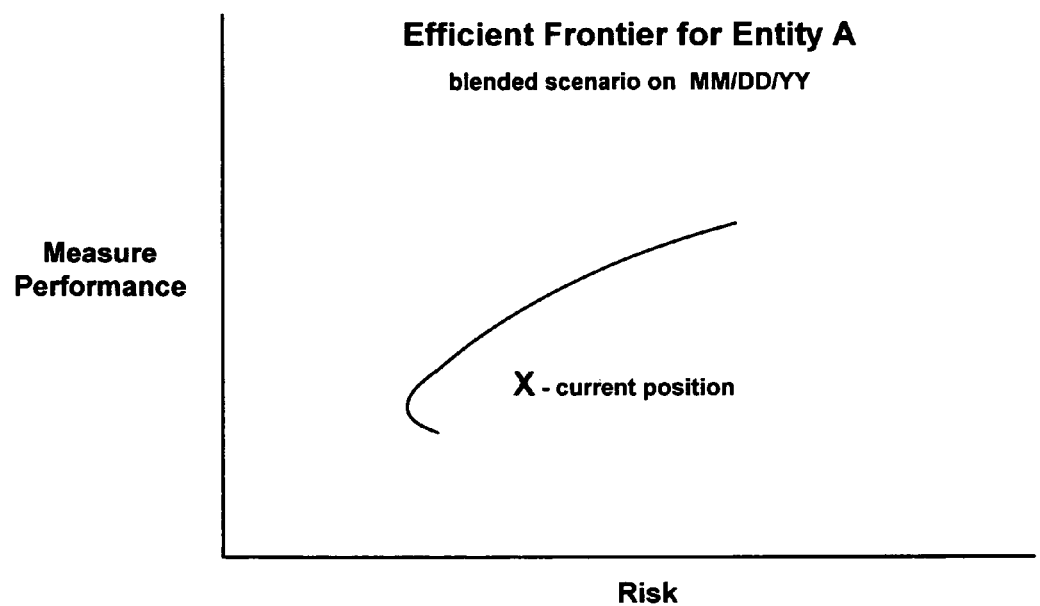
FIG. 12 is a sample report showing the efficient frontier for Entity XYZ and the current position of XYZ relative to the efficient frontier.
Figure 13:
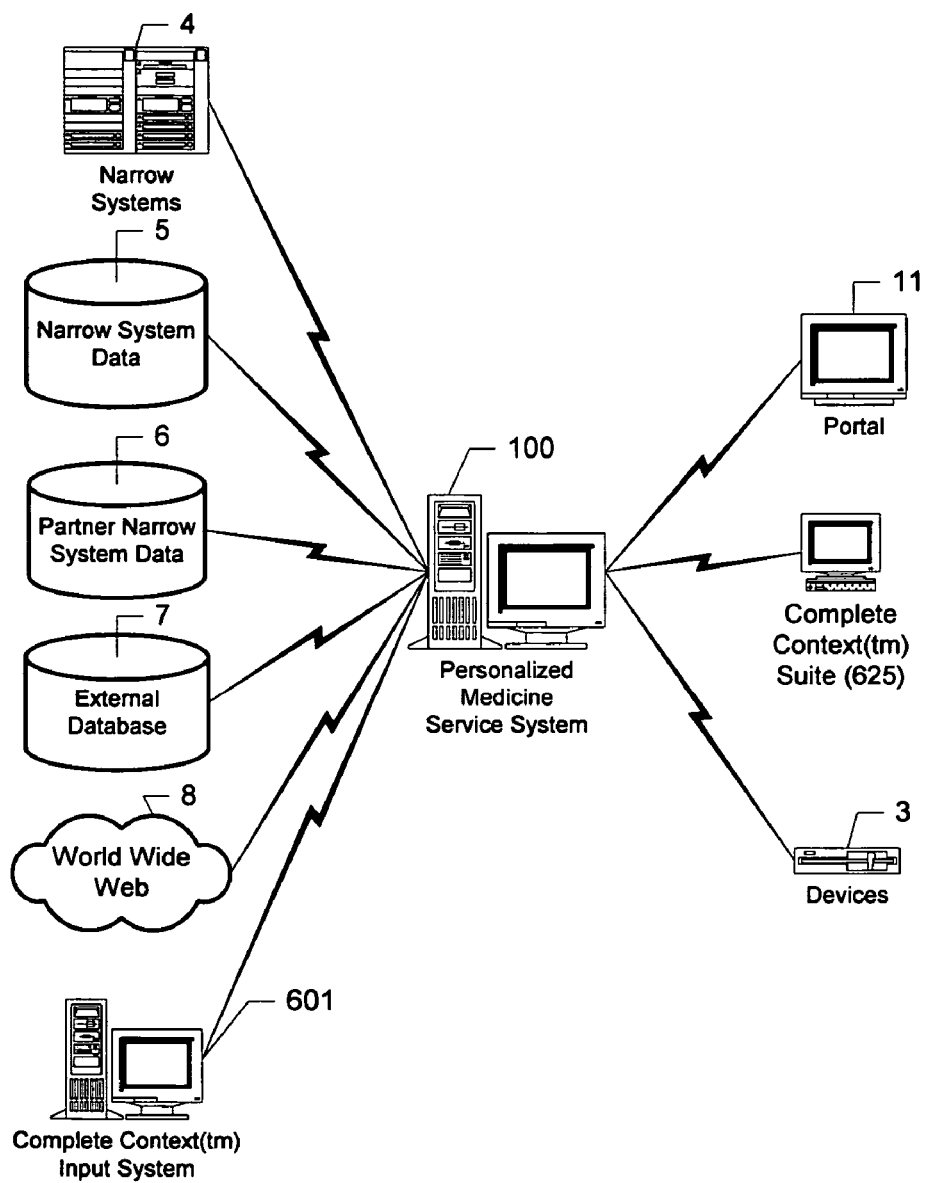
FIG. 13 is a diagram showing one embodiment of a Personalized Medicine Service (100) for a clinic.
Figure 14:
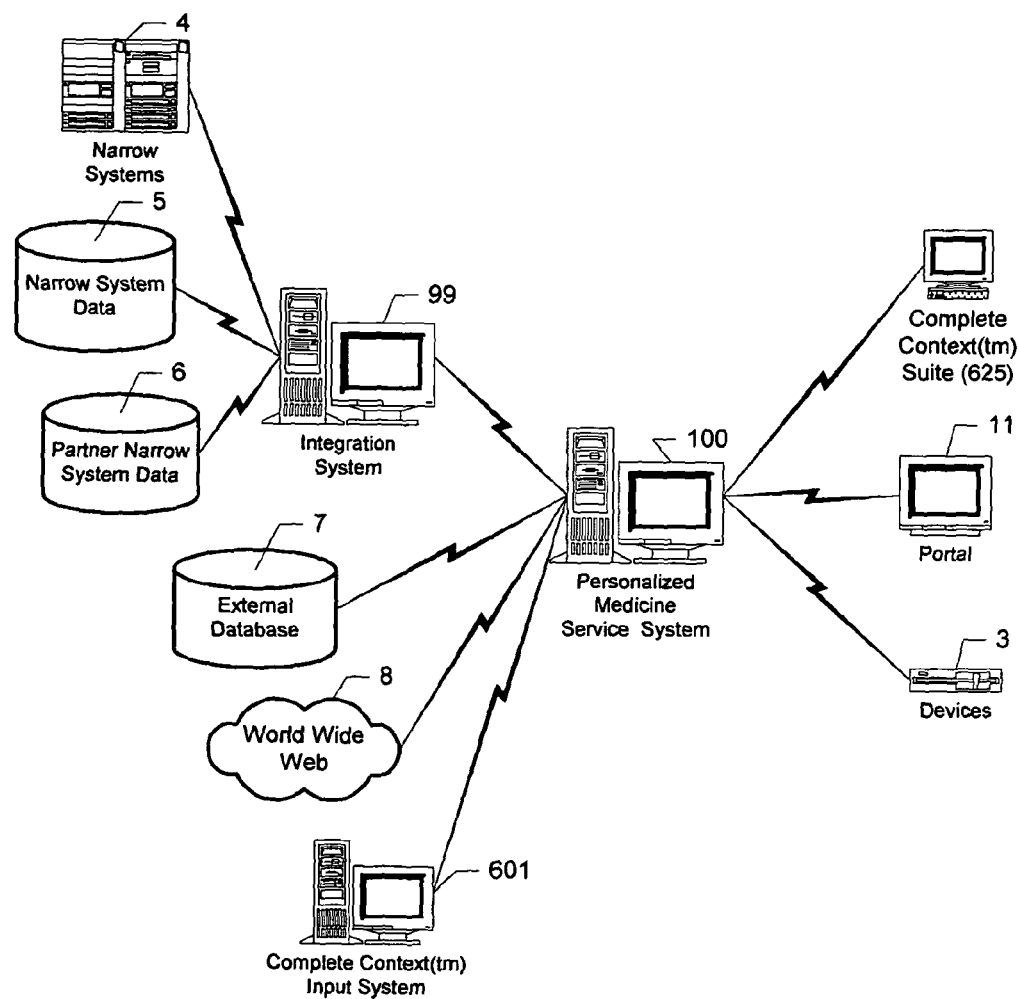
FIG. 14 is a diagram showing how the Personalized Medicine Service (100) for a clinic can be used in conjunction with an integration platform or exchange (99)
Figure 15:
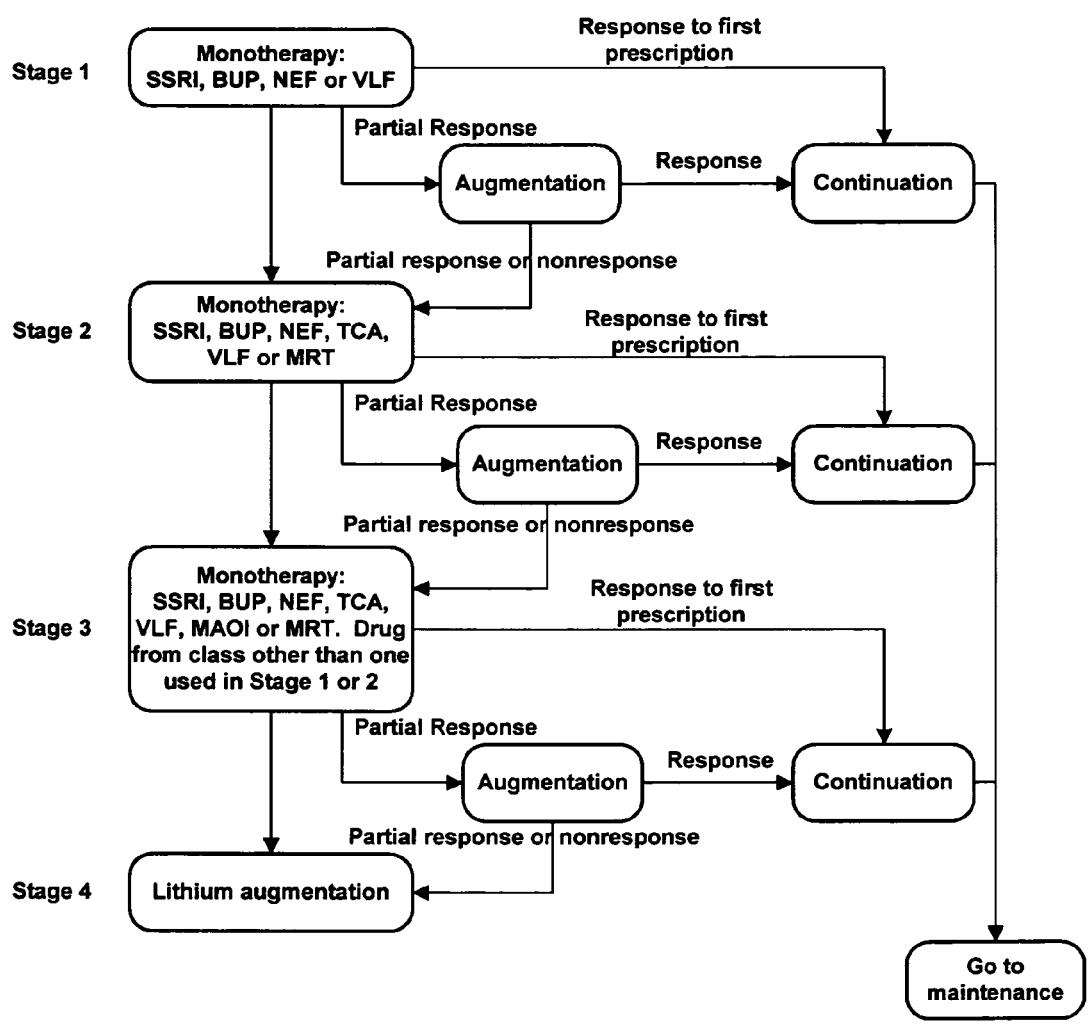
FIG. 15 is a diagram showing a portion of a process map for treating a mental health patient.
Figure 16:
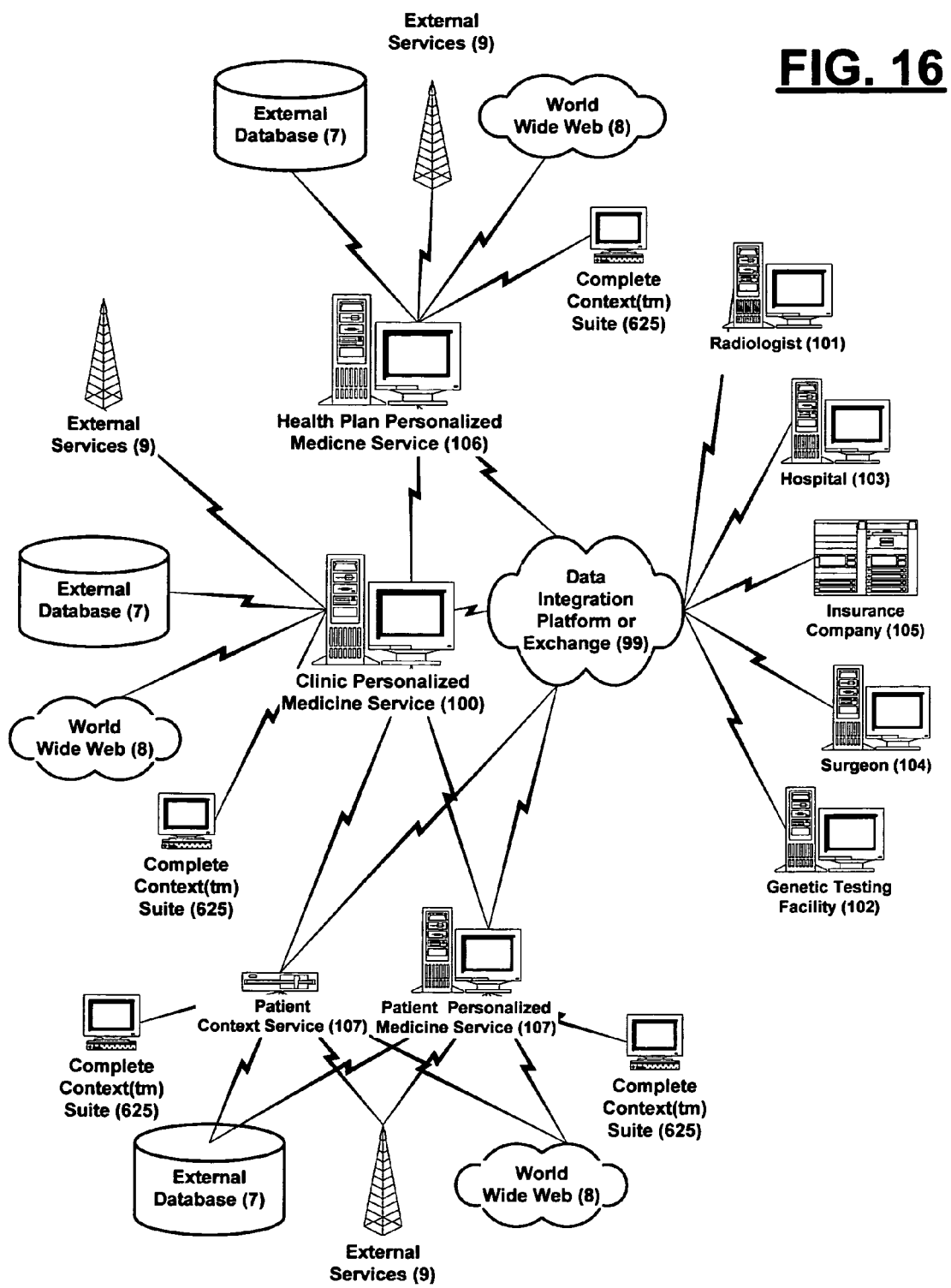
FIG. 16 is a diagram showing an embodiment of the Personalized Medicine Service (100) for a clinic that is connected with a Personalized Medicine Service (107) for a patient, a a Personalized Medicine Service (106) for a health plan and an exchange (99)

1. Unique ID number (based on date, hour, minute, second of creation)
2. Creation date (date, hour, minute, second)
3. Mapping information
4. Storage location
5. Entity
6. Scenario: normal, extreme and blended After the software in block 397 initializes the frontier bots, they activate in accordance with the frequency specified by the user (40) in the system settings table (162). After completing their calculations, the results of all three sets of calculations (normal, extreme and most likely) are saved in the report table (153) in sufficient detail to generate a chart like the one shown in FIG. 12 before processing advances to a software block 398.

The software in block 398 takes the previously stored entity schema from the subject schema table (157) and combines it with the relationship information in the relationship layer table (144) and the measure layer table (145) to develop the entity ontology. The ontology is then stored in the ontology table (152) using the OWL language. Use of the rdf (resource description framework) based OWL language will enable the communication and synchronization of the entities ontology with other entities and will facilitate the extraction and use of information from the semantic web. The semantic web rule language (swrl) that combines OWL with Rule ML can also be used to store the ontology. After the relevant entity ontology is saved in the contextbase (50), processing advances to a software block 402.

Complete Context Service Propagation

The flow diagrams in FIG. 8A and FIG. 8B detail the processing that is completed by the portion of the application software (400) that identifies valid context space, identifies principles, integrates the different entity contexts into an overall context, propagates a Complete Context™ Service and optionally displays and prints management reports detailing the measure performance of an entity. Processing in this portion of the application software (400) starts in software block 402.

The software in block 402 calculates expected uncertainty by multiplying the user (40) and subject matter expert (42) estimates of narrow system (4) uncertainty by the relative importance of the data from the narrow system for each function measure. The expected uncertainty for each measure is expected to be lower than the actual uncertainty (measured using $R^2$ as discussed previously) because total uncertainty is a function of data uncertainty plus parameter uncertainty (i.e. are the specified elements, resources and factors the correct ones) and model uncertainty (does the model accurately reflect the relationship between the data and the measure). After saving the uncertainty information in the uncertainty table (150) processing advances to a software block 403.

The software in block 403 retrieves information from the relationship layer table (144), the measure layer table (145) and the context frame table (160) in order to define the valid context space for the current relationships and measures stored in the contextbase (50). The current measures and relationships are compared to previously stored context frames to determine the range of contexts in which they are valid with the confidence interval specified by the user (40) in the system settings table (162). The resulting list of valid frame definitions stored in the context space table (151). The software in this block also completes a stepwise elimination of each user specified constraint. This analysis helps determine the sensitivity of the results and may indicate that it would be desirable to use some resources to relax one or more of the established constraints. The results of this analysis are stored in the context space table (151) before processing advances to a software block 410.

The software in block 410 integrates the one or more entity contexts into an overall entity context using the weightings specified by the user (40) or the weightings developed over time from user preferences. This overall context and the one or more separate contexts are propagated as a SOAP compliant Personalized Medicine Service (100). Each layer is presented separately for each function and the overall context. As discussed previously, it is possible to bundle or separate layers in any combination. This information in the service is communicated to the Complete Context™ Suite (625), narrow systems (4) and devices (3) using the Complete Context™ Service Interface (711) before processing passes to a software block 414. It is to be understood that the system is also capable of bundling this the context information by layer in one or more bots as well as propagating a layer containing this information for use in a computer operating system, mobile operating system, network operating system or middleware application.

The software in block 414 checks the system settings table (162) in the contextbase (50) to determine if a natural language interface (714) is going to be used. If a natural language interface is going be used, then processing advances to a software block 420. Alternatively, if a natural language interface is not going to be used, then processing advances to a software block 431.

Figure 11:
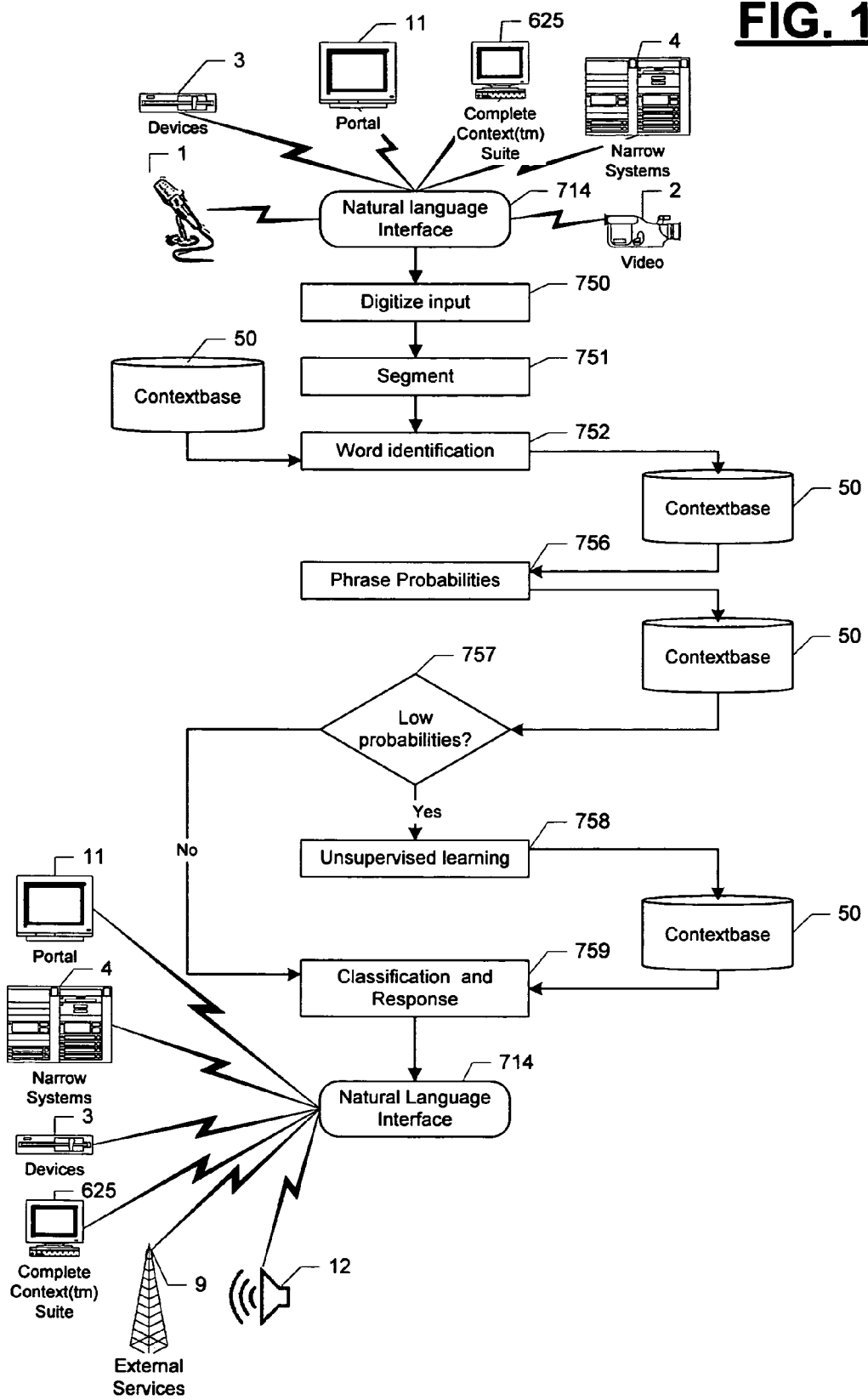
FIG. 11 is a diagram showing how the Personalized Medicine Service (100) develops and supports a natural language interface (714)

The software in block 420 combines the ontology developed in prior steps in processing with unsupervised natural language processing to provide a true natural language interface to the system of the present invention (100). A true natural language interface is an interface that provides the system of the present invention with an understanding of the meaning of the words as well as a correct identification of the words. As shown in FIG. 11, the processing to support the development of a true natural language interface starts with the receipt of audio input to the natural language interface (714) from audio sources (1), video sources (2), devices (3), narrow systems (4), a portal (11) and/or services in the Complete Context™ Suite (625). From there, the audio input passes to a software block 750 where the input is digitized in a manner that is well know. After being digitized, the input passes to a software block 751 where it is segmented into phonemes using a constituent-context model. The phonemes are then passed to a software block 752 where they are compared to previously stored phonemes in the phoneme table (170) to identify the most probable set of words contained in the input. The most probable set of words are saved in the natural language table (169) in the contextbase (50) before processing advances to a software block 756.

The software in block 756 compares the word set to previously stored phrases in the phrase table (172) and the ontology from the ontology table (152) to classify the word set as one or more phrases. After the classification is completed and saved in the natural language table (169), processing passes to a software block 757.

The software in block 757 checks the natural language table (169) to determine if there are any phrases that could not be classified with a weight of evidence level greater than or equal to the level specified by the user (40) in the system settings table (162). If all the phrases could be classified within the specified levels, then processing advances to a software block 759. Alternatively, if there were phrases that could not be classified within the specified levels, then processing advances to a software block 758.

The software in block 758 uses the constituent-context model that uses word classes in conjunction with a dependency structure model to identify one or more new meanings for the low probability phrases. These new meanings are compared to known phrases in an external database (7) such as the Penn Treebank and the system ontology (152) before being evaluated, classified and presented to the user (40). After classification is complete, processing advances to software block 759.

The software in block 759 uses the classified input and ontology to generate a response (that may include the completion of actions) to the translated input and generate a response to the natural language interface (714) that is then forwarded to a device (3), a narrow system (4), an external service (9), a portal (11), an audio output device (12) or an service in the Complete Context™ Suite (625). This process continues until all natural language input has been processed. When this processing is complete, processing advances to a software block 431.

The software in block 431 checks the system settings table (162) in the contextbase (50) to determine if services or bots are going to be created. If services or bots are not going to be created, then processing advances to a software block 433. Alternatively, if services or bots are going to be created, then processing advances to a software block 432.

The software in block 432 supports the development interface window (712) that supports four distinct types of development projects by the Complete Context™ Programming System (610):

1. the development of extensions to Complete Contexts Suite (625) in order to provide the user (40) with the specific information for a given user requirement;
2. the development of Complete Context™ Bots (650) to complete one or more actions, initiate one or more actions, complete one or more events, respond to requests for actions, respond to actions, respond to events, obtain data or information and combinations thereof. The software developed using this option can be used for software bots or agents and robots;
3. programming devices (3) with rules of behavior for different contexts that are consistent with the context frame being provided—i.e. when in church (reference layer location) do not ring unless it is the boss (element) calling; and
4. the development of new context aware services.

The first screen displayed by the Complete Context™ Programming System (610) asks the user (40) to identify the type of development project. The second screen displayed by the Complete Context™ Programming System (610) will depend on which type of development project the user (40) is completing. If the first option is selected, then the user (40) is given the option of using pre-defined patterns and/or patterns extracted from existing narrow systems (4) to modify one or more of the services in the Complete Context™ Suite (625). The user (40) can also program the service extensions using C++ or Java with or without the use of patterns.

If the second option is selected, then the user (40) is shown a display of the previously developed entity schema (157) for use in defining an assignment and context frame for a Complete Context™ Bot (650). After the assignment specification is stored in the bot assignment table (167), the Complete Context™ Programming System (610) defines a probabilistic simulation of bot performance under the three previously defined scenarios. The results of the simulations are displayed to the user (40) via the development interface window (712). The Complete Context™ Programming System (610) then gives the user (40) the option of modifying the bot assignment or approving the bot assignment. If the user (40) decides to change the bot assignment, then the change in assignment is saved in the bot assignment table (167) and the process described for this software block is repeated. Alternatively, if the user (40) does not change the bot assignment, then Complete Context™ Programming System (610) completes two primary functions. First, it combines the bot assignment with results of the simulations to develop the set of program instructions that will maximize bot performance under the forecast scenarios. The bot programming includes the entity ontology and is saved in the bot assignment table (167). In one embodiment Prolog is used to program the bots. Prolog is used because it readily supports the situation calculus analyses used by the Complete Context™ Bots (650) to evaluate their situation and select the appropriate course of action. Each Complete Context™ Bot (650) has the ability to interact with bots and entities that use other schemas or ontologies in an automated fashion.

If the third option is selected, then the previously information about the context quotient for the device (3) is developed and used to select the pre-programmed options (i.e. ring, don't ring, silent ring, etc.) that will be presented to the user (40) for implementation. The user (40) will also be given the ability to construct new rules for the device (3) using the parameters contained within the device-specific context frame.

If the fourth option is selected, then the user (40) is given a pre-defined context frame interface shell along with the option of using pre-defined patterns and/or patterns extracted from existing narrow systems (4) to develop a new service. The user (40) can also program the new service completely using C# or Java.

When programming is complete using one of the four options, processing advances to a software block 433. The software in block 433 prompts the user (40) via the report display and selection data window (713) to review and select reports for printing. The format of the reports is either graphical, numeric or both depending on the type of report the user (40) specified in the system settings table (162). If the user (40) selects any reports for printing, then the information regarding the selected reports is saved in the report table (153). After the user (40) has finished selecting reports, the selected reports are displayed to the user (40) via the report display and selection data window (713). After the user (40) indicates that the review of the reports has been completed, processing advances to a software block 434. The processing can also pass to block 434 if the maximum amount of time to wait for no response specified by the user (40) in the system settings table is exceeded before the user (40) responds.

The software in block 434 checks the report table (153) to determine if any reports have been designated for printing. If reports have been designated for printing, then processing advances to a block 435. It should be noted that in addition to standard reports like a performance risk matrix and the graphical depictions of the efficient frontier shown (FIG. 12), the system of the present invention can generate reports that rank the elements, factors, resources and/or risks in order of their importance to measure performance and/or measure risk by entity, by measure and/or for the entity as a whole. The system can also produce reports that compare results to plan for actions, impacts and measure performance if expected performance levels have been specified and saved in appropriate context layer. The software in block 435 sends the designated reports to the printer (118). After the reports have been sent to the printer (118), processing advances to a software block 437. Alternatively, if no reports were designated for printing, then processing advances directly from block 434 to block 437. The software in block 437 checks the system settings table (162) to determine if the system is operating in a continuous run mode. If the system is operating in a continuous run mode, then processing returns to block 205 and the processing described previously is repeated in accordance with the frequency specified by the user (40) in the system settings table (162). Alternatively, if the system is not running in continuous mode, then the processing advances to a block 438 where the system stops.

Thus, the reader will see that the system and method described above transforms data, information and knowledge from disparate devices (3) and narrow systems (4) into a Personalized Medicine Service (100). The level of detail, breadth and speed of the analysis gives users of the Personalized Medicine Service (100) the ability to create context and apply it to solving real world health problems in an fashion that is uncomplicated and powerful.

While the above description contains many specificities, these should not be construed as limitations on the scope of the invention, but rather as an exemplification of one embodiment thereof. Accordingly, the scope of the invention should be determined not by the embodiment illustrated, but by the appended claims and their legal equivalents.

The invention claimed is:

1. A personalized medicine service method, comprising:
using a computer to prepare data from a plurality of subject related systems for use in processing,
defining a subject using at least a portion of said data and a plurality of user input,
analyzing said data as required to define and store a complete context for a health of said subject, and
using said complete context to complete useful activities selected from the group consisting of customizing a treatment, customizing a test, ordering a treatment, ordering a test, forecasting a sustainable longevity, analyzing an impact of one or more user specified changes on a subject performance, capturing a subject related knowledge from one or more subject matter experts, customizing information for the subject, customizing a product or a service for the subject, displaying a graph about subject performance, exchanging an element with one or more subjects or entities in an automated fashion, forecasting one or more future values of subject related variables, identifying one or more metrics and rules for monitoring subject performance, identifying one or more changes that will optimize subject performance on one or more function measures, quantifying one or more risks to a subject function measure performance, quantifying an impact of surprises on subject performance, simulating subject performance, establishing one or more priorities for subject actions and commitments, establishing an expected performance level for the subject, reviewing subject performance using user defined measures, identifying a data and information combination that is most relevant to the subject, identifying one or more subject preferences, loading a data and information combination that is most relevant to the subject into a cache and creating a summary of subject context
where the complete context for the health of said subject further comprises a context for one or more functions of one or more biological entities where said biological entities comprise one or more elements of the complete context and are selected from the group consisting of macromolecular complex, protein, rna, dna, methylation, gene, organ, cell, monomer, dimer, large oligomer, aggregate and particle, and
where the subject consists of a patient-entity system and where an entity in the patient-entity system is not an element of the complete context and is selected from the group consisting of precinct, caucus, city county, state/province, regional, national, multi-national, global, household, neighborhood, community, region, nuclear family, extended family, clan, ethnic group, organization, multi-organization, industry, market, economy, team, group, department, division, company, species, genus, family, order, class, phylum, kingdom, x-ylation, organelles, cells, structures, organs, organic systems, organism, compounds, chemicals, catalysts, minerals, sediment, rock, landform, plate, continent, planet, quark, protons, neutrons, electrons, atoms, molecules, dark matter, asteroids, comets, planets, stars, solar system, galaxy, universe, compounds, minerals, components, subassemblies, assemblies, subsystems, goods, systems, pond, lake, bay, sea, ocean, creek, stream, river, current, atmosphere, clouds, lightning, precipitation, storm and wind.

2. The method of claim 1, wherein the complete context is defined by components of context selected from the group consisting of a reference frame location, one or more projects, one or more events, one or more factors, one or more resources, one or more elements, one or more actions, one or more transactions, one or more processes, one or more measures, one or more constraints, one or more preferences, one or more lexicons and combinations thereof.

3. The method of claim 1, wherein the subject consists of a patient or two or more patients.

4. The method of claim 1, wherein the useful activities further comprise developing one or more programs for subject related devices, creating a true natural language interface for the subject and developing one or more subject related software programs.

5. A program storage device readable by a computer, tangibly embodying a program of instructions executable by a computer to perform method steps for performing a personalized medicine service method, comprising:
preparing data from a plurality of subject related systems for use in processing,
defining a subject using at least a portion of said data and a plurality of user input,
analyzing at least a portion of said data as required to define a complete context for a health of said subject, and
using said complete context to complete useful activities selected from the group consisting of customizing a treatment, customizing a test, ordering a treatment, ordering a test, forecasting a sustainable longevity, analyzing an impact of one or more user specified changes on a subject performance, capturing a subject related knowledge from one or more subject matter experts, customizing information for the subject, customizing a product or a service for the subject, displaying a graph about subject performance, exchanging an element with one or more subjects or entities in an automated fashion, forecasting one or more future values of subject related variables, identifying one or more metrics and rules for monitoring subject performance, identifying one or more changes that will optimize subject performance on one or more function measures, quantifying one or more risks to a subject function measure performance, quantifying an impact of surprises on subject performance, simulating subject performance, establishing one or more priorities for subject actions and commitments, establishing an expected performance level for the subject, reviewing subject performance using user defined measures, identifying a data and information combination that is most relevant to the subject, identifying one or more subject preferences, loading a data and information combination that is most relevant to the subject into a cache and creating a summary of subject context
where the complete context for the health of said subject further comprises a context for one or more functions of one or more biological entities where said biological entities comprise one or more elements of the complete context and are selected from the group consisting of macromolecular complex, protein, rna, dna, methylation, gene, organ, cell, monomer, dimer, large oligomer, aggregate and particle,
where the subject consists of a patient, two or more patients or a patient-entity system where an entity in the patient-entity system is not an element of the complete context, and
where the computer readable medium comprises a plurality of bots, components or intelligent agents.

6. The program storage device of claim 5, wherein the complete context for a health of a subject is stored in a contextbase.

7. The program storage device of claim 6, wherein the contextbase stores data, information and knowledge using one or more context layers where context layers are selected from the group consisting of an element layer, a resource layer, an environment layer, a relationship layer, a lexicon layer, a measure layer, a transaction layer, a reference frame layer and combinations thereof.

8. The program storage device of claim 5, wherein the complete context is distributed via an Internet, a network, a service or a bot.

9. The program storage device of claim 5, wherein the complete context for the health of said subject further comprises a context for one or more functions of one or more more biological entities associated with said subject where the one or more biological entities are selected from the group consisting of macromolecular complex, protein, rna, dna, methylation, gene, organelle, cell, monomer, dimer, large oligomer, aggregate and particle.

10. A system for providing a personalized medicine service, comprising:
   a computer with a processor having circuitry to execute instructions; a storage device available to said processor with sequences of instructions stored therein, which when executed cause the processor to:
      prepare data from a plurality of subject related systems for use in processing,
      define a subject using at least a portion of said data and a plurality of user input,
      analyze at least a portion of said data as required to define a complete context for a health of said subject, and
      using said complete context to complete useful activities selected from the group consisting of customizing a treatment, customizing a test, ordering a treatment, ordering a test, forecasting a sustainable longevity, analyzing an impact of one or more user specified changes on a subject performance, capturing a subject related knowledge from one or more subject matter experts, customizing information for the subject, customizing a product or a service for the subject, displaying a graph about subject performance, exchanging an element with one or more subjects or entities in an automated fashion, forecasting one or more future values of subject related variables, identifying one or more metrics and rules for monitoring subject performance, identifying one or more changes that will optimize subject performance on one or more function measures, quantifying one or more risks to a subject function measure performance, quantifying an impact of surprises on subject performance, simulating subject performance, establishing one or more priorities for subject actions and commitments, establishing an expected performance level for the subject, reviewing subject performance using user defined measures, identifying a data and information combination that is most relevant to the subject, identifying one or more subject preferences, loading a data and information combination that is most relevant to the subject into a cache, and creating a summary of subject context
      where the complete context for the health of said subject further comprises a context for one or more functions of one or more biological entities where said biological entities comprise one or more elements of the complete context where the context for one or more functions of said biological entities further comprises an identification of a network of entities that have an impact on each of one or more biological entity functions and the one or more biological entities are selected from the group consisting of macromolecular complex, protein, rna, dna, methylation, gene, organ, cell, monomer, dimer, large oligomer, aggregate and particle, and
      where the subject consists of a patient-entity system and where an entity in the patient-entity system is not an element of the complete context and is selected from the group consisting of precinct, caucus, city county, state/province, regional, national, multi-national, global, household, neighborhood, community, region, nuclear family, extended family, clan, ethnic group, organization, multi-organization, industry, market, economy, team, group, department, division, company, species, genus, family, order, class, phylum, kingdom, x-ylation, organelles, cells, structures, organs, organic systems, organism, compounds, chemicals, catalysts, minerals, sediment, rock, landform, plate, continent, planet, quark, protons, neutrons, electrons, atoms, molecules, dark matter, asteroids, comets, planets, stars, solar system, galaxy, universe, compounds, minerals, components, subassemblies, assemblies, subsystems, goods, systems, pond, lake, bay, sea, ocean, creek, stream, river, current, atmosphere, clouds, lightning, precipitation, storm and wind.

11. The system of claim 10, wherein the subject consists of a patient, or two or more patients.

* * * * *